(12) United States Patent
Johncock et al.

(10) Patent No.: US 9,517,190 B2
(45) Date of Patent: Dec. 13, 2016

(54) COATED TITANIUM DIOXIDE TO REDUCE THE WHITENING EFFECT ON SKIN

(71) Applicant: Symrise AG, Holzminden (DE)

(72) Inventors: William Johncock, Reinbek (DE); Simone Peters, Buchholz (DE); Martina Issleib, Hoisdorf (DE); Jürgen Claus, Bevern (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 14/661,487

(22) Filed: Mar. 18, 2015

(65) Prior Publication Data

US 2015/0265510 A1    Sep. 24, 2015

(30) Foreign Application Priority Data

Mar. 18, 2014 (EP) .................... 14160519

(51) Int. Cl.
*A61K 9/50* (2006.01)
*A61K 8/29* (2006.01)
*A61K 8/26* (2006.01)
*A61K 8/37* (2006.01)
*A61Q 17/04* (2006.01)
*A61K 8/02* (2006.01)
*C09C 1/36* (2006.01)

(52) U.S. Cl.
CPC ............. *A61K 8/29* (2013.01); *A61K 8/0241* (2013.01); *A61K 8/26* (2013.01); *A61K 8/37* (2013.01); *A61K 9/5021* (2013.01); *A61K 9/5089* (2013.01); *A61Q 17/04* (2013.01); *C09C 1/3661* (2013.01); *C09C 1/3669* (2013.01); *C09C 1/3692* (2013.01); *A61K 2800/413* (2013.01); *A61K 2800/622* (2013.01); *A61K 2800/63* (2013.01)

(58) Field of Classification Search
CPC ............................ A61K 9/5021; A61K 9/5089
See application file for complete search history.

(56) References Cited

U.S. PATENT DOCUMENTS 3,649,321 A    3/1972  Durrant et al.
8,545,891 B1  10/2013  Halpern et al.

FOREIGN PATENT DOCUMENTS

WO    2009/126859 A2    10/2009
WO    2012/110302 A2     8/2012
WO    2012110302 A2 *    8/2012  ....... A61K 2800/622

* cited by examiner

Primary Examiner — Carlos Azpuru
(74) Attorney, Agent, or Firm — Dilworth & Barrese, LLP

(57) ABSTRACT

The present invention relates to coated titanium dioxide particles, wherein at least one coating layer comprises an ester made from a mixture of fatty alcohol and C6 to C12 aliphatic acids as coating material.

15 Claims, 4 Drawing Sheets

COATED TITANIUM DIOXIDE TO REDUCE THE WHITENING EFFECT ON SKIN

FIELD OF INVENTION

The present invention belongs to the area of cosmetic and pharmaceutical preparations, especially dermatological preparations and refers to the protection of the human skin and human hair against the harmful effects of ultraviolet (UV) radiation. The cosmetic and pharmaceutical preparations of the invention comprise a specially coated titanium dioxide which reduces the residual whitening effect, in particular on skin after application and improves the skin feel of the finished formulation.

STATE OF THE ART

UV absorbers are compounds which have a pronounced absorption capacity for ultraviolet radiation. They are used in particular as sunscreens in cosmetic, dermatological and pharmacological preparations, but also to improve the light fastness of industrial products, such as paints, varnishes, plastics, textiles, polymers such as, for example, polymers and copolymers of mono- and diolefins, polystyrenes, polyurethanes, polyamides, polyesters, polyureas and polycarbonates, packaging materials and rubbers.

UV rays are classified according to wavelength as UVA rays (320-400 nm, UVA-I: 340-400 nm, UVA-II: 320-340 nm) or UVB rays (280-320 nm). UV rays can cause acute and chronic damage to the skin, the type of damage depending on the wavelength of the radiation. For instance, UVB radiation can cause sunburn (erythema) extending to most severe burning of the skin; reduction in enzyme activities, weakening of the immune system, disturbances of the DNA structure and changes in the cell membrane are also known as harmful effects of UVB rays. UVA rays penetrate into deeper layers of the skin where they can accelerate the aging process of the skin. The shorter wave UVA-II radiation additionally contributes to the development of sunburn. Moreover, UVA radiation can trigger phototoxic or photo allergic skin reactions. Very frequent and unprotected irradiation of the skin by sunlight leads to a loss of skin elasticity and to increased development of wrinkles. In extreme cases, pathogenic changes in the skin extending to skin cancer are observed. To attenuate these negative effects of UV radiation, materials which absorb or reflect UV light, generally called UV absorbers, are used in cosmetic, dermatological and pharmacological preparations. The UV absorbers are classified as UVA and UVB absorbers depending on the location of their absorption maxima; if a UV absorber absorbs both UVA and UVB, it is referred to as a UVA/B broadband absorber.

The UV absorbers typically used are classified as organic, based on carbon, hydrogen and oxygen atoms or inorganic pigments based on titanium dioxide or zinc oxide.

Titanium dioxide has been used for decades as a white pigment for paints and make-up due to its very high refractive index which makes it one of the whitest pigments known, with a refractive index of about 2.6. As most cosmetic, dermatological and pharmacological preparations for protection of the human skin have a refractive index of about 1.5, it is very difficult to hide the whiteness of titanium dioxide when it is incorporated into such a preparation (Fairhurst & Mitchnick: of Sunscreens Development, Evaluation and Regulatory Aspects, 2nd Edition, edited by Shaath et. al. Cosmetic Science & Technology Series/Volume 15 Chapter 17, Page 320, 1997, Marcel Dekker Inc).

The scattering of radiation by pigmentary particles is not only dependent upon the refractive index but also upon their particle size, and the maximum scattering of visible radiation for titanium dioxide is about 220 nm (see Fairhurst reference, page 322).

As titanium dioxide is also a semiconductor with a band gap of 3.05 eV (=405 nm) UV radiation with wavelengths of less than 405 nm will be absorbed by it. It is this absorption which makes titanium dioxide a candidate to be used in UV protection products. However, the desirable whitening effect of pigmentary grades of titanium dioxide with particle sizes greater than 200 nm for its application in paints and decorative cosmetics is an undesirable effect in cosmetic, dermatological and pharmacological preparations for protection of the human skin against the harmful effects of UV radiation, as the residual whitening left on the skin is considered to be unattractive. So in the past 2 decades of the 20th century, grades of titanium dioxide were developed which had a much smaller particle size (20-80 nm) to reduce the whitening effect caused by reflection, while at the same time, significantly improving the abilities of the substance to reflect UV radiation in the UVB range. However pure grades of nano titanium dioxide have two major properties that had to be overcome before they could be incorporated into cosmetic, dermatological and pharmacological preparations for protection of the human skin against the harmful effects of UV radiation. Firstly, as titanium dioxide absorbs UV radiation, it is an efficient photocatalyst which causes release of free radicals involved in oxidative processes that are undesirable in cosmetic, dermatological and pharmacological preparations for protection of the human skin. Secondly, once incorporated into an emulsion, solid pigment particles of titanium dioxide tend to agglomerate into larger particles and once these particles achieve a size of 220-250 nm, they again become efficient in reflecting white light.

These two properties were, to some extent overcome, especially for the reduction of the photoreactivity, by efficiently coating the individual particles of titanium dioxide with various coatings, for example silica (SiO2), aluminium hydroxide (Al2(OH)3, aluminium oxide (Al2O3), alumina, sodium hexametaphosphate (Na(PO3)6), sodium metaphosphate (Na(PO3)n, aluminium stearate, stearic acid, lauric acid, dimethylpolysiloxane, dimethicone, methylypolysiloxane, simethicone, either as single components or as mixtures.

As a result, the use of nano grades of titanium dioxide became a commonly used ingredient in cosmetic, dermatological and pharmacological preparations for protection of the human skin against the harmful effects of UV radiation. However, the residual whitening effect of these qualities of titanium dioxide in cosmetic, dermatological and pharmacological preparations for protection of the human skin against the harmful effects of UV radiation is still unacceptable. In addition the incorporation of nano titanium dioxide in such preparations also leaves the skin with an unacceptable feel, in that it is not smooth but dull and blunt, which then require the addition of other more cosmetic ingredients such as waxes and oils to attenuate this, building in complexity and cost to the manufacturing of the preparations.

It has also been discovered that if the particles of titanium dioxide are coated with aluminium salts or oxides and then formulated in cosmetic and pharmaceutical, especially dermatological preparations for protection of the human skin against the harmful effects of UV radiation containing the widely used UVA filter Avobenzone there is an undesirable reaction between aluminium ions and Avobenzone resulting in the formation of insoluble aluminium complexes of Avobenzone which crystallise out of the formulation thereby reducing its efficacy and aesthetics as described in US 2012/0294916 A1.

Object of the present invention is thus to provide titanium dioxide in cosmetic and pharmaceutical preparations, especially in dermatological preparations, to protect human skin against the harmful effects of UV radiation, without the prior disadvantages mentioned above.

DESCRIPTION OF THE INVENTION

Surprisingly, it has been observed that by coating titanium dioxide with a wax that comprises an ester made from a mixture of fatty alcohols and C6 to C12 aliphatic acids, the residual whitening effects are visibly much reduced. Further, it has been observed that cosmetic and pharmaceutical preparations for protection of the human skin against the harmful effects of UV radiation, preferably the respective dermatological preparations comprising titanium dioxide coated with the wax, comprising an ester made from a mixture of fatty alcohol and C6 to C12 aliphatic acids have a much smoother skin feel than preparations with titanium dioxide, which is not coated with the respective wax.

Therefore, the present invention relates to coated titanium dioxide particles, wherein at least one coating layer comprises an ester made from mixture of fatty alcohol and C6 to C12 aliphatic acids as coating material.

"Coating material" in the sense of the invention is a substance or a mixture of several substances which is used to coat particles.

BRIEF DESCRIPTION OF THE DRAWINGS

The present invention will be described in greater detail with reference to the accompanying drawings in which.

DESCRIPTION OF THE PREFERRED EMBODIMENTS

Figure 1:
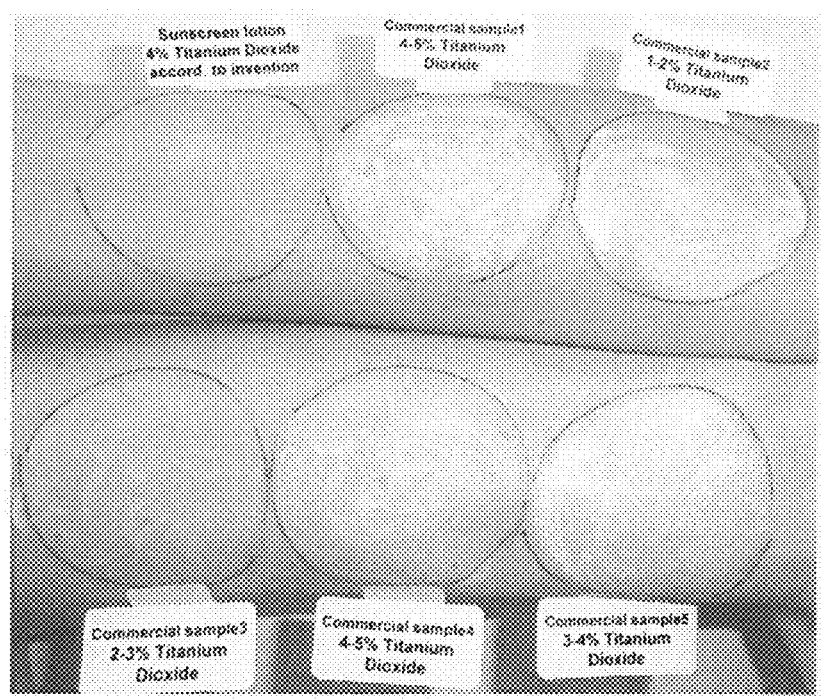
FIG. 1 is a photograph of residual whitening on the skin after application of 2.5 mg/cm2 of commercial sunscreen formulations vs. a laboratory made formulation containing 4% of a titanium dioxide coated with cetearyl nonoanoate, according to the invention, which have been rubbed into the skin for 15 seconds.

Concerning the mixture of fatty alcohol and C6 to C12 aliphatic acids, which results in an fatty ester, all combinations of fatty alcohol and C6 to C12 aliphatic acids is possible. Preferably, the resulting fatty esters derived from C12-C30 fatty alcohols esterified with C6 to C12 acids. More preferably, the fatty esters derived from C14 to C20 fatty alcohols and most preferably from C16 to C18 alcohols esterified with C8 to C10 acids.

Preferably, the wax, respectively the ester made from a mixture of fatty alcohol and C6 to C12 aliphatic acids, as coating material is a C16-C18 nonanoate derivative or a mixture thereof. Thus, in a preferred embodiment the at least one coating layer comprises cetearyl nonoate and/or cetearyl isononoate as coating material.

Most preferred are coated titanium dioxide particles, wherein at least one coating layer comprises cetearyl nonanoate (SymMollient® S sold by Symrise AG) as coating material.

Additionally, surprisingly by coating titanium dioxide with an ester made from a mixture of fatty alcohol and C6 to C12 aliphatic acids, as coating material, preferably a C16-C18 nonanoate derivative or a mixture thereof, more preferably cetearyl nonoate and/or cetearyl isononoate, no interactions with Avobenzone, which is a common UV filter, has been observed, when a further coating layer is used to coat the titanium dioxide particles.

Therefore, another preferred embodiment of the present invention is the coated titanium dioxide particles according to the invention, wherein the titanium dioxide particles comprise one or more additional coating layers, whereby the additional coating material is selected from the group consisting of silica (SiO2), aluminium hydroxide $(Al_2(OH)_3$, aluminium oxide $(Al_2O_3)$, alumina, sodium hexametaphosphate $(Na(PO_3)_6)$, sodium metaphosphate $(Na(PO_3)n$, aluminium stearate, stearic acid, lauric acid, dimethylpolysiloxane, dimethicone, methylypolysiloxane, simethicone, or mixtures thereof.

The coating layers comprising wax as the coating material and the additional coating material selected from silica (SiO2), aluminium hydroxide $(Al_2(OH)_3$, aluminium oxide $(Al_2O_3)$, alumina, sodium hexametaphosphate $(Na(PO_3)_6)$, sodium metaphosphate $(Na(PO_3)n$, aluminium stearate, stearic acid, lauric acid, dimethylpolysiloxane, dimethicone, methylypolysiloxane, simethicone, or mixtures thereof, is variable in the coating layer order. This means that the titanium oxide particles may be firstly coated with the wax and afterwards with the additional coating material selected from silica (SiO2), aluminium hydroxide $(Al_2(OH)_3$, aluminium oxide $(Al_2O_3)$, alumina, sodium hexametaphosphate $(Na(PO_3)_6)$, sodium metaphosphate $(Na(PO_3)n$, aluminium stearate, stearic acid, lauric acid, dimethylpolysiloxane, dimethicone, methylypolysiloxane, simethicone, or mixtures thereof; or vice versa.

Therefore, a preferred embodiment are coated titanium dioxide particles according to the invention, that comprise
(i) at least a first coating layer comprises a coating material selected from silica (SiO2), aluminium hydroxide $(Al_2(OH)_3$, aluminium oxide $(Al_2O_3)$, alumina, sodium hexametaphosphate $(Na(PO_3)_6)$, sodium metaphosphate $(Na(PO_3)n$, aluminium stearate, stearic acid, lauric acid, dimethylpolysiloxane, dimethicone, methylypolysiloxane, simethicone, or mixtures thereof, and
(ii) at least a second (outer) coating layer, wherein the coating material comprises an ester made from a mixture of fatty alcohol and C6 to C12 aliphatic acids, as coating material, preferably a C16-C18 nonanoate derivative or a mixture thereof, more preferably cetearyl nonoate and/or cetearyl isononoate.

Most preferred are coated titanium dioxide particles that comprise
(i) at least a first coating layer comprises a coating material selected from silica (SiO2), aluminium hydroxide (Al$_2$(OH)$_3$, aluminium oxide (Al$_2$O$_3$), alumina, sodium hexametaphosphate (Na(PO$_3$)$_6$), sodium metaphosphate (Na(PO$_3$)n, aluminium stearate, stearic acid, lauric acid, dimethylpolysiloxane, dimethicone, methylypolysiloxane, simethicone, or mixtures thereof, and
(ii) at least a second (outer) coating layer, wherein the coating material comprises cetearyl nonanoate (SymMollient® S sold by Symrise AG).

Optionally, the coated titanium dioxide particles according to the invention, comprise
(i) at least a first coating layer, wherein the coating material comprises an ester made from a mixture of fatty alcohol and C6 to C12 aliphatic acids, as coating material, preferably a C16-C18 nonanoate derivative or a mixture thereof, more preferably cetearyl nonoate and/or cetearyl isononoate, and
(ii) at least a second (outer) coating layer, which comprises a coating material selected from silica (SiO2), aluminium hydroxide (Al$_2$(OH)$_3$, aluminium oxide (Al$_2$O$_3$), alumina, sodium hexametaphosphate (Na(PO$_3$)$_6$), sodium metaphosphate (Na(PO$_3$)n, aluminium stearate, stearic acid, lauric acid, dimethylpolysiloxane, dimethicone, methylypolysiloxane, simethicone, or mixtures thereof.

In this case, most preferred are coated titanium dioxide particles that comprise
(i) at least a first coating layer, wherein the coating material comprises cetearyl nonanoate (SymMollient® S sold by Symrise AG), and
(ii) at least a second (outer) coating layer, which comprises a coating material selected from silica (SiO2), aluminium hydroxide (Al$_2$(OH)$_3$, aluminium oxide (Al$_2$O$_3$), alumina, sodium hexametaphosphate (Na(PO$_3$)$_6$), sodium metaphosphate (Na(PO$_3$)n, aluminium stearate, stearic acid, lauric acid, dimethylpolysiloxane, dimethicone, methylypolysiloxane, simethicone, or mixtures thereof.

The coated titanium dioxide particles of the present invention can have more than two coating layers of the above mentioned coating materials. Thus, alternate coating layers of the mentioned coating material can be applied onto a titanium oxide particle. A titanium oxide particle of the present invention may possess up to 4 coating layers.

In a further embodiment the coated titanium dioxide particles of the present invention have a loading capacity of the wax, which comprises an ester made from a mixture of fatty alcohol and C6 to C12 aliphatic acids, as coating material, preferably a C16-C18 nonanoate derivative or a mixture thereof, more preferably cetearyl nonoate and/or cetearyl isononoate, most preferably cetearyl nonanoate (SymMollient® S sold by Symrise AG), in the range from 5 to 25 wt. %, referring to the total weight of a particle. Preferably, the loading capacity is in the range of 10 to 25 wt. %, more preferably in the range of 10 to 15 wt. %., referring to the total weight of a particle.

In a further embodiment the coated titanium dioxide particles of the present invention have a loading capacity of the additional coating material selected from silica (SiO2), aluminium hydroxide (Al$_2$(OH)$_3$, aluminium oxide (Al$_2$O$_3$), alumina, sodium hexametaphosphate (Na(PO$_3$)$_6$), sodium metaphosphate (Na(PO$_3$)n, aluminium stearate, stearic acid, lauric acid, dimethylpolysiloxane, dimethicone, methylypolysiloxane, simethicone, or mixtures thereof, in the range of 5 to 15 wt. %, more preferably in the range of 5 to 10 wt. %, referring to the total weight of a particle.

The coated titanium dioxide particles according to the invention have an average particle size in which at least one dimension of the individual crystals making up the agglomerates of particles is <100 nm.

The coated titanium dioxide particles of the invention are used in cosmetic and pharmaceutical preparations, especially dermatological preparations. Thus, another object of the present invention are cosmetic or pharmaceutical preparations which comprise coated titanium dioxide particles as described above.

Especially, a preferred embodiment of the present invention are cosmetic or pharmaceutical preparations, especially dermatological preparations, that comprise the coated titanium dioxide particles according to the invention described above, in the range of referring to the total preparation The amount of coated titanium dioxide particles according to the invention in the cosmetic and pharmaceutical preparations, preferably dermatological preparations, is in the range of 0.1 to 35 wt. %, preferably 0.3 to 30 wt. %, more preferably 0.5 to 25 wt. % of the total formulation.

UV Filters

A further object of the present invention are cosmetic or pharmaceutical preparations, especially dermatological preparations, comprising the coated titanium dioxides particles of the invention and at least one additional UV filter in an amount from 0.1 to 65.0 wt. %, preferably in the range of 2 to 50 wt. % and most preferably in the range of 5 to 35 wt. %, preferably referring to the total amount of all UV filters, referring to the total amount of the preparation.

The preferred UV filters are selected from the group consisting of:
Avobenzone
Homosalate
Octisalate
Octocrylene
2-Ethylhexyl p-methoxycinnamate
Isoamyl p-methoxycinnamate
3-(4'-methylbenzylidene)-d,l-camphor
2,4,6-trianilino(p-carbo-2'-ethylhexyl-1'-oxy)-1,3,5-triazine
Tris-Biphenyl Triazine
Diethylhexyl Butamido Triazone
Benzylidenemalonate-polysiloxane
2-Ethylhexyl 4-dimethylaminobenzoate
Drometrizole Trisiloxane
Bis-Ethylhexyloxyphenol Methoxyphenyl Triazine
2,2'-Methylenebis(6-(2H-benztriazol-2-yl)-4-1,1,3,3-tetra methylbutyl)-phenol),
Diethylamino Hydroxybenzoyl Hexyl Benzoate
Disodium Phenyl-dibenzimidazole Tetrasulphonate and its salts
Phenylbenzimidazole-sulphonic Acid and its salts
Terephthalylidene Dicamphor Sulfonic Acid and its salts
Benzophenone-4 and its salts
Benzophenone-3
Menthyl anthranilate
Padimate O
Zinc oxide,
and their mixtures.

The cosmetic or pharmaceutical compositions according to the invention may comprises further auxiliaries and additives selected from surfactants, oil bodies, emulsifiers, co-emulsifiers, superfatting agents, pearlising waxes, consistency factors, polymers, silicone compounds, waxes, stabilizers, antidandruff agents, film formers, swelling agents, hydrotropes, preservatives, solubilizers, complexing agents, reducing agents, alkalising agents, perfume oils, dyes, thickeners, fats, lecithins, phospholipids, moisturizers, biogenic agents, anti-oxidants, deodorants, antiperspirants, insect repellants, self-tanning agents, tyrosine inhibitors (depigmenting agents), bodying agents, biogenic active ingredients, antimicrobial agents, antifoams, pigments which have a coloring action, aqueous and non-aqueous plant extracts and the like as additional auxiliaries and additives.

The cosmetic and/or pharmaceutical preparations according to the invention, preferably dermatological preparations, comprising the coated titanium dioxide particles of the invention, have a sun protection factor of at least 2. It is possible to use the coated titanium dioxide particle of the present invention in all cosmetic or pharmaceutical preparations with all possible sun protection factor, likewise 10, 15, 20, 25, 30 or 50.

In a preferred embodiment the cosmetic or pharmaceutical preparations, preferably dermatological preparations, have an UVA protection factor of at least 2, measured by the Colipa Method for in vitro determination of UVA protection, 2011 or the closely related ISO norm ISO 24443-2012 Determination of sunscreen UVA photo protection in vitro.

Cosmetic and/or pharmacological preparations, preferably dermatological preparations, for protection of the human skin against the harmful effects of UV radiation comprising the coated titanium dioxide of the invention alone or in combination with other UV attenuating agents.

In a further preferred embodiment of the invention, a (cosmetic and/or pharmaceutical, preferably dermatological) preparation comprises a total amount of UV filters and/or inorganic pigments such that the preparation of the invention has a sun protection factor of greater than or equal to 2 (preferably greater than or equal to 5). These sunscreens are suitable for protecting skin and hair.

Further, suitable photo protective agents (UV absorbers) for the cosmetic and/or pharmaceutical, preferably dermatological preparation of the present invention, are, for example, organic UV absorbers from the class of 4-aminobenzoic acid and derivatives, salicylic acid derivatives, benzophenone derivatives, dibenzoylmethane derivatives, diphenylacrylates, 3-imidazol-4-ylacrylic acid and its esters, benzofuran derivatives, benzylidenemalonate derivatives, polymeric UV absorbers containing one or more organosilicon radicals, cinnamic acid derivatives, camphor derivatives, trianilino-s-triazine derivatives, 2-hydroxyphenylbenzotriazole derivatives, menthyl anthranilate, benzotriazole derivatives and indole derivatives.

The UV absorbers specified below, which can be used additionally for the purposes of the present invention, are preferred, but of course are not limiting. Preferred UV filters are:

UVB filters:
P-aminobenzoic acid
ethyl p-aminobenzoate (25 mol) ethoxylated
2-ethylhexyl p-dimethylaminobenzoate
homomenthyl salicylate (homosalate) (Neo Heliopan® MS)
2-ethylhexyl salicylate (Neo Heliopan® OS)
triethanolamine salicylate (Neo Heliopan® TS)
menthyl anthranilate (Neo Heliopan® MA)
2-ethylhexyl p-methoxycinnamate (Neo Heliopan® AV)
isoamyl p-methoxycinnamate (Neo Heliopan® E 1000)
2-phenylbenzimidazole sulfonic acid (Neo Heliopan® Hydro) and its salts
3-(4'-trimethylammonium)benzylidenebornan-2-one methyl sulphate
3-(4'-sulpho)benzylidenebornan-2-one and salts
3-(4'-methylbenzylidene)-d,l-camphor (Neo Heliopan® MBC)
N-[(2 and 4)-[2-(oxoborn-3-ylidene)methyl]benzyl]acrylamide polymer
4,4'-[(6-[4-(1,1-dimethyl)aminocarbonyl)phenylamino]-1,3,5-triazine-2,4-diyl)diimino]bis(benzoic acid 2-ethylhexyl ester) (Uvasorb® HEB)
benzylidenemalonate-polysiloxane (Parsol® SLX)
tris(2-ethylhexyl) 4,4',4"-(1,3,5-triazine-2,4,6-triyltriimino)tribenzoate (Uvinul® T150)
2-ethylhexyl 2-cyano-3,3-diphenylacrylate (Neo Heliopan® 303)

Broadband filters:
2-hydroxy-4-methoxybenzophenone-5-sulfonic acid (sulisobenzone, benzophenone-4) or its salts.
2-hydroxy-4-methoxybenzophenone (Neo Heliopan® BB, Oxybenzone, benzophenone-3
disodium 2,2'-dihydroxy-4,4'-dimethoxy-5,5'-disulphobenzophenone
phenol,-(2H-benzotriazol-2-yl-4-methyl-6-(2-methyl-3-(1,3,3,3-tetramethyl-1-(trimethylsilyl)oxy)disiloxanyl)propyl), (Mexoryl® XL)
2,2'-methylenebis(6-(2H-benztriazol-2-yl)-4-1,1,3,3-tetramethylbutyl)-phenol), Tinosorb® M)
2,4-bis[4-(2-ethylhexyloxy)-2-hydroxyphenyl]-1,3,5-triazine
2,4-bis[{(4-(2-ethylhexyloxy)-2-hydroxy}phenyl]-6-(4-methoxyphenyl)-1,3,5-triazine, (Tinosorb® S)
Tris-Biphenyl Triazine (Tinosorb® A2B)
2,4-bis[{(4-(3-sulphonato)-2-hydroxypropyloxy)-2-hydroxy}phenyl]-6-(4-methoxyphenyl)-1,3,5-triazine sodium salt
2,4-bis[{(3-(2-propyloxy)-2-hydroxypropyloxy)-2-hydroxy}phenyl]-6-(4-methoxyphenyl)-1,3,5-triazine
2,4-bis[{4-(2-ethylhexyloxy)-2-hydroxy}phenyl]-6-[4-(2-methoxyethyl-carbonyl)phenylamino]-1,3,5-triazine
2,4-bis[{4-(3-(2-propyloxy)-2-hydroxypropyloxy)-2-hydroxy}phenyl]-6-[4-(2-ethylcarboxyl)phenylamino]-1,3,5-triazine
2,4-bis[{4-(2-ethylhexyloxy)-2-hydroxy}phenyl]-6-(1-methylpyrrol-2-yl)-1,3,5-triazine
2,4-bis[{4-tris(trimethylsiloxysilylpropyloxy)-2-hydroxy}phenyl]-6-(4-methoxyphenyl)-1,3,5-triazine
2,4-bis[{4-(2"-methylpropenyloxy)-2-hydroxy}phenyl]-6-(4-methoxyphenyl)-1,3,5-triazine
2,4-bis[{4-(1',1',1',3',5',5',5'-heptamethylsiloxy-2"-methylpropyloxy)-2-hydroxy}phenyl]-6-(4-methoxyphenyl)-1,3,5-triazine.

UVA filters:
terephthalylidenedibornanesulphonic acid and salts (Mexoryl® SX)
Avobenzone (Neo Heliopan® 357)
hexyl 2-(4-diethylamino-2-hydroxybenzoyl)benzoate (Uvinul® A Plus)
menthyl anthranilate (Neo Heliopan® MA)

UV absorbers (particularly suitable for combination):
homomenthyl salicylate (Neo Heliopan® MS)
terephthalylidenedibornanesulphonic acid and salts (Mexoryl® SX)
2-ethylhexyl 2-cyano-3,3-diphenylacrylate (Neo Heliopan® 303)
N-[(2 and 4)-[2-(oxoborn-3-ylidene)methyl]benzyl]acrylamide polymer 2-ethylhexyl p-methoxycinnamate (Neo Heliopan® AV)
ethyl p-aminobenzoate (25 mol) ethoxylated
isoamyl p-methoxycinnamate (Neo Heliopan® E1000)
2-phenylbenzimidazole sulfonic acid (Neo Heliopan® Hydro) and its salts
2,4,6-trianilino(p-carbo-2'-ethylhexyl-1'-oxy)-1,3,5-triazine (Uvinul® T150)
phenol,2-(2H-benzotriazol-2-yl)-4-methyl-6-(2-methyl-3 (1,3,3,3-tetramethyl-1-(trimethylsilyl)oxy)disiloxanyl)propyl), (Mexoryl® XL)
4,4'-[(6-[4-(1,1-dimethyl)aminocarbonyl)phenylamino]-1,3,5-triazin-2,4-diyl)-diimino]bis(benzoic acid 2-ethylhexyl ester), (Uvasorb® HEB)
3-(4'-methylbenzylidene)-d,l-camphor (Neo Heliopan® MBC)
2-ethylhexyl salicylate (Neo Heliopan® OS)
2-ethylhexyl 4-dimethylaminobenzoate (Padimate O)
2-hydroxy-4-methoxybenzophenone (Neo Heliopan® BB, Oxybenzone, benzophenone-3
2,2'-methylenebis(6-(2H-benzotriazol-2-yl)-4-1,1,3,3-tetramethylbutyl)-phenol), (Tinosorb® M)
2,4-bis[{(4-(2-ethylhexyloxy)-2-hydroxy}phenyl]-6-(4-methoxyphenyl)-1,3,5-triazine, (Tinosorb® S)
benzylidenemalonate-polysiloxane (Parsol® SLX)
hexyl 2-(4-diethylamino-2-hydroxybenzoyl)benzoate (Uvinul® A Plus)
Avobenzone (Neo Heliopan® 357)
menthyl anthranilate (Neo Heliopan® MA).

Furthermore, additional particulate UV filters or inorganic pigments can be used, which if desired may have been rendered hydrophobic, such as the oxides of zinc (ZnO), of iron ($Fe_2O_3$), of zirconium ($ZrO_2$), of silicon ($SiO_2$), of manganese (e.g. MnO), of aluminium ($Al_2O_3$), of cerium (e.g. $Ce_2O_3$) and/or mixtures.

The total amount of all sulfonated water soluble UV filters, like for example but not limited to, phenylbenzimidazole sulfonic acid, and/or Disodium Phenyl Dibenzimidazole Tetrasulphonic Acid and/or Benzophenone-4, and/or terephthalylidenedibornanesulphonic and/or 3-(4'-trimethylammonium)benzylidenebornan-2-one methyl sulphate, and/or 3-(4'-sulpho)benzylidenebornan-2-one, and their salts in cosmetic and pharmaceutical preparations, preferably dermatological preparations, comprising the coated titanium dioxide of the invention, are in the range of 0.1 to 15.0% and more particularly in the range from 0.5 to 10.0% and most particularly in the range of 1.0 to 8.0% of the total formulation.

The amount of disodium phenyl dibenzimidazole tetrasulfonate and its salts used in the cosmetic and pharmaceutical preparations, preferably dermatological preparations, comprising the coated titanium dioxide of the invention, is in the range of 0.1 to 10.0%, preferably in the range from 0.3 to 8% and most preferably in the range from 0.5 to 5.0% of the total formulation.

The amount of phenylbenzimidazole sulfonic acid and its salts used in the cosmetic and pharmaceutical preparations, preferably dermatological preparations, comprising the coated titanium dioxide of the invention, is in the range of 0.1 to 10.0%, preferably in the range from 0.3 to 8% and most preferably in the range from 0.5 to 5.0% of the total formulation.

The amount of Mexoryl® SX and its salts used in the cosmetic and pharmaceutical preparations, preferably dermatological preparations, comprising the coated titanium dioxide of the invention, is in the range of 0.1 to 10.0%, preferably in the range from 0.3 to 8% and most preferably in the range from 0.5 to 5.0% of the total formulation.

The total amount of oil soluble UV filters that may be used in the cosmetic and pharmaceutical preparations, preferably dermatological preparations, comprising the coated titanium dioxide of the invention, for example but not limited to (2-ethylhexyl) 4,4',4"-(1,3,5-triazine-2,4,6-triyltriimino)tribenzoate and/or -tert-butyl-4'-methoxydibenzoylmethane, and/or 2-ethylhexyl 4-dimethylaminobenzoate, and/or Mexoryl® XL and/or Uvasorb® HEB and/or Tinosorb® S and/or Benzophenone-3 and/or Parsol® SLX and/or Neo Heliopan® MA, and/or isoamyl p-methoxycinnamate, and/or 2-ethylhexyl salicylate, and/or homosalate, and/or ethylhexyl methoxycinnamate, and/or octocrylene, and/or Uvinul® A Plus, and/or 3-(4'-methylbenzylidene)-d, l-camphor, 2-ethylhexyl 4-dimethylaminobenzoate, is in the range of 0.1 to 55 wt.-%, particularly in the range of 0.5 to 40%, most particularly in the range of 1 to 30% of the total formulation.

The amount of ethylhexyl methoxycinnamate used in the cosmetic and pharmaceutical preparations, preferably dermatological preparations, comprising the coated titanium dioxide of the invention, is in the range of 0.1 to 20.0%, preferably in the range from 0.3 to 15% and most preferably in the range from 0.5 to 10.0% of the total formulation.

The amount of isoamyl p-methoxycinnamate used in the cosmetic and pharmaceutical preparations, preferably dermatological preparations, comprising the coated titanium dioxide of the invention, is in the range of 0.1 to 20.0%, preferably in the range from 0.3 to 15% and most preferably in the range from 0.5 to 10.0% of the total formulation.

The amount of Octocrylene used in the cosmetic and pharmaceutical preparations, preferably dermatological preparations, comprising the coated titanium dioxide of the invention, is in the range of 0.1 to 20.0%, preferably in the range from 0.3 to 15% and most preferably in the range from 0.5 to 10.0% of the total formulation.

The amount of salicylate esters used in the cosmetic and pharmaceutical preparations, preferably dermatological preparations, comprising the coated titanium dioxide of the invention, is in the range of 0.1 to 20.0%, preferably in the range from 0.3 to 15% and most preferably in the range from 0.5 to 10.0% of the total formulation. When Ethylhexyl salicylate is chosen as the UV filter, it is advantageous that its total amount ranges from 0.1 to 5.0% of the formulation and when Homosalate is chosen as the UV filter it is advantageous that its total amount ranges from 0.1 to 15.0% of the formulation The amount of Avobenzone used in the cosmetic and pharmaceutical preparations, preferably dermatological preparations, comprising the coated titanium dioxide of the invention, is in the range of 0.1 to 10.0%, preferably in the range from 0.3 to 7.0% and most preferably in the range from 0.5 to 5.0% of the total formulation.

The amount of Uvasorb® HEB used in the cosmetic and pharmaceutical preparations, preferably dermatological preparations, comprising the coated titanium dioxide of the invention, is in the range of 0.1 to 10.0%, preferably in the range from 0.3 to 7.0% and most preferably in the range from 0.5 to 5.0% of the total formulation.

The amount of Uvinul® T-150 used in the cosmetic and pharmaceutical preparations, preferably dermatological preparations, comprising the coated titanium dioxide of the invention, is in the range of 0.1 to 10.0%, preferably in the range from 0.3 to 7.0% and most preferably in the range from 0.5 to 5.0% of the total formulation.

The amount of 2,4-bis[{(4-(2-ethylhexyloxy)-2-hydroxy}phenyl]-6-(4-methoxyphenyl)-1,3,5-triazine, (Tinosorb® S) used in the cosmetic and pharmaceutical preparations, preferably dermatological preparations, comprising the coated titanium dioxide of the invention, is in the range of 0.1 to 10.0%, preferably in the range from 0.3 to 7.0% and most preferably in the range from 0.5 to 5.0% of the total formulation.

The amount of 2,2'-methylenebis(6-(2H-benzotriazol-2-yl)-4-1,1,3,3-tetramethylbutyl)-phenol), (Tinosorb® M) used in the cosmetic and pharmaceutical preparations, preferably dermatological preparations, comprising the coated titanium dioxide of the invention, is in the range of 0.1 to 10.0%, preferably in the range from 0.3 to 7.0% and most preferably in the range from 0.5 to 5.0% of the total formulation.

The amount of Tris-Biphenyl Triazine (Tinosorb® A2B), used in the cosmetic and pharmaceutical preparations, preferably dermatological preparations, comprising the coated titanium dioxide of the invention, is in the range of 0.1 to 10.0%, preferably in the range from 0.3 to 7.0% and most preferably in the range from 0.5 to 5.0% of the total formulation.

The amount of benzylidenemalonate-polysiloxane (Parsol® SLX) used the cosmetic and pharmaceutical preparations, preferably dermatological preparations, comprising the coated titanium dioxide of the invention, is in the range of 0.1 to 10.0%, preferably in the range from 0.3 to 7.0% and most preferably in the range from 0.5 to 5.0% of the total formulation.

The total amount of micro fine organic and/or inorganic pigments, for example but not limited to triazine derivatives and/or Zinc Oxide (coated and un-coated), and/or titanium dioxide (coated or un-coated) that may be used in the cosmetic and pharmaceutical preparations, preferably dermatological preparations, comprising the coated titanium dioxide particles of the invention, is in the range of 0.1 to 35%, preferably in the range from 0.3 to 25% and more preferably in the range from 0.5 to 15.0% and most preferably in the range from 0.75% to 10.0%. When titanium dioxide is chosen as the UV filter, it is advantageous that its total amount ranges from 0.1% to 10.0% of the formulation. When Zinc Oxide is chosen as the UV filter it is advantageous that its total amount ranges from 0.1% to 10.0% of the formulation and when one or more triazine organic pigment(s) are chosen it is advantageous that its total amount ranges from 0.1% to 10.0% of the formulation.

The combination of the coated titanium particles of the invention with additional UV filters, for example with the UV filters as described above and particularly with the UV filters which is described as "particularly suitable for combination", leads to synergistic effects in the degree of protection offered against UVB and UVA radiation as determined by measurements to determine sun protection factors against UVA and/or UVB radiation.

Thus, the combination of the coated titanium particles of the invention with one or more of the UV filters described above as well as any allowed UV filters for use in sun protection products legislated in:

Europe: by the Cosmetics regulation (EC) No 1223/2009 of the Council of European Communities published in the in the Official Journal of the European Communities.

Australia: in the positive list of allowed UV filters published by the Australian Therapeutic Goods Administration in the Australian Register of Therapeutic Goods (ARTG).

It is furthermore advantageous to add one or more of the highly photostable UV absorbers, selected from methylbenzylidenecamphor, 2-ethylhexyl-2-cyano-3,3'-diphenylacrylate, octyltriazone, Uvasorb® HEB, ethylhexyl salicylate, homomenthyl salicylate, phenylbenzimidazolesulphonic acid, Benzophenone-3, Mexoryl® SX, Mexoryl® XL, Tinosorb® S, Tinosorb® M, Tinsorb® A2B, Neo Heliopan® AP, or Parsol® SLX, or mixtures thereof.

In case that one of the UV filter is Avobenzone, it is advantageously, to add a photo stabilising emollient, like 2,6-Diethylhexyl Naphthalate sold under the trade name of Corapan® TQ from Symrise, to improve the photo stability of Avobenzone.

Synergies of titanium dioxide coated with cetearyl nonanoate together with other constituents that do not absorb UV light, with regard to an improved protection against sunlight, are to be expected in cosmetic, dermatological and pharmacological preparations, for example but not limited to: polymers, emulsifiers (anionic, cationic, zwitterionic, nonionic, quaternaries), thickeners, rheology modifiers, C2- to C50 alkyl (branched or linear) esters or alkyl (branched or linear) aromatic esters, triols or their esters, glycols or their esters, monohydric alcohols or their esters, waxes, silicone derivatives, chelating agents, preservation agents, vitamins and their derivatives, tanning agents, tanning accelerators, skin whitening or lightening agents, amino acids and their derivatives, peptides and their derivatives, carotenoids ad their derivatives, anti-inflammatory ingredients, fragrances, cooling or heating agents, insect repellents, flavonoids, anti-oxidants, plant extracts, and non-nano sized pigments (coloured or white).

The cosmetic and/or pharmaceutical preparations, in particular the dermatological preparations according to the invention can be formulated in customary manner and preferably serve as cosmetic and pharmaceutical sunscreens, particularly as dermatological sunscreens and also for the treatment, care and cleansing of the skin and/or the hair and as a make-up product in decorative cosmetics.

The cosmetic and/or pharmaceutical preparations, in particular the dermatological preparations according to the invention serve for the protection of skin and hair against UV radiation can be in the use forms conventionally used, i.e. in the form of oil-in-water, water-in-oil or mixed emulsion, in the form of milk, in the form of lotion or cream, aerosol, hydrodispersion gel or oil gel (emulsifier-free), spray, foam, solution, powder, pencil preparation or in the form of any other customary cosmetic and pharmaceutical (particularly dermatological) preparations. Preparations such as shampoo, rinse, conditioner, gel, lotion, spray or cream are preferably used for protection of the hair against UV rays.

The cosmetic and/or pharmaceutical preparations, in particular the dermatological preparations according to the invention can have the customary composition and can be used for cosmetic and/or dermatological sun protection, and also for the treatment, care and cleansing of the skin and/or of the hair and as a make-up product in decorative cosmetics. Accordingly, the preparations according to the present invention can, depending on their formulation, be used, for example, as skin protection cream, cleansing milk, sunscreen lotion, nourishing cream, day cream or night cream. The preparations according to the present invention can, depending on their formulation, also be used for example, in hair care compositions such as shampoos, conditioners, 2 in 1 preparations, anti-dandruff shampoos, hair tonics, hair lotions, hair rinses, styling products, sprays, etc. In some instances, it is possible and advantageous to use the preparations according to the present invention as bases for pharmaceutical preparations. Preference is given, in particular, to those cosmetic and dermatological preparations in the form of a skin care, hair care or make-up product. Typical embodiments are creams, gels e.g. but not limited to hydrogels, hydrodispersion gels, oil gels; lotions, alcoholic and aqueous/alcoholic solutions, emulsions in their various forms for example but not limited to oil in water (O/W), water in oil (W/O), mixed emulsions, PIT emulsions, Pickering emulsions, microemulsions, nano-emulsions; aerosol foams, non-aerosol foams, aerosols sprays, non-aerosol sprays, pump sprays, serums, roll-ons, pastes, balsams, or stick preparations.

The pharmaceutical and cosmetic preparations of the present invention are preferably dermatological preparations, which are preferably administered to the skin and/or hair.

The cosmetic or pharmaceutical preparations according to the invention may comprise as further auxiliaries and additives surfactants, oil bodies, emulsifiers, co-emulsifiers, superfatting agents, pearlising waxes, consistency factors, polymers, silicone compounds, waxes, stabilizers, antidandruff agents, film formers, swelling agents, hydrotropes, preservatives, solubilizers, complexing agents, reducing agents, alkalising agents, perfume oils, dyes, thickeners, fats, lecithins, phospholipids, moisturizers, biogenic agents, antioxidants, deodorants, antiperspirants, insect repellants, self-tanning agents, tyrosine inhibitors (depigmenting agents), bodying agents, biogenic active ingredients, antimicrobial agents, antifoams, pigments which have a coloring action, aqueous and non-aqueous plant extracts and the like as additional auxiliaries and additives.

Preferably, the cosmetic and pharmaceutical preparations, particularly dermatological preparations according to the present invention are applied to the skin and/or the hair in a sufficient amount in the manner customary for cosmetics or pharmaceutical and dermatological preparations.

The cosmetic or pharmaceutical preparations according to the invention, preferably in form of a dermatological preparation is preferably selected from the group consisting of creams, gels, hydrogels, hydrodispersion gels, oil gels, lotions, balsams.

Cosmetic and Pharmaceutical Preparations

Cosmetic and pharmaceutical preparations according to the present invention may include similar additives, such as for example oil bodies or emulsifiers. Therefore, the border between cosmetic and pharmaceutical preparations is in flow and it should be understood that components cited for one application are recommended for the other mutatis-mutandis without literal repetition.

Surfactants

Preferred embodiments of the cosmetic and pharmaceutical, especially dermatological preparations of the invention may also comprise anionic, cationic, nonionic and/or amphoteric surfactants (included in the term surfactant is the term emulsifier). Surfactants are amphiphilic substances which can dissolve or disperse organic, nonpolar substances in water. In this context, the hydrophilic components of a surfactant molecule are usually polar functional groups, for example —$COO^-$, —$OSO_3^{2-}$, —$SO_3^-$, while the hydrophobic parts as a rule are nonpolar hydrocarbon radicals. Surfactants are in general classified according to the nature and charge of the hydrophilic molecular moiety. A distinction can be made between four groups here:

anionic surfactants,
cationic surfactants,
amphoteric surfactants and
nonionic surfactants.

Anionic surfactants as a rule contain carboxylate, sulphate or sulphonate groups as functional groups. In aqueous solution, they form negatively charged organic ions in an acid or neutral medium. Cationic surfactants are almost exclusively characterized by the presence of a quaternary ammonium group. In aqueous solution, they form positively charged organic ions in an acid or neutral medium. Amphoteric surfactants contain both anionic and cationic groups and accordingly behave like anionic or cationic surfactants in aqueous solution, depending on the pH. In a strongly acid medium they have a positive charge, and in an alkaline medium a negative charge. On the other hand, they are zwitterionic in the neutral pH range. Polyether and polysaccharide chains are typical of nonionic surfactants. Nonionic surfactants do not form ions in an aqueous medium. Specifically useful are:

acylamino acids (and salts thereof), such as:
acyl glutamates, for example sodium acyl glutamate, di-TEA-palmitoyl aspartate and sodium caprylic/capric glutamate,
acyl peptides, for example palmitoyl hydrolysed milk protein, sodium cocoyl hydrolysed soya protein and sodium/potassium cocoyl hydrolysed collagen,
sarcosinates, for example myristoyl sarcosine, TEA-lauroyl sarcosinate, sodium lauroyl sarcosinate and sodium cocoyl sarcosinate,
taurates, for example sodium lauroyl taurate and sodium methylcocoyl taurate,
acyl lactylates, lauroyl lactylate, caproyl lactylate alaninates
carboxylic acids and derivatives, such as for example: TEA stearate, Glyceryl stearates, PEG glyceryl stearates, lauric acid, aluminium stearate, magnesium alkanolate and zinc undecylenate,
ester-carboxylic acids, for example: calcium stearoyl lactylate, laureth-6 citrate and sodium PEG-4 lauramide carboxylate, glyceryl stearates, glyceryl-oleylstearates, glyceryl citrates, glyceryl oleyl citrates,
ether-carboxylic acids, for example sodium laureth-13 carboxylate and sodium PEG-6 cocamide carboxylate,
Glucoside esters, such as for example:
cetearyl glucoside, lauryl glucoside
phosphoric acid esters and salts, such as, for example: cetyl phosphate (mono, di cetyl and their mixtures), Potassium cetyl phosphate, (mono, di cetyl and their mixtures), DEA cetyl phosphate (mono, di cetyl and their mixtures), DEA-oleth-10 phosphate and dilaureth-4 phosphate,
sulphonic acids and salts, such as acyl isethionates, e.g. sodium/ammonium cocoyl isethionate, alkylarylsulphonates,
alkylsulphonates, for example sodium coco-monoglyceride sulphate, sodium C12-14 olefinsulphonate, sodium lauryl sulphoacetate and magnesium PEG-3 cocamide sulphate,
sulphosuccinates, for example dioctyl sodium sulphosuccinate, disodium laurethsulphosuccinate, disodium laurylsulphosuccinate and disodium undecylenamido-MEA-sulphosuccinate and
sulphuric acid esters, such as: alkyl ether sulphate, for example sodium, ammonium, magnesium, MIPA, TIPA laureth sulphate, sodium myreth sulphate and sodium C12-13 pareth sulphate,
alkyl sulphates, for example sodium, ammonium and TEA lauryl sulphate.

Cationic surfactants which are advantageously used are
alkylamines,
alkylimidazoles,
ethoxylated amines,
quaternary surfactants,
$RNH_2CH_2CH_2COO^-$ (at pH=7)

RNHCH$_2$CH$_2$COO— B$^+$ (at pH=12) B$^+$=any desired cation, e.g. Na$^+$ and esterquats.

Quaternary surfactants contain at least one N atom which is covalently bonded to 4 alkyl or aryl groups. This leads to a positive charge, independently of the pH. Alkylbetaine, alkylamidopropylbetaine and alkylamidopropylhydroxysulphaine are advantageous. The cationic surfactants used can further preferably be chosen from the group consisting of quaternary ammonium compounds, in particular benzyltrialkylammonium chlorides or bromides, such as, for example, benzyldimethylstearylammonium chloride, and also alkyltrialkylammonium salts, for example cetyltrimethylammonium chloride or bromide, alkyldimethylhydroxyethylammonium chlorides or bromides, dialkyldimethylammonium chlorides or bromides, alkylamideethyltrimethylammonium ether sulphates, alkylpyridinium salts, for example lauryl- or cetylpyridinium chloride, imidazoline derivatives and compounds having a cationic character, such as amine oxides, for example alkyldimethylamine oxides or alkylaminoethyldimethylamine oxides. Cetyltrimethyl-ammonium salts in particular are advantageously used.

Amphoteric surfactants which are advantageously to be used are:
  acyl/dialkylethylenediamine, for example sodium acylamphoacetate, disodium acylamphodipropionate, disodium alkylamphodiacetate, sodium acylamphohydroxypropylsulphonate, disodium acylamphodiacetate and sodium acylamphopropionate,
  N-alkylamino acids, for example aminopropyl alkylglutamide, alkylaminopropionic acid, sodium alkylimidodipropionate and lauroamphocarboxyglycinate.
  acylamphohydroxypropylsulphonate, disodium acylamphodiacetate and sodium acylamphopropionate,
  N-alkylamino acids, for example aminopropyl alkylglutamide, alkylaminopropionic acid, sodium alkylimidodipropionate and lauroamphocarboxyglycinate.
  Nonionic surfactants which are advantageously used are
  alcohols,
  alkanolamides, such as cocamides MEA/DEA/MIPA,
  amine oxides, such as cocoamidopropylamine oxide,
  ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides, such as lauryl glucoside, decyl glucoside and coco-glycoside.
  sucrose esters, sucrose ethers
  polyglycerol esters, diglycerol esters, monoglycerol esters polyglyceryl-2 dipolyhydroxystearate (Dehymuls® PGPH), polyglyceryl-3 diisostearate (Lameform® TGI), polyglyceryl-4 isostearate (Isolan® GI 34), polyglyceryl-3 oleate, diisostearyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (polyglycerol caprate 12010/90), polyglyceryl-3 cetyl ether (Chimexane® NL), polyglyceryl-3 distearate (Cremophor® GS 32), polyglyceryl-2 stearate (Hostacerin® DGMS) and polyglyceryl polyricineoleate (Admul® WOL 1403), and mixtures thereof.
  methylglucose esters, esters of hydroxy acids The use of a combination of anionic and/or amphoteric surfactants with one or more nonionic surfactants is further advantageous.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:
  products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
  $C_{12/18}$ fatty acid monoesters and diesters of addition products of 1 to 30 mol ethylene oxide onto glycerol;
  glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric emulsifiers. Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grunau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates.

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol), menthone glycerol acetal (trade name: Frescolat® MGA), menthyl lactate (trade name: Frescolat® ML, menthyl lactate is preferably l-menthyl lactate, in particular l-menthyl l-lactate), menthyl ethylamido oxalate (Frescolat® X-Cool), menthylethers (for example (l-menthoxy)-1,2-propandiol, (l-menthoxy)-2-methyl-1,2-propandiol, l-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxyl) acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, monomenthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^{\alpha}$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide

[WS23]), isopulegol or its esters (l-(−)-isopulegol, l-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

The use concentration of the active cooling compounds to be employed is, depending on the substance, preferably in the concentration range from 0.01% to 20% by weight, and more preferably in the concentration range from 0.1% to 5% by weight, based on the total weight of the completed (ready-to-use) cosmetic and pharmaceutical (dermatological) preparations The following examples are intended to illustrate the present invention without restricting it. All amounts quoted, proportions and percentages are, unless indicated otherwise, based on the weight and the total amount or on the total weight of the preparations.

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, - -isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation. It should be noted that the information on additives and their ranges for cosmetic compositions are also valid for pharmaceutical or dermatalogical formulations.

Anti-Irritation Agents

An important group of co-actives encompass anti-irritant agents such as for example steroidal anti-inflammatory substances of the corticosteroid type, such as e.g. hydrocortisone, hydrocortisone derivatives, such as hydrocortisone 17-butyrate, dexamethasone, dexamethasone phosphate, methylprednisolone or cortisone; non-steroidal anti-inflammatories like oxicams, such as piroxicam or tenoxicam; salicylates, such as aspirin, Disalcid, Solprin or fendosal; acetic acid derivatives, such as diclofenac, fenclofenac, indomethacin, sulindac, tolmetin or clindanac; fenamates, such as mefenamic, meclofenamic, flufenamic or niflumic; propionic acid derivatives, such as ibuprofen, naproxen or benoxaprofen, or pyrazoles, such as phenylbutazone, oxyphenylbutazone, febrazone or azapropazone. Alternatively, natural anti-inflammatory substances or reddening- and/or itching-alleviating substances can be employed. Plant extracts, specific highly active plant extract fractions and highly pure active substances isolated from plant extracts, can be employed like extracts, fractions and active substances from aloe vera, *Commiphora* species, *Rubia* species, *Rubus* species, willow, rose-bay, willowherb, oats, calendula, arnica, St. John's wort, honeysuckle, ginger, chamomile, rosemary, sage, melissa, *Passiflora incarnata, Sophora japonica*, witch hazel, *Pueraria, Dianthus* or *Echinacea*, as well as pure substances, such as, inter alia, bisabolol, apigenin, apigenin-7-glucoside, rosmarinic acid, boswellic acid, phytosterols, glycyrrhizic acid, glabridin, licochalcone A, [6]-paradol, and anthranilic acid amides, such as, in particular, avenanthramides or dianthramides, are particularly preferred. The total amount of anti-irritants in a formulation or product according to the invention is preferably in the range of from 0.0001 to 20 wt. %, preferably from 0.0001 to 10 wt. %, in particular from 0.001 to 5 wt. %, based on the total weight of the formulation or product, respectively.

Particular useful co-actives are selected from the group consisting of anti-mycotica and pain relief agents, and more particularly the group consisting of erythromycin, dimetindene, betamethasone, ibuprofen, ketoprofene, diclofenac, metronidazole, acyclovir, imiquimod, terbinafine, docosanol, cyclopyroxolamine, and their mixtures:

Erythromycin is a macrolide antibiotic that has an antimicrobial spectrum similar to or slightly wider than that of penicillin, and is often used for people who have an allergy to penicillin.

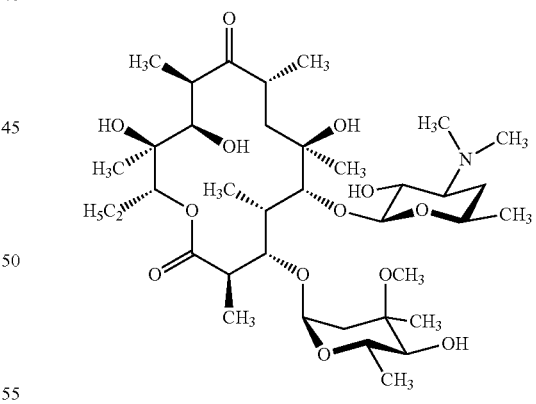

Recent studies have also shown that it can be used as a mild anti-depressant. For respiratory tract infections, it has better coverage of atypical organisms, including *Mycoplasma* and legionellosis. It was first marketed by Eli Lilly and Company, and it is today commonly known as EES (erythromycin ethylsuccinate, an ester prodrug that is commonly administered). In structure, this macrocyclic compound contains a 14-membered lactone ring with ten asymmetric centres and two sugars (L-cladinose and D-desosamine), making it a compound very difficult to produce via synthetic methods. Erythromycin is produced from a strain of the actinomycete *Saccharopolyspora erythraea* (see U.S. Pat. No. 2,653,899—Eli Lily).

Dimetindene, also known as Fenistil (RS-dimethyl(2-(3-[pyridin-2-yl)ethyl]-1H-inden-2-yl)ethyl)amine) is an antihistamine/anticholinergic used orally and locally as an antipruritic.

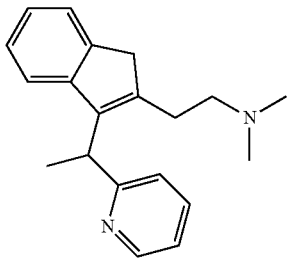 [SMILES: CC(C1=C(CCN(C)C)Cc2ccccc21)c1ccccn1]

Betamethasone (8S,9R,10S.11S,13S,14S,16S,17R)-9-fluoro-11,17-(2-hydroxyacetyl)-10,13,16-trimethyl-6,7,8,9,10,11,12,13,14,15,16,17-dodecahydro-3H-cyclopenta(alpha)-phenanthren-3-one) is a potent glucocorticoid steroid with anti-inflammatory and immunosuppressive properties.

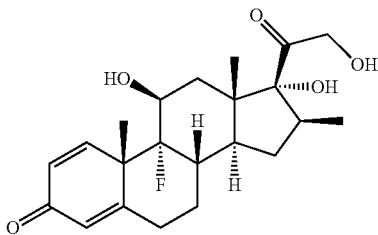

Unlike other drugs with these effects, betamethasone does not cause water retention. It is applied as a topical cream, ointment, foam, lotion or gel to treat itching. Betamethasone sodium phosphate is sometimes prescribed as an intramuscular injection (I.M) for itching from various ailments, including allergic reactions to poison ivy and similar plants (see U.S. Pat. No. 3,053,865—Merck).

Ibuprofen (RS)-2-(4-(2-methylpropyl)phenyl)propanoic acid) from the nomenclature iso-butyl-propanoic-phenolic acid) is a non-steroidal anti-inflammatory drug (NSAID) used for relief of symptoms of arthritis, fever, as an analgesic (pain reliever), especially where there is an inflammatory component, and dysmenorrhea.

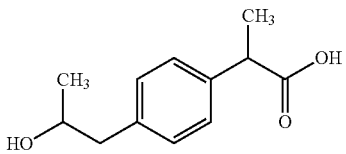

Ibuprofen is known to have an antiplatelet effect, though it is relatively mild and somewhat short-lived when compared with aspirin or other better-known antiplatelet drugs. In general, ibuprofen also acts as a vasoconstrictor, having been shown to constrict coronary arteries and some other blood vessels mainly because it inhibits the vasodilating prostacyclin produced by cyclooxygenase 2 enzymes. Ibuprofen was derived from propanoic acid by the research arm of Boots Group during the 1960s and was patented in 1961. Originally marketed as Brufen, ibuprofen is available under a variety of popular trademarks, including Motrin, Nurofen, Advil, and Nuprin (see U.S. Pat. No. 3,385,886—Boots).

Ketoprofen (RS)2-(3-benzoylphenyl)-propionic acid is another one of the propionic acid class of non-steroidal anti-inflammatory drug (NSAID) with analgesic and antipyretic effects.

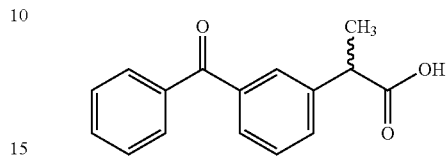

It acts by inhibiting the body's production of prostaglandins (see U.S. Pat. No. 3,641,127—Rhone-Poulenc).

Diclofenac is also a non-steroidal anti-inflammatory drug (NSAID) taken to reduce inflammation and as an analgesic reducing pain in certain conditions.

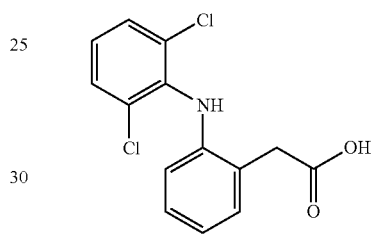

The name is derived from its chemical name: 2-(2,6-dichloranilino)phenylacetic acid. In the United Kingdom, India, Brazil and the United States, it may be supplied as either the sodium or potassium salt, in China most often as the sodium salt, while in some other countries only as the potassium salt. Diclofenac is available as a generic drug in a number of formulations. Over-the-counter (OTC) use is approved in some countries for minor aches and pains and fever associated with common infections (see U.S. Pat. No. 3,558,690—Ciba-Geigy).

Metronidazole (2-(2-methyl-5-nitro-1H-imidazol-1-yl) ethanol) is a nitroimidazole antibiotic medication used particularly for anaerobic bacteria and protozoa.

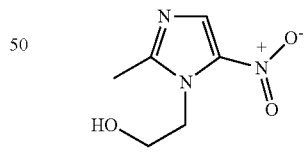

Metronidazole is an antibiotic, amebicide, and antiprotozoal. It is the drug of choice for first episodes of mild-to-moderate *Clostridium difficile* infection. It is marketed in the U.S.A. by Pfizer and globally by Sanofiunder the trade name Flagyl, in Pakistan and Bangladesh also as Nidagyl by Star Laboratories, and in Thailand, as Mepagyl by Thai Nakhorn Patana. It is also marketed in UK by Milpharm Limited and Almus Pharmaceuticals. Metronidazole was developed in 1960. Metronidazole is used also as a gel preparation in the treatment of the dermatological conditions such as rosaceae and fungating tumours (see U.S. Pat. No. 2,944,061—Rhone Poulenc).

(VIII) Acyclovir or acyclovir (USAN, former BAN), chemical name acycloguanosine (2-Amino-1,9-dihydro-9-((2-hydroxyethoxy)methyl)-6H-Purin-6-one), abbreviated as ACV is a guanosine analogue antiviral drug, marketed under trade names such as Cyclovir, Herpex, Acivir, Acivirax, Zovirax, and Xovir. The solid active agent has a solubility in water (20° dH) at 20° C. of less than 5 g/L.

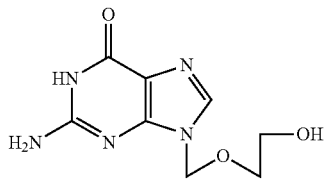 [SMILES: Nc1nc2c(ncn2COCCO)c(=O)[nH]1]

One of the most commonly used antiviral drugs; it is primarily used for the treatment of herpes simplex virus infections, as well as in the treatment of varicella zoster (chickenpox) and herpes zoster (shingles); see also U.S. Pat. No. 4,199,574 (Wellcome).

Imiquimod (3-(2-methylpropyl)-3,5,8-triazatricyclo[7.4.0.0.$^{2,6}$]trideca-1(9),2(6),4,7,10,12-hexaen-7-amine, INN) is a prescription medication that acts as an immune response modifier.

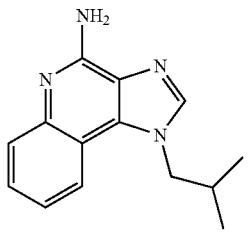 [SMILES: CC(C)Cn1cnc2c(N)nc3ccccc3c21]

It is marketed by Meda AB, Graceway Pharmaceuticals and iNova Pharmaceuticals under the trade names Aldara and Zyclara, and by Mochida as Beselna. It is also referred to as R-837 (see U.S. Pat. No. 4,689,338—Riker).

Terbinafine, more particularly terbinafine hydrochloride [(2E)-6,6-dimethylhept-2-en-4-yn-1-yl](methyl)(naphthalen-1-ylmethyl)amine) is a synthetic allylamine antifungal from Novartis. It is highly lipophilic in nature and tends to accumulate in skin, nails, and fatty tissues.

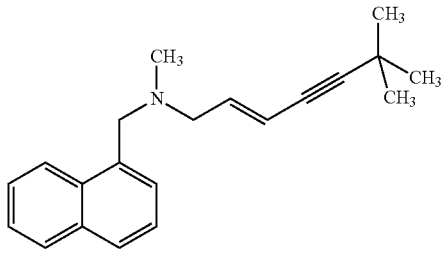 [SMILES: CN(C/C=C/C#CC(C)(C)C)Cc1cccc2ccccc12]

It is sold by the name Lamisil in Argentina, Australia, Belgium, Brazil, Canada, Chile, Egypt, Finland, France, Germany, Greece, Hungary, Iceland, Ireland, Israel, Mexico, Pakistan, Peru, New Zealand, Norway, Romania, Russia, Slovenia, South Africa, Sweden, United Kingdom, United States and Venezuela, also sold under the name Corbinal andTerbisil in Turkey and under the name "undofen cream" in Poland. As a generic it is sold under the name Zabel in Australia. It is also available as a generic medication in the United States, United Kingdom, Belgium, Switzerland and Brazil. In India, Terbinafine hydrochloride is available in topical form under the brand name Sebifin (Ranbaxy Labs), Zimig (GSK Pharma) and mycoCeaze (Progreś Laboratories). MycoVa, developed by Apricus Biosciences, is a topical nail solution of terbinafine and DDAIP which has completed three Phase III studies for the treatment of onychomycosis (see U.S. Pat. No. 4,755,534—Sandoz)

Docosanol, also known as behenyl alcohol, is a saturated fatty alcohol used traditionally as an emollient, emulsifier, and thickener in cosmetics, nutritional supplement (as an individual entity and also as a constituent of policosanol), and more recently, in a Food and Drug Administration (FDA) approved pharmaceutical, Abreva, approved as an antiviral agent for reducing the duration of cold sores caused by the herpes simplex virus.

Ciclopiroxolamine (6-cyclohexyl-1-hydroxy-4-methylpyridin-2(1H)-one) also called Batrafen, Loprox, Mycoster, Penlac and Stieprox, is a synthetic antifungal agent for topical dermatologic treatment of superficial mycoses.

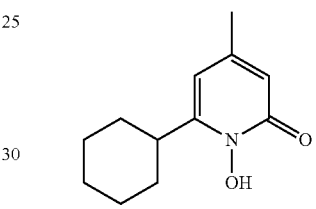

It is most useful against *Tinea versicolor* (see U.S. Pat. No. 3,883,545—Marck).

Anti-Cellulite Agents

Agents enhancing or boosting the activity of anti-cellulite agents, in particular agents which stimulate and/or depolarise C nerve fibres, are preferably selected from the group consisting of capsaicin and derivatives thereof, vanillylnonylamid and derivatives thereof, L-carnitine, coenzym A, isoflavonoides, soy extracts, ananas extract and conjugated linoleic acid.

Fat Enhancing Agents

Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D™).

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (*Leontodon* or *Taraxacum*), *Orthosiphon*, *Vitex*, *Coffea*, *Paullinia*, *Theobroma*, *Asiasarum*, *Cucurbita* or *Styphnolobium*, *Serenoa repens* (saw palmetto), *Sophora flavescens*, *Pygeum africanum*, *Panicum miliaceum*, *Cimicifuga racemosa*, *Glycine max*, *Eugenia caryophyllata*, *Cotinus coggygria*, *Hibiscus rosa-sinensis*, *Camellia sinensis*, *Ilex paraguariensis*, licorice, grape, apple, barley or hops or/nd hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus*, *Gloiopeltis*, *Ceramium*, *Durvillea*, *Glycine max*, *Sanguisorba officinalis*, *Calendula officinalis*, *Hamamelis virginiana*, *Arnica montana*, *Salix alba*, *Hypericum perforatum* or *Gymnema sylvestre*.

Solutes

Formulations and products according to the present invention may also comprise one or more compatible solutes. Preferred compatible solutes are such as described in WO 01/76572, particularly dimyo-inositol phosphate (DIP), diglycerin phosphate (DGP), di-myoinositol phosphate (DIP), cyclic 2,3 diphosphoglycerate (cDPG), 1,1-di-glycerol phosphate (DGP), beta-mannosyl glycerate (firoin), beta-mannosyl glyceramide (firoin-A) and dimannosyl-di-inositol phosphate (DMIP) and ectoine and ectoine-derivatives, as described in EP 0 553 884, EP 0 671 161 and WO 94/15923, in particular ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid).

Preferably, the total amount of compatible solutes is in the range of from 0.05 to 10 wt.-%, preferably from 0.1 to 5 wt.-%, based on the total weight of the formulation or product.

Solvents

The pharmaceutical compositions may contain such as for example aliphatic alcohols or 1,2-alkandiols or of course simply water.

1,2-Alkandiols. Suitable 1,2-alkandiols encompass 1,2-butadiol, 1,2-pentandiol, 1,2-hexandiol, 1,2-heptanddiol, 1,2-octandiol, 1,2-nonandiol, 1,2-decandiol, 1,2-undecandiol, 1,2,dodecandiol and their mixtures. The preferred 1,2-alkandiol is 1,2-pentandiol.

Aliphatic Alcohols. Suitable aliphatic alcohols are selected from the group consisting of ethanol, n-propanol, isopropylalcohol, the isomeric butanols and their mixtures. The preferred species is ethanol, in particular with a purity of at least 95%.

Pigments

Cosmetic and/or pharmaceutical preparations according to the present invention advantageously, but not obligatorily, comprise inorganic pigments based on finely disperse metal oxides and/or other metal compounds which are insoluble or sparingly soluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_1O_3$), cerium (e.g. $Ce_2O_3$), mixed oxides of the corresponding metals, and mixtures of such oxides. These pigments are X-ray-amorphous or non-X-ray-amorphous. X-ray-amorphous oxide pigments are metal oxides or semi-metal oxides which reveal no or no recognizable crystalline structure in X-ray diffraction experiments. Such pigments are often obtainable by flame reaction, for example by reacting a metal or semi-metal halide with hydrogen and air (or pure oxygen) in a flame.

In cosmetic and/or pharmaceutical preparations, X-ray-amorphous oxide pigments are used as thickeners and thixotropic agents, flow auxiliaries for emulsion and dispersion stabilization and as carrier substance (for example for increasing the volume of finely divided powders). X-ray-amorphous oxide pigments which are known and often used in cosmetic or dermatological galenics are, for example, high-purity silicon oxide. Preference is given to high-purity, X-ray-amorphous silicon dioxide pigments with a particle size in the range from 5 to 40 nm and an active surface area (BET) in the range from 50 to 400 $m^2/g$, preferably 150 to 300 $m^2/g$, where the particles are to be regarded as spherical particles of very uniform dimension. Macroscopically, the silicon dioxide pigments are recognizable as loose, white powders. Silicon dioxide pigments are sold commercially under the name Aerosil® (CAS-No. 7631-85-9) or Carb-O-Sil.

Advantageous Aerosil® grades are, for example, Aerosil® 0X50, Aerosil® 130, Aerosil® 150, Aerosil® 200, Aerosil® 300, Aerosil® 380, Aerosil® MQX 80, Aerosil® MOX 170, Aerosil® COK 84, Aerosil® R 202, Aerosil® R 805, Aerosil® R 812, Aerosil® R 972, Aerosil® R 974, Aerosil® R976.

According to the present invention, cosmetic and pharmacological preparations, preferably dermatological preparations comprise 0.1 to 20% by weight, advantageously 0.5 to 10% by weight, more preferably 1 to 5% by weight, of X-ray-amorphous oxide pigments.

The non-X-ray-amorphous inorganic pigments are, according to the present invention, advantageously in hydrophobic form, i.e. have been surface-treated to repel water. This surface treatment may involve providing the pigments with a thin hydrophobic layer by processes known per se. Such a process involves, for example, producing the hydrophobic surface layer by a reaction according to

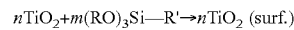

where n and m are stoichiometric parameters to be used as desired, and R and R' are the desired organic radicals. Hydrophobic pigments prepared analogously to DE-A 33 14 742, for example, are advantageous.

The total amount of inorganic pigments, in particular hydrophobic inorganic micro pigments, in the finished cosmetic and pharmacological preparations, particularly in dermatological preparations is advantageously chosen from the range from 0.1 to 30% by weight, preferably 0.1 to 10.0% by weight, preferably 0.5 to 6.0% by weight, based on the total weight of the preparations.

Skin Lightening Ingredients

An additional content of skin lightening ingredients in the cosmetic and pharmacological preparations, preferably dermatological preparations is optional. Such skin lightening ingredients which can be used are for example but not limited to the following: kojic acid (5-hydroxy-2-hydroxymethyl-4-pyranone), kojic acid derivatives such as for example kojic dipalmitate, arbutin, ascorbic acid, ascorbic acid derivatives, hydroquinone, hydroquinone derivatives, styryl resorcinol derivatives (e.g. 4-(1-phenylethyl)1,3-benzenediol), molecules containing sulphur, such as glutathione or cysteine for example, alpha-hydroxy acids (e.g. citric acid, lactic acid, malic acid) and their derivatives, N-acetyl-tyrosine and derivatives, undecenoylphenylalanine, gluconic acid, chromone derivatives such as aloesin, flavonoids, thymol derivatives, 1-aminoethylphosphinic acid, thiourea derivatives, ellagic acid, nicotinamide, zinc salts such as zinc chloride or zinc gluconate for example, thujaplicin and derivatives, triterpenes such as maslic acid, sterols such as ergosterol, benzofuranones such as senkyunolide, vinyl- and ethylguaiacol, dionic acids such as octodecenedionic acid and azelaic acid, nitrogen oxide synthesis inhibitors such as L-nitroarginine and its derivatives, 2,7-dinitroindazole or thiocitrulline, metal chelators (e.g. alphahydroxy fatty acids, palmitic acid, phytic acid, lactoferrin, humic acid, gallic acid, bile extracts, bilirubin, biliverdin), retinoids, soja milk, soya extract, serine protease inhibitors or lipoic acid or other synthetic or natural active compounds for skin and hair lightening, these compounds also being used in the form of an extract from plants, such as bearberry extract, rice extract, papaya extract, liquorice root extract or constituents concentrated from these, such as glabridin or licochalcone A, *Artocarpus* extract, extract from *Rumex* and *Ramulus* species, extracts from pine species (*Pinus*) and extracts from *Vitis* species or stilbene derivatives concentrated from these, extract from saxifraga, mulberry, *Scutelleria* and/or grapes.

Antioxidants

An additional content of antioxidants in the cosmetic and pharmacological preparations, preferably dermatological preparations is generally preferred. According to the present invention, favorable antioxidants which can be used are all antioxidants customary or suitable for the cosmetic and pharmacological preparations, preferably dermatological preparations. The antioxidants are advantageously chosen from the group of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, (β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cysteine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides, and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, maleic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxy-toluene, butylhydroxyanisol, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids), derivatives of acetophenone such as Hydroxyacetophenone and its blends with Phenoxyethanol and/or, pentane 1,2 diol and/or hexane 1,2 diol and/or caprylyl 1,2 diol, are suitable according to the present invention.

The amount of the above-mentioned antioxidants (one or more compounds) in the preparations is preferably 0.001 to 30% by weight, more preferably 0.05 to 20% by weight, and most preferably 1 to 10% by weight, based on the total weight of the preparation.

Vitamins

Preferred embodiments of the cosmetic and pharmacological preparations, preferably dermatological preparations of the invention may advantageously also comprise vitamins and vitamin precursors, it being possible for all the vitamins and vitamin precursors which are suitable or usual for cosmetic and pharmacological preparations, especially dermatological preparations to be used. Those worth mentioning here are, in particular, vitamins and vitamin precursors, such as tocopherols, vitamin A, niacin acid and niacinamide, further vitamins of the B complex, in particular biotin, and vitamin C and panthenol and derivatives thereof, in particular the esters and ethers of panthenol, and cationically derivatized panthenols, such as panthenol triacetate, panthenol monoethyl ether and the monoacetate thereof and cationic panthenol derivatives. If vitamin E and/or derivatives thereof represent the antioxidant(s), it is advantageous to choose their respective concentrations from the range from 0.001 to 10% by weight, based on the total weight of the formulation. If vitamin A or vitamin A derivatives, or carotenes or derivatives thereof represent the antioxidant(s), it is advantageous to choose their respective concentrations from the range from 0.001 to 10% by weight, based on the total weight of the formulation.

Lipids

Preferred embodiments of the cosmetic and pharmacological preparations, especially dermatological preparations of the invention may also comprise lipids chosen from the following group of substances:

(i) linear or branched saturated paraffins (mineral oils) having 15 or more C atoms, in particular having 18 to 45 C atoms;

(ii) esters having 12 or more C atoms of linear or branched fatty acids having 6 to 30 C atoms and linear or branched, saturated or unsaturated mono-, di- or triols having 3 to 30 C atoms, these esters having no free hydroxyl groups;

(iii) esters of benzoic acid and linear or branched, saturated or unsaturated monoalkanols having 8 to 20 C atoms;
(iv) monoesters or diesters of alcohols having 3 to 30 C atoms and naphthalenemonocarboxylic or -dicarboxylic acids; especially naphthalenemonocarboxylic acid $C_6$-$C_{18}$ esters and naphthalenedicarboxylic acid di-$C_6$-$C_{18}$ esters;
(v) linear or branched, saturated or unsaturated di-$C_6$-$C_{18}$-alkyl ethers;
(vi) silicone oils;
(vii) 2-alkyl-1-alkanols of the formula (III)

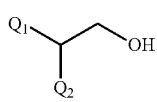

(III)

where
$Q_1$ is a linear or branched alkyl radical having 6 to 24 C atoms and
$Q_2$ is a linear or branched alkyl radical having 4 to 16 C atoms.

Ingredients Having Care Properties

Preferred embodiments of the cosmetic and pharmacological preparations, especially dermatological preparations of the invention comprise, if desired, further ingredients having care properties, such as, for example, fatty alcohols having 6 to 30 C atoms. The fatty alcohols here can be saturated or unsaturated and linear or branched. Furthermore, these fatty alcohols can in some cases be part of the oil phase (III) if they correspond to the definition given there. Alcohols which can be employed are, for example, decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, caprylyl alcohol, capryl alcohol, linoleyl alcohol, linolenyl alcohol and behenyl alcohol, and also Guerbet alcohols thereof, such as, for example, 2-octyl-1-dodecanol, it being possible for the list to be extended virtually as desired by further alcohols of related structural chemistry. The fatty alcohols preferably originate from natural fatty acids, being conventionally prepared from the corresponding esters of the fatty acids by reduction. Fatty alcohol fractions which are formed by reduction from naturally occurring fats and fatty oils, such as beef tallow, peanut oil, colza oil, cottonseed oil, soya oil, sunflower oil, palm kernel oil, linseed oil, maize oil, castor oil, rapeseed oil, sesame oil, cacao butter and coconut fat, can further be employed.

Substances having care properties which advantageously can be employed in the cosmetic and pharmacological preparations, especially dermatological preparations can further include
ceramides, where ceramides are understood as meaning N-acylsphingosins (fatty acid amides of sphingosin) or synthetic analogues of such lipids (so-called pseudoceramides), which significantly improve the water retention capacity of the stratum corneum.
phospholipids, for example soya lecithin, egg lecithin and cephalins
fatty acids
phytosterols and phytosterol-containing fats or waxes
vaseline, paraffin oils and silicone oils; the latter include, inter alia, dialkyl- and alkylarylsiloxanes, such as dimethylpolysiloxane and methylphenylpolysiloxane, and also alkoxylated and quaternised derivatives thereof.

Alcohols

The aqueous phase of the preparations according to the present invention optionally advantageously comprises alcohols, diols or polyols (lower alkyl), and ethers thereof, preferably ethanol, isopropanol, propylene glycol, 1,2-pentane diol, 1,2-hexanediol, 1,2-octanediol, 1,2-decanediol, a mixture of 1,2-hexanediol and 1,2-octanediol, a mixture of 1,2-hexanediol and 1,2-decanediol, a mixture of 1,2-octanediol and 1,2-decanediol, a mixture of 1,2-hexanediol, 1,2-octanediol and 1,2-decanediol, glycerol, ethylene glycol-monoethyl or monobutyl ether, propylene glycol monomethyl, -monoethyl or monobutyl ether, diethylene glycol monomethyl or -monoethyl ether and analogous products, and also alcohols (lower alkyl), e.g. ethanol, 1,2-propanediol, glycerol, and, in particular, one or more thickeners which can advantageously be chosen from the group of silicon dioxide, aluminum silicates, polysaccharides and derivatives thereof, e.g. hyaluronic acid, xanthan gum, hydroxypropylmethylcellulose, particularly advantageously from the group of polyacrylates, preferably a polyacrylate from the group of so-called Carbomers, for example but not limited to, Carbopol® grades 980, 981, 1382, 2984, 5984, in each case individually or in combination.

Anti-Inflammatory Compounds

Preferred embodiments of the cosmetic and pharmacological preparations, especially dermatological preparations of the invention may also comprise active anti-inflammatory and/or redness- and/or itching-alleviating compounds (anti-irritants). All the active anti-inflammatory or redness- and/or itching-alleviating compounds which are suitable or usual for cosmetic, dermatological and pharmacological preparations can be used here. Active anti-inflammatory and redness- and/or itching-alleviating compounds which are advantageously employed are steroidal anti-inflammatory substances of the corticosteroid type, such as hydrocortisone, dexamethasone, dexamethasone phosphate, methylprednisolone or cortisone, it being possible for the list to be extended by addition of further steroidal anti-inflammatories. Non-steroidal anti-inflammatories can also be employed. Those to be mentioned here by way of example are oxicams, such as piroxicam or tenoxicam; salicylates, such as aspirin, Disalcid, Solprin or fendosal; acetic acid derivatives, such as diclofenac, fenclofenac, indomethacin, sulindac, tolmetin, or clindanac; fenamates, such as mefenamic, meclofenamic, flufenamic or niflumic; propionic acid derivatives, such as ibuprofen, naproxen, benoxaprofen or pyrazoles, such as phenylbutazone, oxyphenylbutazone, febrazone or azapropazone.

Alternatively, natural anti-inflammatory or redness- and/or itching-alleviating substances can be employed. Plant extracts, specific highly active plant extract fractions and highly pure active substances isolated from plant extracts can be employed. Extracts, fractions and active substances from chamomile, aloe vera, *Commiphora* species, *Rubia* species, willow, rose-bay willow-herb, oats, and also pure substances, such as, inter alia, bisabolol, apigenin 7-glucoside, boswellic acid, phytosterols, glycyrrhizic acid, glabridin or licochalcone A, are particularly preferred. The preparations of the present invention can also comprise mixtures of two or more active anti-inflammatory compounds. Bisabolol, boswellic acid, and also extracts and isolated highly pure active compounds from oats and *Echinacea* are particularly preferred for use in the context of the invention as anti-inflammatory and redness- and/or itching-alleviating substances, and alpha-bisabolol and extracts and isolated highly pure active compounds from oats are especially preferred.

The amount of anti-irritants (one or more compounds) in the preparations is preferably 0.0001% to 20% by weight, with particular preference 0.0001% to 10% by weight, in particular 0.001% to 5% by weight, based on the total weight of the preparation.

Moisture Regulator

Preferred embodiments of the cosmetic and pharmacological preparations, especially dermatological preparations of the invention may advantageously also comprise moisture retention regulators. The following substances for example are used as moisture retention regulators (moisturizers): sodium lactate, urea, alcohols, sorbitol, glycerol, propylene glycol, aliphatic 1,2-diols with a C number of 5-10, collagen, elastin or hyaluronic acid, diacyl adipates, petrolatum, ectoin, urocanic acid, lecithin, panthenol, phytantriol, lycopene, algae extract, ceramides, cholesterol, glycolipids, chitosan, chondroitin sulphate, polyamino acids and polyamino sugars, lanolin, lanolin esters, amino acids, alpha-hydroxy acids (e.g. citric acid, lactic acid, malic acid) and derivatives thereof, sugars (e.g. inositol), alpha-hydroxy fatty acids, phytosterols, triterpene acids, such as betulinic acid or ursolic acid, algae extracts.

Plant Extracts

Preferred embodiments of the cosmetic and pharmacological preparations, especially dermatological preparations of the invention may advantageously also comprise plant extracts, which are conventionally prepared by extraction of the whole plant, but also in individual cases exclusively from blossom and/or leaves, wood, bark or roots of the plant. In respect of the plant extracts which can be used, reference is made in particular to the extracts which are listed in the table starting on page 44 of the 3rd edition of the Leitfaden zur Inhaltsstoffdeklaration kosmetischer Mittel [Manual of Declaration of the Constituents of Cosmetic Compositions], published by Industrieverband Körperpflegemittel and Waschmittel e.V. (IKW), Frankfurt. Extracts which are advantageous in particular are those from aloe, witch hazel, algae, oak bark, rose-bay willow-herb, stinging nettle, dead nettle, hops, chamomile, yarrow, arnica, calendula, burdock root, horsetail, hawthorn, linden blossom, almond, pine needle, horse chestnut, sandalwood, juniper, coconut, mango, apricot, orange, lemon, lime, grapefruit, apple, green tea, grapefruit pip, wheat, oats, barley, sage, thyme, wild thyme, rosemary, birch, mallow, lady's smock, willow bark, restharrow, coltsfoot, hibiscus, ginseng and ginger root.

In this context, the extracts from aloe vera, chamomile, algae, rosemary, calendula, ginseng, cucumber, sage, stinging nettle, linden blossom, arnica and witch hazel are particularly preferred. Mixtures of two or more plant extracts can also be employed. Extraction agents which can be used for the preparation of plant extracts mentioned are, inter alia, water, alcohols and mixtures thereof. In this context, among the alcohols lower alcohols, such as ethanol and isopropanol, but also polyhydric alcohols, such as ethylene glycol, propylene glycol and butylene glycol, are preferred, and in particular both as the sole extraction agent and in mixtures with water. The plant extracts can be employed both in pure and in diluted form.

ILLUSTRATION OF THE INVENTION BY FIGS. 1 TO 4

The present invention is explained in more details by the following working examples, but also by the FIGS. 1 to 4:

FIG. 1: Photographs of residual whitening on the skin after application of 2.5 mg/cm2 of commercial sunscreen formulations vs. a laboratory made formulation containing 4% of a titanium dioxide coated with cetearyl nonoanoate, according to the invention, which have been rubbed into the skin for 15 seconds.

Figure 2:
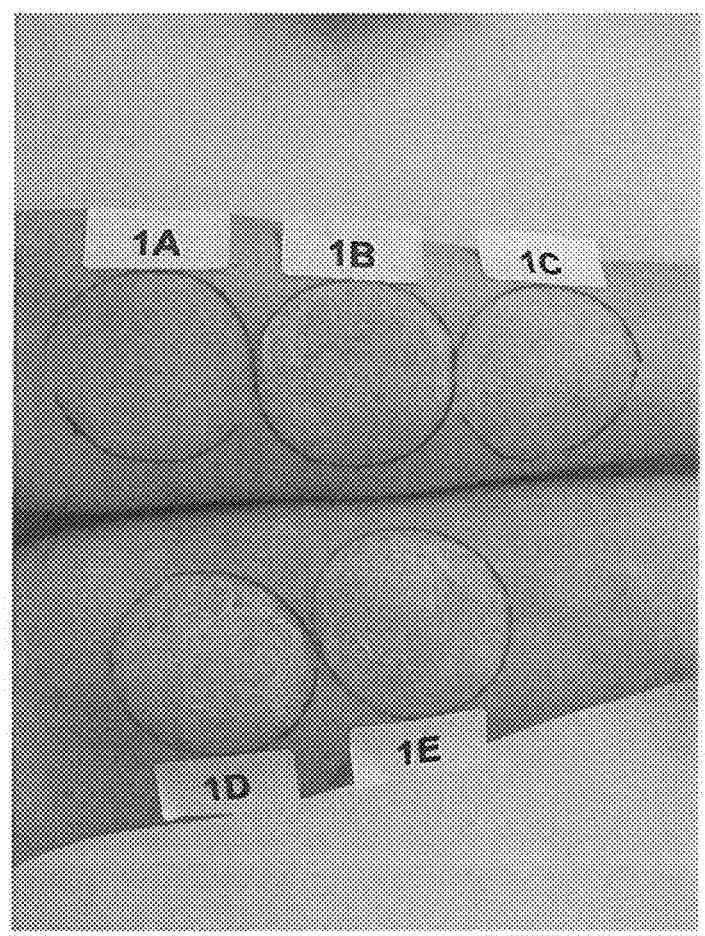
FIG. 2 is a photograph of residual whitening on the skin after application of 2.5 mg/cm2 of lotions each containing 4% of leading commercially available grades of titanium dioxide used for cosmetic, dermatological and pharmacological preparations for the protection of human skin against the harmful effects of UV radiation vs. a laboratory made formulation containing 4% of a titanium dioxide coated with cetearyl nonoanoate, according to the invention, which have been rubbed into the skin for 15 seconds.

FIG. 2: Photographs of residual whitening on the skin after application of 2.5 mg/cm2 of lotions each containing 4% of leading commercially available grades of titanium dioxide used for cosmetic, dermatologocal and pharmacological preparations for the protection of human skin against the harmful effects of UV radiation vs. a laboratory made formulation containing 4% of a titanium dioxide coated with cetearyl nonoanoate, according to the invention, which have been rubbed into the skin for 15 seconds.

Figure 3:
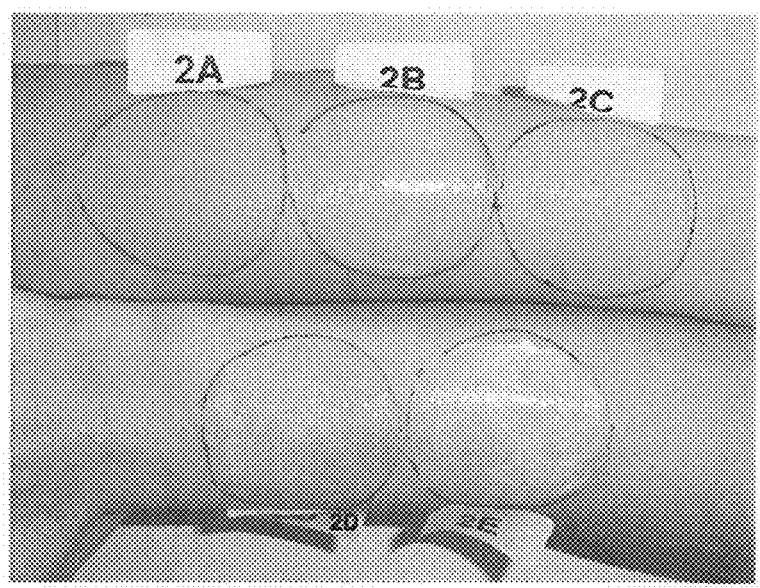
FIG. 3 is a photograph of residual whitening on the skin after application of 2.5 mg/cm2 of sprays, each containing 4% of leading commercially available grades of titanium dioxide used for cosmetic, dermatological and pharmacological preparations for the protection of human skin against the harmful effects of UV radiation vs. a laboratory made formulation containing 4% of a titanium dioxide coated with cetearyl nonoanoate, according to the invention, which have been rubbed into the skin for 15 seconds.

FIG. 3: Photographs of residual whitening on the skin after application of 2.5 mg/cm2 of sprays, each containing 4% of leading commercially available grades of titanium dioxide used for cosmetic, dermatologocal and pharmacological preparations for the protection of human skin against the harmful effects of UV radiation vs. a laboratory made formulation containing 4% of a titanium dioxide coated with cetearyl nonoanoate, according to the invention, which have been rubbed into the skin for 15 seconds.

Figure 4:
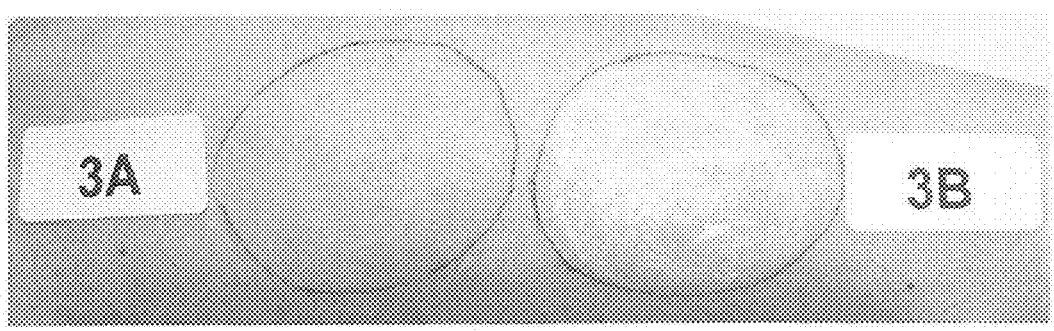
FIG. 4 is a photograph of residual whitening on the skin after application of 2.5 mg/cm2 of lotions which have been rubbed into the skin for 15 seconds, one containing 4% of a titanium dioxide coated with cetearyl nonoanoate, according to the invention, the other containing the same grade of titanium dioxide but without the coating of cetearyl nonanoate, in which 4% of cetearyl nonanoate had been added to the lotion separately.

FIG. 4: Photographs of residual whitening on the skin after application of 2.5 mg/cm2 of lotions which have been rubbed into the skin for 15 seconds, one containing containing 4% of a titanium dioxide coated with cetearyl nonoanoate, according to the invention, the other containing the same grade of titanium dioxide but without the coating of cetearyl nonanoate, in which 4% of cetearyl nonanoate had been added to the lotion separately.

EXAMPLES

Comparative Examples

Residual Whitening of Skin after Product Application

To illustrate the extent of the residual whitening left by formulations containing nano grades of titanium dioxide on human skin we applied 2.5 mg/cm2 of market leading commercially available sunscreens to the volar forearm covering a surface area 18 square centimeter and rubbed into the skin with one finger using the same pressure and speed for 15 seconds. Photographs were taken to show the residual whiteness of the formulation left on the skin's surface vs. a laboratory made formulation containing 4% of titanium dioxide coated with cetearyl nonoanoate. As the ingredients of cosmetic formulations have to be listed in the label of the finished product in decreasing order by weight by law in most countries, an experienced formulator can estimate approximately the percentage by weight the ingredient is present in the formulation.

The photographs in FIG. 1 show that the formulation with 4% titanium dioxide coated with cetearyl nonoanoate had significantly less residual whitening on the skin than the commercially available formulations in which it is estimated that they contain from 1-2% or 3-4% of nano titanium dioxide respectively.

To have a more direct comparison to discount formulation variability in as a cause of the residual whitening, we prepared formulations in which all ingredients are identical except the grade of nano titanium dioxide used in a single variable study with leading commercially available grades of titanium dioxide used in cosmetic, dermatological and pharmacological preparations for protection of the human skin against the harmful effects of UV radiation. Two common types of formulation were chosen a lotion and a spray.

Examples According to the Invention

Example 1

Sunscreen Lotion (OW), Expected SPF 30

Prepare phase A without Keltrol, TiO2 and heat to 85° C. Add TiO2 and Keltrol and homogenise for a short time with an Ultra Turrax®. Prepare phase B and heat up to 85° C. until homogeneous. Add phase B to phase A without stirring. Cool with stirring to 60° C., then homogenise with the Ultra Turrax. Add Phase C and cool down to ambient T with stirring until homogeneous and then homogenise for a short time with an Ultra Turrax®. Check the pH, if necessary adjust to 6.5.

The photographs in FIG. 2 show that the formulation with titanium dioxide coated with cetearyl nonanoate (A) had significantly less residual whitening on the skin than the formulations made with commercially available grades of titanium dioxide, except for competitive product C but this formula was more dull and had a much blunter feel on the skin than formula A. Formulation examples are provided in Table 1.

Example 2

Sunscreen Spray (O/W), Expected SPF 50+

Prepare phase A without TiO2, Pemulen and heat to 50° C. Add TiO2 and Pemulen, homogenise for 30 s with an Ultra Turrax®. Add the ingredients of phase B together and add to phase A without stirring then homogenise with the Ultra Turrax®. Then and phase C at ambient temperature with light stirring. The pH should be 6.5

The photographs in FIG. 3 show that the formulation with titanium dioxide coated with cetearyl nonanoate (A) had significantly less residual whitening on the skin than the formulations B, D and E made with commercially available grades of titanium dioxide, and while formulation C made with commercially available grade of titanium dioxide have a similar reduced whitening to formula A, but is much more glossy and had a much blunter feel on the skin than A. It is known that cetearyl nonanoate, when added as a separate ingredient to emulsions containing titanium dioxide reduces to some extent the whitening on skin (Symrise technical bulletin—SymMollient® S Quick Sheet). To show that titanium dioxide coated with cetearyl nonoate has a reduced whitening effect compared to non-cetearyl nonanoate titanium dioxide we prepared an emulsion with 4% of titanium dioxide plus 4% of cetearyl nonanaote added separately and an emulsion with 4% of the same grade of titanium dioxide which it had been coated with cetearly nonanoate. Formulation examples are provided in Table 2.

TABLE 1

O/W sunscreen formulation (All amounts in % w/w)

| Phase | Raw materials | INCI name | A | B | C | D | E |
|---|---|---|---|---|---|---|---|
| A | Emulsiphos ® | Potassium Cetyl Phosphate, Hydrogenated-Palm Glycerides | 2.00 | 2.00 | 2.00 | 2.00 | 2.00 |
|  | Lanette ® 16 | Cetyl Alcohol | 1.00 | 1.00 | 1.00 | 1.00 | 1.00 |
|  | Neo Heliopan ® 357 | Butyl Methoxydibenzoyl-methane | 3.00 | 3.00 | 3.00 | 3.00 | 3.00 |
|  | Neo Heliopan ® OS | Ethylhexyl Salicylate | 5.00 | 5.00 | 5.00 | 5.00 | 5.00 |
|  | Neo Heliopan ® 303 | Octocrylene | 8.00 | 8.00 | 8.00 | 8.00 | 8.00 |
|  | Neo Heliopan ® HMS | Homosalate | 5.00 | 5.00 | 5.00 | 5.00 | 5.00 |
|  | Dragoxat ® 89 | Ethylhexyl Isononanoate | 5.00 | 5.00 | 5.00 | 5.00 | 5.00 |
|  | KF-995 | Cyclopentasiloxane | 2.00 | 2.00 | 2.00 | 2.00 | 2.00 |
|  | EDETA ® BD | Disodium EDTA | 0.10 | 0.10 | 0.10 | 0.10 | 0.10 |
|  | Vitamin E Acetate | Tocopheryl Acetete | 0.50 | 0.50 | 0.50 | 0.50 | 0.50 |
|  | Keltrol ® T | Xanthan Gum | 0.50 | 0.50 | 0.50 | 0.50 | 0.50 |
|  | Titanium Dioxide according to the invention | Titanium Dioxide, Aluminum Hydroxide, Cetearyl Nonanoate, Stearic Acid | 4.00 |  |  |  |  |
|  | Commercial Titanium Dioxide coated with silica and dimethicone | Titanium Dioxide, Silica, Dimethicone |  | 4.00 |  |  |  |
|  | Commercial Titanium Dioxide coated with silica | Titanium Dioxide, Silica |  |  | 4.00 |  |  |
|  | Commercial 55% dispersion of Titanium Dioxide coated with Polyhydroxystearic Acid, Stearic Acid, Alumina in C12-15 Alkyl Benzoate, | Titanium Dioxide, Silica, C12-15 Alkyl Benzoate, Polyhydroxystearic Acid, Stearic Acid, Alumina |  |  |  | 7.27 |  |
| B | Commercial 50% aqueous dispersion of Titanium Dioxide coated with Stearic Acid, Alumina, | Titanium Dioxide, Water, Polyglyceryl-2 Caprate, Sucrose Stearate, *Simmondsia Chinensis* (Jojoba) Seed Oil, Stearic Acid, Alumina, Glyceryl Caprylate, Squalane |  |  |  |  | 8.00 |
|  | Water dem | Aqua (Water) | 52.05 | 52.05 | 52.05 | 49.23 | 42.05 |
|  | Troxerutin | Troxerutin | 0.30 | 0.30 | 0.30 | 0.30 | 0.30 |
|  | Neo Heliopan ® AP 106796, 15% neutralised with Biotive ® Arginin | Water, Disodium Phenyl Dibenzimidazole Tetrasulfonate, Arginine, | 6.70 | 6.70 | 6.70 | 6.70 | 6.70 |
|  | Glycerin 99% | Glycerin | 3.00 | 3.00 | 3.00 | 3.00 | 3.00 |
|  | Phenonip ® XB | Phenoxyethanol, Methylparaben, Ethylparaben, Propylparaben | 0.80 | 0.80 | 0.80 | 0.80 | 0.80 |
|  | Lanette ® E | Sodium Cetearyl Sulfate | 0.75 | 0.75 | 0.75 | 0.75 | 0.75 |
| C | Fragrance | Parfum | 0.20 | 0.20 | 0.20 | 0.20 | 0.20 |
|  | α-Bisabolol | Bisabolol | 0.10 | 0.10 | 0.10 | 0.10 | 0.10 |

TABLE 2

O/W sunscreen formulation (All amounts in % w/w)

| PHase | Raw materials | INCI name | A | B | C | D | E |
|---|---|---|---|---|---|---|---|
| A | Dracorin GOC | Glyceryl Oleate Citrate, Caprylic/Capric Triglyceride | 2.00 | 2.00 | 2.00 | 2.00 | 2.00 |
|  | PCL-Liquid 100 | Cetearyl Ethylhexanoate | 2.50 | 2.50 | 2.50 | 2.50 | 2.50 |
|  | Wacker Belsil CDM 3526 VP | C26-28 Alkyl Dimethicone | 1.00 | 1.00 | 1.00 | 1.00 | 1.00 |
|  | KF-995 | Cyclopentasiloxane | 1.00 | 1.00 | 1.00 | 1.00 | 1.00 |
|  | Edeta BD | Disodium EDTA | 0.10 | 0.10 | 0.10 | 0.10 | 0.10 |
|  | Vitamin E Acetat | Tocopheryl Acetate | 0.50 | 0.50 | 0.50 | 0.50 | 0.50 |
|  | Silcare Silicone 41M65 | Stearyl Dimethicone | 1.00 | 1.00 | 1.00 | 1.00 | 1.00 |
|  | SF 1550 | Phenyl Trimethicone | 1.00 | 1.00 | 1.00 | 1.00 | 1.00 |
|  | Alpha-Bisabolol | Bisabolol | 0.10 | 0.10 | 0.10 | 0.10 | 0.10 |
|  | Neo Heliopan ® E1000 | Isoamyl Methoxycinnamate | 2.00 | 2.00 | 2.00 | 2.00 | 2.00 |
| A | Neo Heliopan HMS | Homosalate | 10.00 | 10.00 | 10.00 | 10.00 | 10.00 |
|  | Neo Heliopan 303 | Octocrylene | 10.00 | 10.00 | 10.00 | 10.00 | 10.00 |
|  | Neo Heliopan OS | Ethylhexyl Salicylate | 5.00 | 5.00 | 5.00 | 5.00 | 5.00 |
|  | Neo Heliopan 357 | Butyl Methoxydibenzoylmethane | 5.00 | 5.00 | 5.00 | 5.00 | 5.00 |
|  | Tinosorb S | Bis-Ethylhexyloxyphenol Methoxyphenol Triazine | 1.00 | 1.00 | 1.00 | 1.00 | 1.00 |
|  | Titanium Dioxide according to the invention | Titanium Dioxide, Aluminum Hydroxide, Cetearyl Nonanoate, Stearic Acid | 3.00 |  |  |  |  |
|  | Commercial Titanium Dioxide coated with silica and dimethicone | Titanium Dioxide, Silica, Dimethicone |  | 3.00 |  |  |  |
|  | Commercial Titanium Dioxide coated with silica | Titanium Dioxide, Silica |  |  | 3.00 |  |  |
|  | Commercial Titanium Dioxide coated with aluminium hydroxid and stearic acid. | Titanium Dioxide, Stearic Acid, Aluminium Hydroxide |  |  |  | 3.00 |  |
|  | Commercial 55% dispersion of Titanium Dioxide coated with Polyhydroxystearic Acid, Stearic Acid, Alumina in C12-15 Alkyl Benzoate. | Titanium Dioxide, Silica, C12-15 Alkyl Benzoate, Polyhydroxystearic Acid, Stearic Acid, Alumina |  |  |  |  | 5.45 |
|  | Pemulen TR 2 | Acrylates/C10-30 Acrylates Co-polymer | 0.25 | 0.25 | 0.25 | 0.25 | 0.25 |
| B | Deion. Wasser | Water (Aqua) | 45.15 | 45.15 | 45.15 | 45.15 | 42.70 |
|  | Lanette E | Sodium Cetearyl Sulfate | 0.50 | 0.50 | 0.50 | 0.50 | 0.50 |
|  | Glycerin 99% | Glycerin | 3.00 | 3.00 | 3.00 | 3.00 | 3.00 |
|  | Neo Heliopan Hydro | Phenylbenzimidazole Sulfonic Acid | 2.00 | 2.00 | 2.00 | 2.00 | 2.00 |
|  | Biotive L-Arginine | Arginine | 1.00 | 1.00 | 1.00 | 1.00 | 1.00 |
|  | NaOH 10% | Sodium Hydroxide | 1.70 | 1.70 | 1.70 | 1.70 | 1.70 |
| C | Fragrance | Parfum | 0.20 | 0.20 | 0.20 | 0.20 | 0.20 |
|  | Symdiol 68 | 1,2 Hexanediol, Caprylylglycol | 1.00 | 1.00 | 1.00 | 1.00 | 1.00 |

Example 3

Sunscreen Lotion (O/W)

Prepare Phase A without Keltrol, TiO2 and heat to 85° C. Add TiO2 and Keltrol and homogenise for a short time with an Ultra Turrax®. Prepare phase B and heat up to 85° C. until homogeneous. Add phase B to phase A without stirring. Cool with stirring to 60° C., then homogenise with the Ultra Turrax. Add Phase C and cool down to ambient T with stirring until homogeneous and then homogenise for a short time with an Ultra Turrax®. Check the pH, if necessary adjust to 6.5.

The photographs in FIG. 4 show that the formulation with titanium dioxide coated with cetearyl nonanoate (A) had significantly less residual whitening on the skin than the formulations made with the cetearyl nonoate added separately (B). Formulation examples are provided in Table 3.

TABLE 3

O/W sunscreen formulation (All amounts in % w/w)

| Part | Raw materials | INCI name | A | B |
|---|---|---|---|---|
| A | Emulsiphos ® | Potassium Cetyl Phosphate, Hydrogenated Palm Glycerides | 2.00 | 2.00 |
|  | Lanette ® 16 | Cetyl Alcohol | 1.00 | 1.00 |
|  | Neo Heliopan ® 357 | Butyl Methoxydibenzoylmethane | 3.00 | 3.00 |
|  | Neo Heliopan ® OS | Ethylhexyl Salicylate | 5.00 | 5.00 |
|  | Neo Heliopan ® 303 | Octocrylene | 8.00 | 8.00 |
|  | Neo Heliopan ® HMS | Homosalate | 5.00 | 5.00 |
|  | Dragoxat ® 89 | Ethylhexyl Isononanoate | 5.00 | 5.00 |
|  | KF-995 | Cyclopentasiloxane | 2.00 | 2.00 |
|  | EDETA ® BD | Disodium EDTA | 0.10 | 0.10 |
|  | Vitamin E Acetate | Tocopheryl Acetete | 0.50 | 0.50 |
|  | Keltrol ® T | Xanthan Gum | 0.50 | 0.50 |

TABLE 3-continued

O/W sunscreen formulation (All amounts in % w/w)

| Part | Raw materials | INCI name | A | B |
|---|---|---|---|---|
| | Titanium Dioxide according to the invention | Titanium Dioxide, Aluminum Hydroxide, Cetearyl Nonanoate, Stearic Acid | 4.00 | |
| | Titanium Dioxide coated with Aluminum Hydroxide, Stearic Acid | Titanium Dioxide, Aluminum Hydroxide, Stearic Acid | | 4.00 |
| | SymMollient ® S | Cetearyl Nonanoate | | 4.00 |
| B | Water dem | Aqua (Water) | 52.05 | 48.05 |
| | Troxerutin | Troxerutin | 0.30 | 0.30 |
| | Neo Heliopan ® AP 106796, 15% neutralised with Biotive ® Arginin | Water, Disodium Phenyl Dibenzimidazole Tetrasulfonate, Arginine, | 6.70 | 6.70 |
| | Glycerin 99% | Glycerin | 3.00 | 3.00 |
| | Phenonip ® XB | Phenoxyethanol, Methylparaben, Ethylparaben, Propylparaben | 0.80 | 0.80 |
| | Lanette ® E | Sodium Cetearyl Sulfate | 0.75 | 0.75 |
| C | Fragrance | Parfum | 0.20 | 0.20 |
| | α-Bisabolol | Bisabolol | 0.10 | 0.10 |

Formulation Examples

Example 4

Sunscreen Lotion (O/W), Expected SPF 50+

Manufacturing: Phase A: Heat up to approx. 85° C. without Keltrol® and Titanium Dioxide, when all ingredients are dissolved add Keltrol® and Titanium Dioxide and homogenize with an Ultra Turrax® for a short time. Phase B: At first add the water then add the neutralisation agent Biotive® L-Arginine and the sodium hydroxide solution. Stir until homogeneous. Add the Neo Heliopan® Hydroand stir until all is dissolved. Add the rest of ingredients without Dragocolor to phase B and heat up to approx 80° C., add Dragocolor and homogenize for a short time then add the hot phase B to the hot phase A and start homogenizing with an Ultra Turrax® (13000 rpm/1 minutes per 100 g emulsion). Cool down to ambient temperature while stirring. Phase C: Add phase C and stir until homogeneous. The composition is provided in Table 4.

TABLE 4

O/W sunscreen formulation (All amounts in % w/w)

| Phase | Raw Materials | INCI Name | Amount |
|---|---|---|---|
| A | Cutina ® CP | Cetyl Palmitate | 1.00 |
| | Lanette ® O | Cetearyl Alcohol | 1.00 |
| | Neo Heliopan ® 357 | Butyl Methoxy-dibenzoylmethane | 5.00 |
| | Neo Heliopan ® OS | Ethylhexyl Salicylate | 5.00 |
| | Neo Heliopan ® HMS | Homosalate | 10.00 |
| | Neo Heliopan ® 303 | Octocrylene | 10.00 |
| | Neo Heliopan ® E 1000 | Isoamyl Methoxycinnamate | 3.00 |
| | SymHelios ® 1031 | Benzylidene Dimethoxy-dimethylindanone | 0.30 |
| | Titanium Dioxide according to the invention | Titanium Dioxide, Aluminum Hydroxide, Cetearyl Nonanoate, Stearic Acid | 3.00 |
| | SymWhite ® 377 | Phenylethyl Resorcinol | 0.20 |
| | SymRepair ® 100 | Hexyldecanol, Bisabolol, Cetylhydroxyproline Palmitamide, Stearic Acid, Brassica Campestris Sterols | 1.00 |
| | Symsitive ® 1609 | Pentylene Glycol, 4-t-Butylcylcohexanol | 1.00 |
| | Silsoft(TM) 034 | Caprylyl Methicone | 2.00 |
| | Wacker-Belsil ® CDM 3526 VP | C26-28 Alkyl Dimethicone | 1.00 |
| | EDETA ® BD | Disodium EDTA | 0.10 |
| | Copherol ® 1250 | Tocopheryl Acetete | 0.50 |
| | Keltrol ® CG-BT | Xanthan Gum | 0.50 |
| | Prisorine ® 3505 | Isostearic Acid | 3.00 |
| | α-Bisabolol | Bisabolol | 0.10 |
| B | Water dem | Aqua (Water) | 35.70 |
| | Neo Heliopan ® Hydro | Phenylbenzimidazole Sulfonic Acid | 2.00 |
| | Glycerin 99% | Glycerin | 3.00 |
| | SymSol ® PF3 | Aqua, Pentylene Glycol, Sodium Lauryl Sulfoacetate, Sodium Oleoyl Sarcosinate, Sodium Chloride, Disodium Sulfoacetate, Sodium Oleate | 3.00 |
| | Biotive ® L-Arginine | Arginine | 1.20 |
| | NaOH 10% aq. | Sodium Hydroxide | 0.20 |
| | DragoColor ® Brown | Titanium Dioxide (CI 77891), Iron Oxides (CI 77492), Iron Oxides (CI 77491), Iron Oxides (CI 77499) | 2.00 |
| | SymSave ® H | Hydroxyacetophenone | 0.50 |
| | Phenoxyethanol | Phenoxyethanol | 0.30 |
| | SymDiol ® 68 | 1,2 Hexanediol, Caprylylglycol | 0.30 |
| C | Tapioca pure | Tapioca Starch | 3.00 |
| | SymGlucan | Aqua, Glycerin, Beta-Glucan, 1,2-Hexanediol, Caprylyl Glycol | 1.00 |
| | Fragrance | Parfum | 0.20 |

Example 5

Sunscreen Lotion (O/W), Expected SPF 50

Phase A: Mix the components without Keltrol® and TiO2 and heat to approx. 85° C. Add Keltrol® and TiO2 and homogenize for a short time, approx. 0.5 min. with an Ultra Turrax® T25. Phase B: Mix the components while heating up to 80° C. until a clear solution is obtained. Add the water phase B without stirring to the warm oil phase A. Stir to cool down to 60° C., then start homogenizing with an Ultra Turrax®. Cool down while stirring. Phase C: Add ingredients of Phase C while stirring to phase A/B at ambient temperature. Homogenize with an Ultra Turrax® for a short time. The composition is provided in Table 5.

TABLE 5

O/W sunscreen formulation (All amounts in % w/w)

| Phase | Raw Materials | INCI Name | Amount |
|---|---|---|---|
| A | Emulsiphos ® | Potassium Cetyl Phosphate, Hydrogenated Palm Glycerides | 3.00 |
| | Neo Heliopan ® 357 | Butyl Methoxy-dibenzoylmethane | 5.00 |
| | Neo Heliopan ® HMS | Homosalate | 1.00 |
| | Neo Heliopan ® 303 | Octocrylene | 10.00 |
| | Neo Heliopan ® OS | Ethylhexyl Salicylate | 5.00 |
| | Neo Heliopan ® E1000 | Isoamyl p-Methoxycinnamate | 3.00 |
| | Titanium Dioxide according to the invention | Titanium Dioxide, Aluminum Hydroxide, Cetearyl Nonanoate, Stearic Acid | 3.00 |
| | Prisorine ® 3505 | Isostearic Acid | 2.00 |
| | SymMollient ® S | Cetearyl Nonanoate | 2.00 |
| | Dragoxat ® 89 | Ethylhexyl Isononanoate | 1.00 |
| | EDTA ® BD | Disodium EDTA | 0.10 |
| | Copherol ® 1250 | Tocopherolacetat-Alpha | 0.50 |
| | Floraesters ® K 100 | Hydrolyzed Jojoba Esters (and) Jojoba Esters (and) Water (Aqua) | 1.00 |
| | Wacker Belsil CMD 3526 VP | C26-28 Alkyl Dimethicone | 1.00 |
| | Silsoft ® 034 | Caprylyl Methicone | 2.50 |
| | Keltrol ® CG-BT | Xanthan Gum | 0.50 |
| B | Water, dest. | Water (Aqua) | 38.25 |
| | Neo Heliopan ® Hydro | Phenylbenzimidazole Sulfonic Acid | 3.00 |
| | SymSave ® H | Hydroxyacetophenone | 0.50 |
| | Phenoxyethanol | Phenoxyethanol | 0.30 |
| | SymDiol ® 68 | 1,2 Hexanediol, Caprylylglycol | 0.30 |
| | Biotive ® L-Arginine | Arginine | 1.50 |
| | Lanette ® E | Sodium Cetearyl Sulfate | 0.75 |
| | Glycerin 99.5% | Glycerin | 3.00 |
| | NaOH 10% aq. | Sodium Hydroxide | 0.90 |
| C | Parfüm | Fragrance | 0.20 |
| | Naviance ® Tapioca P LM | Tapioca Starch | 1.00 |
| | Dow Corning ® cosmetic Powder 9701 | Dimethicone/Vinyl Dimethicone Crosspolymer (and) Silica | 0.50 |
| | Fragrance | Parfum | 0.20 |

Example 6

Sunscreen Balm (O/W), Expected SPF 50

Phase A: Mix phase A without SymSave, Keltrol® and NaOH with an Ultra Turrax. Start stirring with a vane stirrer, then add Keltrol and SymSave and stir until a homogeneous turbid solution is obtained. Add NaOH while stirring thoroughly until solution becomes a clear gel. Phase B: Mix the ingredients without TiO2 while heating up to 60° C. until a clear solution is obtained. Add TiO2 and homogenize for a short time. Add the phase B slowly with stirring to the water phase A. Cool down while stirring. Phase C: Add ingredients of Phase C while stirring to phase A/B at ambient temperature. Start homogenizing with an Ultra Turrax® until a homogenous balm is obtained. The composition is provided in Table 6.

TABLE 6

O/W sunscreen formulation (All amounts in % w/w)

| Phase | Raw Materials | INCI Name | Amount |
|---|---|---|---|
| A | Water | Aqua | 39.90 |
| | Neo Heliopan ® Hydro | Phenylbenzimidazole Sulfonic Acid | 3.00 |
| | Neo Heliopan ® AP | Disodium Phenyl Dibenzimidazole Tetrasulfonate | 2.00 |
| | Biotive ® L-Arginine | Arginine | 1.50 |
| | Carbopol Ultrez 20 | Acrylates/C10-30 Alkyl Acrylate Crosspolymer | 0.70 |
| | Glycerin 99% | Glycerin | 3.00 |
| | Keltrol ® SFT | Xanthan Gum | 0.10 |
| | SymSave ® H | Hydroxyacetophenone | 0.50 |
| | NaOH 10% | Sodium Hydroxide | 6.00 |
| B | Neo Heliopan ® HMS | Homosalate | 10.00 |
| | Neo Heliopan ® 303 | Octocrylene | 10.00 |
| | Neo Heliopan ® OS | Ethylhexyl Salicylate | 5.00 |
| | Neo Heliopan ® 357 | Butyl Methoxydibenzoylmethane | 5.00 |
| | Neo Heliopan ® E1000 | Isoamyl p-Methoxycinnamate | 2.00 |
| | Titanium Dioxide according to the invention | Titanium Dioxide, Aluminum Hydroxide, Cetearyl Nonanoate, Stearic Acid | 2.00 |
| | Silcare ® Silicone 41M65 | Stearyl Dimethicone | 1.00 |
| | Floraesters ® K100 | Hydrolyzed Jojoba Esters (and) Jojoba Esters (and) Water (Aqua) | 1.00 |
| | Tocopherylacetat | Tococpheryl Acetate | 0.50 |
| | Wacker-Belsil ® CDM 3526 VP | C26-28 Alkyl Dimethicone | 1.00 |
| | EDTA ® BD | Disodium EDTA | 0.10 |
| C | Ethanol 96% | Alcohol | 3.00 |
| | SymDiol ® 68 | 1,2 Hexanediol, Caprylylglycol | 0.50 |
| | Dow Corning ® 9701 Cosmetic Powder | Dimethicone/Vinyl Dimethicone Crosspolymer, Silica | 2.00 |
| | Fragrance | Parfum | 0.20 |

Example 7

Antiaging Sunscreen Lotion (O/W), Expected SPF 30

Phase A: Mix the components without TiO2 and Keltrol® T to approx. 85° C., then add TiO2 and Keltrol® T. Homogenize for a short time with an Ultra Turrax®. Phase B: Mix the components and heat up to approx. 80° C. until dissolved. Add phase B to phase A while stirring. Cool down while stirring to 60° C. and homogenize with an Ultra Turrax®. Then cool down to ambient temperature while stirring. Phase C: Add all ingredients step by step and stir until homogeneous. Check the pH value. The pH value must be approx. 6.4. If the pH value is correct homogenize with an Ultra Turrax®. The composition is provided in Table 7.

TABLE 7

O/W sunscreen formulation (All amounts in % w/w)

| Phase | Raw Materials | INCI Name | Amount |
|---|---|---|---|
| A | Emulsiphos ® | Potassium Cetyl Phosphate, Hydrogenated Palm Glycerides | 3.80 |
| | Lanette ® 16 | Cetyl Alcohol | 1.00 |
| | Neo Heliopan ® 357 | Butyl Methoxydibenzolymethane | 3.00 |
| | Neo Heliopan ® OS | Ethylhexyl Salicylate | 5.00 |
| | Neo Heliopan ® 303 | Octocrylene | 8.00 |
| | Neo Heliopan ® HMS | Homosalate | 10.00 |
| | Titanium Dioxide according to the invention | Titanium Dioxide, Aluminum Hydroxide, Cetearyl Nonanoate, Stearic Acid | 2.00 |
| | SymHelios ® 1031 | Benzylidene Dimethoxydimethylindanone | 0.50 |
| | Silsoft ® 034 | Caprylyl Methicone | 3.00 |
| | Dragoxat ® 89 | Ethylhexyl Isononanoate | 3.00 |
| | Symsitive ® 1609 | Pentylene Glycol, 4-t-Butylcylcohexanol | 1.00 |
| | Antaron ® WP 660 | Tricontanyl PVP | 1.00 |
| | EDETA ® BD | Disodium EDTA | 0.10 |
| | Copherol ® 1250 | Tocopheryl Acetete | 0.50 |
| | Keltrol ® T | Xanthan Gum | 0.40 |
| | Wacker-Belsil ® CDM 3526 VP | C26-28 Alkyl Dimethicone | 1.00 |
| | Hydrolite ®-5 | Pentylene glycol | 4.25 |
| | SymMollient ® S | Cetearyl Nonanoate | 1.00 |
| B | Water | Aqua (Water) | 40.55 |
| | Neo Heliopan ® Hydro | Phenylbenzimidazole Sulfonic Acid | 1.00 |
| | Neo Heliopan ® AP | Disodium Phenyl Dibenzimidazole Tetrasulfonate | 1.00 |
| | Biotive ® L-Arginine | Arginine | 1.00 |
| | Glycerin 99% | Glycerin | 2.00 |
| | Lanette ® E | Sodium Cetearyl Sulfate | 0.50 |
| | NaOH 10% aq. | Sodium Hydroxide | 0.60 |
| C | SymSave ® H | Hydroxyacetophenone | 0.50 |
| | Symdiol ® 68 | 1,2-Hexanediol, Caprylyl Glycol | 0.50 |
| | Dow Corning ® 9801 Cosmetic Powder | Dimethicone/Vinyl Dimethicone Crosspolymer, Silica | 0.50 |
| | Parfum | Parfum | 0.20 |
| | Dragosantol ® 100 | Bisabalol | 0.10 |
| | SymGlucan ® | Aqua, Glycerin, Beta-Glucan, 1,2-Hexanediol, Caprylyl Glycol | 1.00 |
| | Orgasol ® Caresse | Nylon 6/12 | 2.00 |

Example 8

Low Viscosity Sunscreen Lotion (O/W), Expected SPF 50+

Phase A: Mix ingredients without Titanium Dioxide, Keltrol® and Pemulen® and heat up to approx. 85° C. When all ingredient are dissolved add Titanium Dioxide, Keltrol® and Pemulen® and homogenize with an Ultra Turrax® T25 for a short time (30 seconds). Phase B: Mix ingredients and heat up to approx. 80° C. Add phase B to phase A and homogenizing with an Ultra Turrax® (13000 rpm/1 minutes per 100 g emulsion) at 60° C. Cool down to ambient temperature while stirring. Phase C: Add to phase A/B with stirring until homogeneous. Phase D:

Add to phases A/B/C while stirring. Homogenize with an Ultra Turrax (13000 rpm/1 minutes per 100 g emulsion). The composition is provided in Table 8.

TABLE 8

O/W sunscreen formulation (All amounts in % w/w)

| Phase | Raw Materials | INCI Name | Amount |
|---|---|---|---|
| A | Emulsiphos ® | Potassium Cetyl Phosphate, Hydrogenated Palm Glycerides | 0.80 |

TABLE 8-continued

O/W sunscreen formulation (All amounts in % w/w)

| Phase | Raw Materials | INCI Name | Amount |
|---|---|---|---|
| | Dacorin® 100 SEP | Glyceryl Stearate, PEG-100 Stearate | 1.50 |
| | Neo Heliopan® 357 | Butyl Methoxydibenzolymethane | 5.00 |
| | Neo Heliopan® OS | Ethylhexyl Salicylate | 5.00 |
| | Neo Heliopan® 303 | Octocrylene | 10.00 |
| | Neo Heliopan® HMS | Homosalate | 10.00 |
| | Neo Heliopan® E1000 | Isoamyl p-Methoxycinnamate | 3.00 |
| | Titanium Dioxide according to the invention | Titanium Dioxide, Aluminum Hydroxide, Cetearyl Nonanoate, Stearic Acid | 2.50 |
| | Isoadipate | Diisopropyl Adipate | 2.50 |
| | Silsoft 034 | Caprylyl Methicone | 1.00 |
| | Dow Corning® Wax 2503 | Stearyl Dimethicone | 1.00 |
| | Dow Corning® EL 7040 Hydro Elastomer Blend | Caprylyl Methicone (and) PEG-12 Dimethicone/PPG-20 Crosspolymer | 2.00 |
| | EDETA® BD | Disodium EDTA | 0.10 |
| | Prisorine® 3505 | Isostearic Acid | 1.00 |
| | Copherol® 1250 | Tocopheryl Acetete | 0.50 |
| | Keltrol® CG SFT | Xanthan Gum | 0.15 |
| | Pemulen® TR 2 | Acrylates/C10-30 Alkyl Acrylate Crosspolymer | 0.15 |
| B | Water | Aqua (Water) | 34.40 |
| | Neo Heliopan® Hydro | Phenylbenzimidazole Sulfonic Acid | 3.00 |
| | Neo Heliopan® AP | Disodium Phenyl Dibenzimidazole Tetrasulfonate | 1.10 |
| | Biotive® L-Arginine | Arginine | 1.20 |
| | Glycerin 99% | Glycerin | 1.00 |
| | Propylenglycol | Propylene Glycol | 5.00 |
| | NaOH 10% aq. | Sodium Hydroxide | 3.00 |
| | SymSave® H | Hydroxyacetophenone | 0.50 |
| C | Symdiol® 68 | 1,2-Hexanediol, Caprylyl Glycol | 1.00 |
| D | Dow Corning 9801 Cosmetic Powder | Dimethicone/Vinyl Dimethicone Crosspolymer, Silica | 1.00 |
| | Tapioca pure | Tapioca Starch | 2.00 |
| | Fragrance | Parfum | 0.20 |

Example 9

Infant Sunscreen Cream (O/W) without Organic UV Filters, Expected SPF 30

Phase A: Heat up to approx. 85° C. without Keltrol® CG-T and Titanium Dioxide. Add Keltrol® CG-T and Titanium Dioxide and then homogenize. Part B: Heat to 80-85° C. with stirring then add part B to part A with stirring and then homogenise. Part C: Mix phase C together with stirring. Then add to parts A/B at about 60° C. with stirring until homogeneous. Allow to cool to room temperature and then add phase D with stirring, then homogenize. The composition is provided in Table 9.

TABLE 9

O/W sunscreen formulation (All amounts in % w/w)

| Phase | Raw Materials | INCI Name | Amount |
|---|---|---|---|
| A | Emulsiphos® | Potassium Cetyl Phosphate, Hydrogenated Palm Glycerides | 1.00 |
| | Cutina® CP | Cetyl Palmitate | 2.00 |
| | Tocopherylacetat | Tocopherylacetat | 1.00 |
| | SymMollient® S | Cetearyl Nonanoate | 7.30 |
| | EDTA® BD | Disodium ETDA | 0.10 |
| | Sweet Almond oil raff. | *Prunus Amygdalus* Dulcis Oil | 5.00 |
| | Isodragol® | Triisononanoin | 4.00 |
| | Corapan® TQ | Diethylhexyl 2,6-Naphthalate | 3.00 |
| | Carnicol® N 352 | Hydrogenated Rapeseed Oil | 3.00 |
| | Titanium Dioxide according to the invention | Titanium Dioxide, Aluminum Hydroxide, Cetearyl Nonanoate, Stearic Acid | 5.00 |
| | Keltrol® CG-T | Xanthan Gum | 0.50 |
| B | Water dem. | Water (Aqua) | 39.85 |
| | Zinc Oxide Pi | Zinc Oxide | 20.00 |
| | Glycerin 99.5% | Glycerin | 3.00 |
| | SymSol® PF-3 | Aqua, Pentylene Glycol, Sodium Lauryl Sulfoacetate, Sodium Oleoyl Sarcosinate, Sodium Chloride, Disodium Sulfoacetate, Sodium Oleate, Sodium Sulfate | 3.00 |

TABLE 9-continued

O/W sunscreen formulation (All amounts in % w/w)

| Phase | Raw Materials | INCI Name | Amount |
|---|---|---|---|
| C | Dragosantol ® 100 | Bisabolol | 0.10 |
|   | SymOcide ® PS | Phenoxyethanol, Decylene Glycol, 1,2-Hexanediol | 1.25 |
|   | Citric Acid pure | Citric Acid | 0.60 |
| D | Perfume oil | Parfum (Fragrance) | 0.30 |

Example 10

Sunscreen Spray Expected SPF 50

Phase A: Mix the ingredients without Pemulen® TR2 to approx 60° C. with stirring. Add Pemlen® TR2 and homogenize for a short time, approx 0.5 min. with an Ultra Turrax® T25. Phase B: Dissolve ExpertGel® in water while stirring. When dissolved, add the neutralisation agents and Neo Heliopan® Hydro. When dissolved add the rest of the ingredients and stir until a clear solution is obtained. Heat slightly if necessary to solubilize SymSave® H. Add the water phase B without stirring to the warm oil phase A. Homogenize with an Ultra Turrax® for approximately 5 min. Stir to cool down. Phase C: Mix the ingredients stirring and then to phase A/B. Cool down while stirring. Phase D: Add these separately to phases A/B/C with stirring at ambient temperature. Then homogenise for a short time. The composition is provided in Table 10.

TABLE 10

O/W sunscreen formulation (All amounts in % w/w)

| Phase | Raw Materials | INCI Name | Amount |
|---|---|---|---|
| A | Dracorin ® GOC | Glyceryl Oleate Citrate, Caprylic/Capric Triglyceride | 2.00 |
|   | Neo Heliopan ® 357 | Butyl Methoxydibenzoylmethane | 5.00 |
|   | Neo Heliopan ® HMS | Homosalate | 10.00 |
|   | Neo Heliopan ® 303 | Octocrylene | 10.00 |
|   | Neo Heliopan ® OS | Ethylhexyl Salicylate | 5.00 |
|   | Neo Heliopan ®E1000 | Isoamyl p-Methoxycinnamate | 2.00 |
|   | Titanium Dioxide according to the invention | Titanium Dioxide, Aluminum Hydroxide, Cetearyl Nonanoate, Stearic Acid | 2.50 |
|   | Dragoxat ® 89 | Diisopropyladipate | 3.00 |
|   | SymMollient ® S | Cetearyl Nonanoate | 2.00 |
|   | EDTA ® BD | Disodium EDTA | 0.10 |
|   | Copherol ® 1250 | Tocopherolacetat-Alpha | 0.50 |
|   | Silcare ® Silicone 41M65 | Stearyl Dimethicone | 1.00 |
|   | Wacker Belsil ® CMD 3526 VP | C26-28 Alkyl Dimethicone | 1.00 |
|   | Silsoft 034 | Caprylyl Methicone | 2.00 |
|   | Pemulen TR 2 | Acrylates/C10-30 Alkyl Acrylate Crosspolymer | 0.20 |
| B | Water, dest. | Water (Aqua) | 37.80 |
|   | Neo Heliopan ® Hydro | Phenylbenzimidazole Sulfonic Acid | 2.00 |
|   | Biotive ® L-Arginine | Arginine | 1.00 |
|   | NaOH 10% aq. | Sodium Hydroxide | 1.40 |
|   | SymSol ® PF-3 | Aqua, Pentylene Glycol, Sodium Lauryl Sulfoacetate, Sodium Oleoyl Sarcosinate, Sodium Chloride, Disodium Sulfoacetate | 3.00 |
|   | Propylenglycol | Propylene Glycol | 5.00 |
|   | EG 56 Polymer Expert | Bis-Methoxy PEG-13 PEG-438/PPG-110 SMDI Copolymer | 0.20 |
|   | SymSave ® H | Hydroxyacetophenone | 0.50 |
| C | Phenoxyethanol | Phenoxyethanol | 0.30 |
|   | SymDiol ® 68 | 1,2 Hexanediol, Caprylylglycol | 0.30 |
|   | Dow Corning ® 1503 | Dimethicone/Dimethiconol | 1.00 |
| D | Tapioca Pure | Tapioca Starch | 1.00 |
|   | Perfume oil | Fragrance (Parfum) | 0.20 |

Example 11

Water Resistant Broad Spectrum O/W Expected SPF 50+

Phase A: Heat all components except for the Xanthan Gum and TiO2 to 85° C. Then add Xanthan Gum and TiO2 and homogenise. Phase B: Heat all components to 85° C. and add to Part A with stirring, stir to room temperature. Phase C: Add Part C to Parts A and B and homogenise. The composition is provided in Table 11.

TABLE 11

O/W sunscreen formulation (All amounts in % w/w)

| Phase | Raw Materials | INCI Name | Amount |
|---|---|---|---|
| A | Emulsiphos ® | Potassium Cetyl Phosphate, Hydrogenated Palm Glycerides | 3.50 |
|   | Lanette ® O | Cetearylalcohol | 1.00 |
|   | Neo Heliopan ® HMS | Homosalate | 5.00 |
|   | Neo Heliopan ® 303 | Octocrylene | 10.00 |
|   | Neo Heliopan ® OS | Ethylhexyl Salicylate | 5.00 |
|   | Neo Heliopan ® 357 | Butyl Methoxydibenzoylmethane | 5.00 |
|   | Titanium Dioxide according to the invention | Titanium Dioxide, Aluminum Hydroxide, Cetearyl Nonanoate, Stearic Acid | 5.00 |
|   | Abil ® Wax 9801 | Cetyl Dimethicone | 1.00 |
|   | Silcare Silicone 41M65 | Stearyl Dimethicone | 1.00 |
|   | Baysilone ® oil PK 20 | Phenyl Trimethicone | 2.00 |
|   | Isoadipat | Diisopropyladipate | 2.00 |
|   | Tocopherylacetat | Tocopheryl Acetate | 0.50 |
|   | Antaron ® V216 | VP/Hexadecene Copolymer | 0.50 |
|   | EDTA BD | Disodium EDTA | 0.10 |
|   | Keltrol ® T | Xanthan Gum | 0.50 |
| B | Water dem | Water (Aqua) | Ad 100 |
|   | Biotive ® Troxerutin | Troxerutin | 1.0 |
|   | Neo Heliopan ® AP | Disodium Phenyl Dibenzimidazole Tetrasulfonate | 2.00 |
|   | SymSave ® H | Hydroxyacetophenone | 0.50 |
|   | Biotive ® Arginine | Arginine | 2.20 |
|   | Lara Care ® A-200 | Galactoarabinan | 0.25 |
|   | Hydrolite ® 5 | Pentylene Glycol | 3.00 |
| C | Fragrance | Fragrance (parfum) | 0.30 |

Example 12

Sunscreen Lotion with Tanning Accelerator, Expected SPF 30

Phase A: Mix ingredients to approx. 85° C. without Keltrol®, Aristoflex® and titanium dioxide, when all ingredient are dissolved add Keltrol®, Aristoflex® and Titanium dioxide and homogenize with an Ultra Turrax® for a short time. Part B: Mix ingredients with stirring to approximately 80° C. Add the hot phase B to the hot phase A, cool down with stirring to 60° C. and start homogenizing with an Ultra Turrax®. Cool down to ambient temperature while stirring. Part C: Add the ingredients to parts A/B as listed with stirring and allow to cool to ambient temperature. Part D: Add the ingredients with stirring and homogenise for a short time. The composition is provided in Table 12.

TABLE 12

O/W sunscreen formulation (All amounts in % w/w)

| Phase | Raw Materials | INCI Name | Amount |
|---|---|---|---|
| A | Emulsiphos ® | Potassium Cetyl Phosphate, Hydrogenated Palm Glycerides | 2.00 |
|   | Lanette 16 ® | Cetyl Alcohol | 1.00 |
|   | Neo Heliopan ® 357 | Butyl Methoxydibenzoylmethane | 3.00 |
|   | Neo Heliopan ® OS | Ethylhexyl Salicylate | 5.00 |
|   | Neo Heliopan ® 303 | Octocrylene | 8.00 |
|   | Neo Heliopan ® HMS | Homosalate | 5.00 |
|   | Titanium Dioxide according to the invention | Titanium Dioxide, Aluminum Hydroxide, Cetearyl Nonanoate, Stearic Acid | 2.00 |
|   | SymHelios ® 1031 | Benzylidene Dimethoxydimethylindanone | 0.50 |
|   | Dragoxat ® 89 | Ethylhexyl Isononanoate | 3.00 |
|   | SymMollient ® S | Cetearyl Nonanoate | 1.00 |
|   | Dow Corning ® DC 1503 | Dimethicone, Dimethiconol | 0.50 |

TABLE 12-continued

O/W sunscreen formulation (All amounts in % w/w)

| Phase | Raw Materials | INCI Name | Amount |
|---|---|---|---|
| | Silcare ® Silicone 41M65 | Stearyl Dimethicone | 1.00 |
| | Silsoft ® 034 | Caprylyl Methicone | 1.50 |
| | EDETA ® BD | Disodium EDTA | 0.10 |
| | Vitamin E Acetate | Tocopheryl Acetete | 0.50 |
| | Keltrol ® T | Xanthan Gum | 0.30 |
| | Aristoflex ® Velvet | Polyacrylate Crosspolymer-11 | 0.50 |
| B | Water dem | Aqua (Water) | 55.50 |
| C | Neo Heliopan ® Hydro | Phenylbenzimidazole Sulfonic Acid | 1.50 |
| | Glycerin 99% | Glycerin | 3.00 |
| | Dragosine | Carnosine | 0.20 |
| | Biotive ® L-Arginine | Arginine | 1.00 |
| | Lanette ® E | Sodium Cetearyl Sulfate | 0.70 |
| | SymSave ® H | Hydroxyacetophenone | 0.50 |
| | SymDiol ® 68 | 1,2 Hexanediol, Caprylylglycol | 0.50 |
| D | Fragrance | Parfum | 0.20 |
| | Tapioca Pure | Tapioca Starch | 2.00 |
| | SymBronze ® | Caprylic/Capric Triglyceride, *Isochryris Galbana* Extract | 2.00 |

Example 13

CC Cream with Expected SPF 30

Phase A: Mix ingredients to approx. 85° C. without Keltrol®, Aristoflex® and titanium dioxide, when all ingredient are dissolved add Keltrol®, Aristoflex® and Titanium dioxide and homogenize with an Ultra Turrax® for a short time. Phase B: Add the water and neutralisation agents Biotive® L-Arginine and the sodium hydroxide solution and stir until homogeneous. Then add the Neo Heliopan® Hydro and stir until all has dissolved. Add the rest of ingredients without Dragocolor® to phase B and heat up to approx 80° C., add Dragocolor® and homogenize for a short time then add the hot phase B to the hot phase A and start homogenizing with an Ultra Turrax® (13000 rpm/1 minutes per 100 g emulsion). Cool down to ambient temperature while stirring. Part C: Add the ingredients to parts A/B as listed with stirring and allow to cool to ambient temperature. Part D: Add the ingredients with stirring and homogenise for a short time. The composition is provided in Table 13.

TABLE 13

Cream formulation (All amounts in % w/w)

| Phase | Raw Materials | INCI Name | Amount |
|---|---|---|---|
| A | Cutina ® CP | Cetyl Pamitate | 1.00 |
| | Tegosoft MM | Myristyl Myristate | 1.00 |
| | Lanette ® O | Cetearyl Alcohol | 1.00 |
| | Neo Heliopan ® 357 | Butyl Methoxydibenzoylmethane | 4.00 |
| | Neo Heliopan ® OS | Ethylhexyl Salicylate | 5.00 |
| | Neo Heliopan ® HMS | Homosalate | 7.00 |
| | Neo Heliopan ® 303 | Octocrylene | 7.00 |
| | SymHelios ® 1031 | Benzylidene Dimethoxydimethylindanone | 0.30 |
| | Titanium Dioxide according to the invention | Titanium Dioxide, Aluminum Hydroxide, Cetearyl Nonanoate, Stearic Acid | 1.50 |
| | SymWhite ® 377 | Phenylethyl Resorcinol | 0.20 |
| | SymRepair ® 100 | Hexyldecanol, Bisabolol, Cetylhydroxyproline Palmitamide, Stearic Acid, *Brassica Campestris* Sterols | 1.00 |
| | Symsitive ® 1609 | Pentylene Glycol, 4-t-Butylcylcohexanol | 1.00 |
| | Dragoxat ® 89, 109854 | Ethylhexyl Isononanoate | 2.00 |
| | Silsoft(TM) 034 | Caprylyl Methicone | 3.00 |
| | Wacker-Belsil ® CDM 3526 VP | C26-28 Alkyl Dimethicone | 1.00 |
| | EDETA ® BD | Disodium EDTA | 0.10 |
| | Copherol ® 1250 | Tocopheryl Acetete | 0.50 |
| | Keltrol ® CG-BT | Xanthan Gum | 0.40 |
| | Aristoflex ® Velvet | Polyacrylate Crosspolymer-11 | 0.50 |
| B | Water dem | Aqua (Water) | 4480 |
| | Neo Heliopan ® Hydro, 103089 | Phenylbenzimidazole Sulfonic Acid | 1.50 |
| | Glycerin 99% | Glycerin | 4.00 |
| | Dragosine ® | Carnosine | 0.20 |
| | SymSol ® PF3 | Aqua, Pentylene Glycol, Sodium Lauryl Sulfoacetate, Sodium Oleoyl Sarcosinate, Sodium Chloride, Disodium Sulfoacetate, Sodium Oleate | 2.50 |

TABLE 13-continued

| | Cream formulation (All amounts in % w/w) | | |
|---|---|---|---|
| Phase | Raw Materials | INCI Name | Amount |
| | Biotive ® L-Arginine | Arginine | 1.00 |
| | NaOH 10% aq. | Sodium Hydroxide | 0.30 |
| | DragoColour ® Brown | Titanium Dioxide (CI 77891), Iron Oxides (CI 77492), Iron Oxides (CI 77491), Iron Oxides (CI 77499) | 2.00 |
| | SymSave ® H | Hydroxyacetophenone | 0.50 |
| C | SymDiol ® 68 | 1,2 Hexanediol, Caprylylglycol | 0.50 |
| D | Tapioca pure | Tapioca Starch | 2.00 |
| | Orgasol ® 4000 EXD NAT COS Caresse | Nylon 6/12 | 2.00 |
| | SymGlucan ® | Aqua, Glycerin, Beta-Glucan, 1,2-Hexanediol, Caprylyl Glycol | 1.00 |
| | Fragrance | | 0.20 |

Example 14

Sun Protection Sticks with Expected SPFs of (A) 30 and (B) 50+

Phase A: Mix ingredients and heat with stirring to approx. 80° C. Hold the temperature. Phase B: Mix the ingredients then add phase B to phase A and homogenize. Hold the temperature. Stir slowly to let enclosed air escape from the mass. Transfer to the stick holders at 75-80° C. Two compositions are provided in Table 14.

Example 15

Sunscreen Cream (W/O), Expected SPF 50, Water Resistant

Part A: Mix the ingredients with stirring at about 85° C. Part B: Mix the ingredients with stirring at about 85° C. then add t A. Allow to cool with stirring then homogenise. Part C: Stir in at ambient temperature. The composition is provided in Table 15.

TABLE 14

| | Sun protection formulation (All amounts in % w/w) | | | |
|---|---|---|---|---|
| Phase | Raw Materials | INCI Name | A | B |
| A | Neo Heliopan ® 357 | Butyl Methoxydibenzoylmethane | 5.00 | 5.00 |
| | Neo Heliopan ® 303 | Octocrylene | 1.00 | 10.00 |
| | Neo Heliopan ® OS | Ethylhexyl Salicylate | — | 5.00 |
| | Tinosorb ® S | Bis-Ethylhexyloxyphenol Methoxyphenol Triazine | 3.00 | — |
| | Neo Heliopan ® HMS | Homosalate | — | 10.00 |
| | SymHelios ® 1031 | Benzylidene Dimethoxydimethylindanone | 0.50 | 0.50 |
| | Copherol ® 1250 | Tocopheryl Acetate | 0.70 | 0.70 |
| | Dracorin ® GOC | Glyceryl Oleate Citrate, Caprylic/Capric Triglyceride | 0.50 | 0.50 |
| | Lanette ® O | Cetearyl Alcohol | 7.00 | 5.00 |
| | TeCe-Ozokerit ® N 502 | Ozokerite | 20.00 | 21.00 |
| | Candenilla Wax LT 281 BI | Candelilla (*Euphorbia Cerifera*) Wax | 2.00 | 3.00 |
| | Isoadipate | Diisopropyl Adipate | 5.00 | 7.00 |
| A | Isopropylpalmitat | Isopropyl Palmitate | 13.20 | — |
| | PCL Liquid ® 100 | Cetearyl Ethylhexanoate | 2.00 | 5.20 |
| | SymMollient ® S | Cetearyl Nonanoate | 6.00 | 5.00 |
| | Wacker Belsil ® CDM 3526 VP | C26-28 Alkyl Dimethicone | 2.00 | 2.00 |
| | Silcare ® Silicone 41 M45 | Stearyl Dimethicone | 1.00 | 1.00 |
| | Neutral oil | Caprylic/Capric Triglyceride | 10.00 | — |
| | Dragoxat ® 89 | Ethylhexyl Isononanoate | 5.00 | 7.00 |
| | Dragosantol ® 100 | Bisabolol | 0.10 | 0.10 |
| B | Titanium Dioxide according to the invention | Titanium Dioxide, Aluminum Hydroxide, Cetearyl Nonanoate, Stearic Acid | 5.00 | 5.00 |
| | Zinc Oxide PI | Zinc Oxide | — | 5.00 |
| | Dow Corning ® Cosmetic Powder 9701 | Dimethicone/Vinyl Dimethicone Crosspolymer (and) Silica | 2.00 | 2.00 |

TABLE 15

| Phase | Raw Materials | INCI Name | Amount |
|---|---|---|---|
| | Cream formulation (All amounts in % w/w) | | |
| A | Dehymuls ®PGPH | Polyglyceryl-2 Dipolyhydroxystearate | 5.00 |
| | Copherol ®1250 | Tocopheryl Acetate | 0.50 |
| | Permulgin ® 3220 | Ozokerite | 0.50 |
| | Aluminium stearate | Aluminium Stearate | 0.50 |
| | Neo Heliopan ® OS | Ethylhexyl Salicylate | 5.00 |
| | Neo Heliopan ® HMS | Homosalate | 7.00 |
| | Neo Heliopan ® 303 | Octocrylene | 7.00 |
| | Tegosoft ® TN | C12-15 Alkyl Benzoate | 25.00 |
| | Neo Heliopan ® 357 | Butyl Methoxydibenzolymethane | 2.00 |
| | EDETA ® BD | Disodium EDTA | 0.10 |
| | Titanium Dioxide according to the invention | Titanium Dioxide, Aluminum Hydroxide, Cetearyl Nonanoate, Stearic Acid | 5.00 |
| B | Water, dist. | Water (Aqua) | 15.30 |
| | Glycerol, 99% | Glycerin | 4.00 |
| | Dragocid ® Liquid | Phenoxyethanol, Methylparaben, Ethylparaben, Butylparaben, Propylparaben, Isobutylparaben | 1.00 |
| | Neo Heliopan ® Hydro, 22% strength solution neutralised with Triethanolamine | Phenylbenzimidazole Sulfonic Acid | 13.70 |
| | Neo Heliopan ® AP 22% strength solution neutralised with Triethanolamine | Disodium Phenyl Dibenzimidazole Tetrasulfonate | 6.80 |
| | Biotive ® Troxerutin | Troxerutin | 0.30 |
| | Triethanolamine | Triethanolamine | 0.50 |
| | Magnesium sulfate | Magnesium Sulfate | 0.50 |
| C | Perfume oil | Parfum (Fragrance) | 0.30 |

Example 16

| Raw material | INCI | 16.1 | 16.2 | 16.3 | 16.4 | 16.5 | 16.6 | 16.7 | 16.8 | 16.9 | 16.10 | 16.11 |
|---|---|---|---|---|---|---|---|---|---|---|---|---|
| | O/W Emulsions, SPF >20 | | | | | | | | | | | |
| | Emulsifier | | | | | | | | | | | |
| Emulsiphos ® (Symrise) | Potassium Cetyl Phosphate, Hydrogenated Palm Glycerides | | | | | | 2.0 | | | | | |
| Dracorin ® CE (Symrise) | Glyceryl Stearate Citrate | 1.0 | 1.0 | | | | | | | | | |
| Dracorin ® GOC (Symrise) | Glyceryl Oleyl Citrate | | | | | 4.0 | | | | | | |
| Dehymuls ® PGPH | Polyglyceryl 2-Dipolyhydroxystearate | 0.25 | 0.25 | | | | | | | | | |
| Emulgade ® F | Cetearyl Alcohol, Peg-40 Castor Oil, Sodium Cetearyl Sulfate | | | | | | | | | 3.75 | | |
| Arlacel ® P135 | PEG-30 Dipolyhydroxystearate | | | | | | | | | 1.0 | | |
| Tego Care ® 450 | Polyglyceryl-3 Methyl-glucose Distearate | | | | | | | | | 2.0 | | |
| Tego ® SMS | Sorbitan Stearate | | | | | 0.5 | | | 1.0 | | | |
| Dragil ® SE | Glyceryl Stearate SE | | | | | | | 1.5 | | | | |
| Cutina ® GMS V | Glyceryl Stearate | | | 2.5 | 1.0 | | 4.0 | | | | 4.0 | |
| Prisorine ® 3505 - LQ-(GD) | Isostearic Acid | | | | | | | 1.0 | | | | |
| Permulgin ® 3220 | Stearic Acid | | | | | 1.0 | | | | 4.0 | | 0.5 |
| Myrj ® 52 | PEG 40 Stearate | | | | 1.0 | | | | | 1.0 | | |
| Crodet ® S100 | PEG 100 Stearate | | | | | | | | | | 2.0 | 0.5 |
| Amphisol ® K | Potassium Cetyl Phosphate | | | | | | 2.0 | | | | 0.5 | 2.0 |
| Lanette ® E | Sodium Cetearyl Sulphate | | | | | | | | 0.5 | | | |
| Emulgin ® B2 | Ceteareth-20 | | | | | | | 0.7 | | | 1.0 | |
| Oil Soluble UV Filters | | | | | | | | | | | | |
| Neo Heliopan ® AV (Symrise) | Ethylhexyl Methoxy-cinnamate | 8.0 | 10.0 | | | 4.0 | | | 5.0 | | | |
| Neo Heliopan ® 303 (Symrise) | Octocrylene | | | 5.0 | 5.0 | | | 5.0 | | | 2.4 | 10.0 |

-continued

| | | O/W Emulsions, SPF >20 | | | | | | | | | | |
|---|---|---|---|---|---|---|---|---|---|---|---|
| Raw material | INCI | 16.1 | 16.2 | 16.3 | 16.4 | 16.5 | 16.6 | 16.7 | 16.8 | 16.9 | 16.10 | 16.11 |
| Neo Heliopan ® 357 (Symrise) | Butyl Methoxydibenzoyl-methane | 4.5 | 5.0 | | 2.5 | 0.5 | 3.0 | 0.5 | 2.0 | 2.0 | 3.0 | 3.0 |
| Neo Heliopan ® E 1000 (Symrise) | Isoamyl p-Methoxy-cinnamate | | | | 5.0 | | 10.0 | | | | | |
| Neo Heliopan ® HMS (Symrise) | Homosalate | | | | 5.0 | 5.0 | | | | 3.0 | 10.0 | |
| Neo Heliopan ® OS (Symrise) | Ethylhexyl Salicylate | | | | 2.0 | 5.0 | | | | 5.0 | 5.0 | 3.0 |
| Neo Heliopan ® MBC (Symrise) | 4-Methylbenzylidene-camphor | | | | 4.0 | | | | | | | |
| Neo Heliopan ® MA (Symrise) | Menthyl Anthranilate | | | | | 1.0 | | | | | | |
| Mexoryl ® XL | Drometrizole Trisiloxane | | | | 1.0 | | | | | | | 3.0 |
| Uvinul ® T-150 | Ethylhexyl Triazone | 5.0 | 1.0 | 1.0 | 0.5 | | | | | | | 0.5 |
| Tinosorb ® S | Bis-Ethylhexyloxyphenol Methoxyphenyl Triazine | 0.5 | 4.0 | | 0.5 | | | | | | | |
| Uvinul ® A Plus | Diethylamino Hydroxy-benzoyl Hexyl Benzoate | 1.0 | 1.0 | 2.0 | 0.5 | 5.0 | | | | | | |
| Tinosorb ® M | Bisoctrizole | | | 2.0 | | 0.75 | 1.0 | | | 5.0 | | |
| Parsol ® SLX | Polysiloxane-15 | | | | 2.0 | | | | | | | |
| Uvasorb ® HEB | Diethylhexyl Butamido Triazone | | | | 0.5 | | 2.0 | | | | | |
| Water Soluble UV Filters | | | | | | | | | | | | |
| Neo Heliopan ® AP (Symrise), | Disodium Phenyl-dibenzimidazoletetra-sulphonate | 0.5 | 0.75 | 1.0 | 0.2 | 1.5 | 0.5 | 1.0 | 0.5 | 0.3 | 4.6 | 0.5 |
| Neo Heliopan ® Hydro (Symrise | Phenylbenzimidazole-sulphonic Acid | 1.0 | 1.0 | 2.0 | 4.0 | 2.0 | 1.5 | 2.0 | 2.0 | 2.0 | 1.0 | 2.0 |
| Mexoryl ® SX | Terephthalylidene Dicamphor Sulfonic Acid | | | | 0.5 | | 1.0 | | | | | 0.5 |
| Sulisobenzone | Benzophenone-4 | 0.5 | | | | 1.0 | | | 0.5 | 2.0 | | |
| Neutralisation base | | qs | qs | qs | qs | qs | qs | qs | qs | qs | qs | qs |
| Microfine UV attenuating Pigments | | | | | | | | | | | | |
| Titanium Dioxide according to the invention | Titanium Dioxide, Aluminum Hydroxide, Cetearyl Nonanoate, Stearic Acid | 3.0 | 3.0 | 3.0 | 0.5 | 2.0 | 3.0 | 6.0 | 1.0 | 4.5 | 2.5 | 3.0 |
| | Zinc Oxide | | | | | | 3.0 | 6.0 | | | | |
| Tinosorb ® A2B | Tris-Biphenyl Triazine | 3.0 | | 1.1 | 2.5 | | 1.5 | | 0.5 | | | 5.0 |
| Other oil soluble components | | | | | | | | | | | | |
| PCL Liquid 100 | Cetearyl Octanoate | | | | | 3.0 | 3.0 | | | | | |
| Corapan TQ ® (Symrise) | Diethylhexyl 1,6-Naphthalate | | | | | | | | 3.0 | | 3.0 | |
| Dragoxat 89 (Symrise) | Ethylhexyl Isononoate | | | | 1.0 | 3.0 | | | | | | |
| Isoadipate | Diisopropyl Adipate | | | 3.0 | 1.0 | 3.0 | | | | | | |
| Isopropyl myristate (Symrise) | Isopropyl Myristate | | | | | | | 2.0 | | | 4.0 | |
| Neutral oil (Symrise) | Caprylic/Capric Triglyceride | | | | | 2.0 | | 5.0 | | 4.0 | | |
| Isodragol (Symrise) | Triisononanoin | | | | | | 1.0 | | 6.0 | | | |
| Cetiol ® OE | Dicaprylyl Ether | 2.0 | 2.0 | | | | 2.0 | 1.0 | 3.0 | | | |
| | Dicaprylyl Carbonate | | | 2.0 | | | 2.0 | | | | | |
| | Isohexadecane | | | | | | | | | | | 3.0 |
| Paraffin oil | Mineral Oil | | | | | | | | | 4.0 | | |
| Tegosoft ® TN (Goldschmidt) | C12-15 Alkyl Benzoate | 5.0 | 5.0 | 3.0 | 4.0 | 2.0 | | | 1.0 | 4.0 | 5.0 | 5.0 |
| Abil ® 100 (Goldschmidt) | Dimethicone | | | | 1.0 | | | | 2.0 | | 2.0 | 0.5 |
| Dow Corning ® 193 Fluid(Dow corning) | Peg-12 Dimethicone | | | | 1.0 | | | | | | | |
| | Cyclopentasiloxane | | | | | | | | | | | 5.0 |
| | Cetyl Dimethicone | | | | | | | | | 1.0 | | |
| | Hydrogenated Coco-Glycerides | 1.0 | 1.0 | | | | 1.0 | 0.5 | | | | |
| | Butylene Glycol Dicaprylate/Dicaprate | 1.0 | 1.0 | 4.0 | | | 1.0 | 7.5 | | | | |
| | Dibutyl Adipate | | | | 2.0 | | | | | | | |
| | Trimethoxycaprylylsilane | | | | | | 1.0 | | | | | |

-continued

| | | O/W Emulsions, SPF >20 | | | | | | | | | | |
|---|---|---|---|---|---|---|---|---|---|---|---|
| Raw material | INCI | 16.1 | 16.2 | 16.3 | 16.4 | 16.5 | 16.6 | 16.7 | 16.8 | 16.9 | 16.10 | 16.11 |
| Lanette ® O | Cetearyl Alcohol | | | | 1.5 | | | | | | | |
| Lanette ® 16 | Cetyl Alcohol | | | | | 1.0 | | 1.0 | | 0.5 | 1.0 | |
| Lanette ® 18 | Stearyl Alcohol | 1.0 | 1.0 | 2.0 | | | 1.0 | | 4.5 | | | |
| Dragosantol ® 100 (Symrise) | Bisabolol | | | | 0.2 | 0.1 | | | | | | |
| Copherol 1250 ® | Tocopheryl Acetate | 0.5 | 0.5 | 0.5 | 0.5 | 0.5 | 0.5 | 0.5 | | 0.5 | | 0.5 |
| D-Panthenol (BASF) | Panthenol | | 0.5 | | | | | | 0.5 | 0.5 | | |
| | Retinyl-Palmitate | | | | | | 0.5 | | | | | |
| Frescolat ® ML | Menthyl Lactate | | | | 0.5 | | | | 0.5 | | | |
| Fragrance | Fragrance/Parfum | qs | qs | qs | qs | qs | qs | qs | qs | qs | | |
| | Creatinine | 0.05 | 0.05 | | | | | | | | | |
| EDTA BD ® (BASF) | Disodium-EDTA | 0.2 | 0.2 | 0.15 | 0.15 | 0.15 | 0.2 | 0.15 | 0.15 | 0.15 | 0.2 | 0.2 |
| Viscosity modifiers/stability aids | | | | | | | | | | | | |
| Bentone Gel ® M IO V (Elementis Specialties) | Mineral Oil and Quaternium-Disteardimonium Hectorite and Propylene Carbonate | | | | | | | | 0.5 | | | |
| Carbopol ®Ultrez 10 (Lubrizol) | Carbomer | | | | | 0.10 | | | | 0.2 | | |
| Carbopol ®ETD 2001 (Lubrizol) | Carbomer | | | | 0.5 | | 0.1 | | | | | |
| Keltrol T ® (CP-Kelco) | Xanthan Gum | 0.2 | 0.2 | 0.3 | 0.3 | 0.4 | 0.2 | 0.2 | | | 0.2 | 0.2 |
| Pemulen ® TR 2 (Lubrizol) | Acrylates/C10-30 Alkyl Acrylate Crosspolymer | | | | | | 0.2 | | 0.1 | | | 0.1 |
| Veegum ultra ® (Vanderbilt) | Magnesium Aluminium Sulphate | 1.0 | 1.0 | | | 0.2 | 1.0 | | | | | |
| Aerosil ® 200 | Silica | | | | | | | | | 0.5 | 0.2 | |
| Film Forming Polymers | | | | | | | | | | | | |
| Antaron ® V-216/516 | VP/Hexadecene Copolymer | 0.5 | 0.5 | | | 2.0 | 0.5 | | | 1.0 | 1.0 | 2.0 |
| Antaron ® V-220 | VP/Eicosene Copolymer | | | | | | | | 2.0 | | | |
| Dermacry ® I 79 | Acrylates/Octylacrylamide Copolymer | | | | 2.0 | | 0.5 | | | | 1.0 | |
| Antaron ® WP-660 | Tricantonyl PVP | | 1.0 | | | | | 2.0 | | | | |
| Avalure ® UR 450/525 | PPG-17/IPDI/DMPA copolymer | | | 1.0 | | | 1.0 | | | | | |
| Other water soluble components | | | | | | | | | | | | |
| Water | Water (Aqua) | qs | qs | qs | qs | qs | qs | qs | qs | qs | qs | qs |
| Neutralisation base for acidic components such as carbomers, and/or stearic acid etc | AMP, TEA, KOH, NaOH, Arginine, Tromethamine | qs | qs | qs | qs | qs | qs | | qs | qs | qs | qs |
| Biotive ® Troxerutin (Symrise) | Troxerutin | 0.1 | 0.3 | 0.5 | 0.1 | 0.5 | 0.2 | 0.2 | 0.2 | 0.1 | 0.7 | 0.2 |
| Preservation agents | | qs | qs | qs | qs | qs | qs | qs | qs | qs | qs | qs |
| 1,3-Butylene glycol | 1,3-Butylene Glycol | | | | | 1.0 | | | | | | |
| Ethanol (96%) | Ethyl Alcohol | 15.0 | 3.0 | | | | 3.0 | 3.0 | 2.0 | | | |
| Glycerin 99% | Glycerin | 5.0 | 5.0 | 4.5 | 0 | 5.0 | 3.0 | 5.0 | | 3.0 | 3.0 | 4.0 |
| Hydrolite ®-5 (Symrise) | Pentylene Glycol | 5.0 | 5.0 | 3.0 | | 2.0 | 5.0 | 4.0 | 3.0 | | | |
| Symdiol ® 68 (Symrise) | 1,2-hexylenediol and 1,2-Caprylyldiol | | | | 0.5 | | | | | | | |
| 1,2-Propylene glycol | Propylene Glycol | | | | | | 1.0 | | | 5.0 | | 5.0 |
| SymSave ® H (Symrise) | Hydroxyacetophenone | 0.5 | 0.5 | 0.5 | 0.5 | 0.5 | 0.5 | 0.5 | 0.5 | 0.7 | 0.7 | 0.7 |
| Soja extract | Glycine soja (soybean) germ extract | | | | 0.5 | 0.5 | | | 0.5 | 1.0 | 2.0 | 0.5 |
| | Sodium Ascorbyl Phosphate | | | | 0.2 | | | | | | | |
| DHA | Dihydroxyacetone | | | | | | 3.0 | | 5.0 | | | |
| Water soluble dyestuff | | Qs | qs | qs | qs | qs | qs | qs | qs | qs | qs | qs |
| Plant Extract(s) | | qs | qs | 5.00 | qs | qs | qs | qs | qs | 5.0 | qs | qs |

Example 17

| | | W/O Emulsions, SPF >20 | | | | | | | | | |
|---|---|---|---|---|---|---|---|---|---|---|---|
| Raw material | INCI | 17.1 | 17.2 | 17.3 | 17.4 | 17.5 | 17.6 | 17.7 | 17.8 | 17.9 | 17.10 |
| | Polyglyceryl 2-Dipolyhydroxystearate | 4.0 | 5.0 | | | | | | | 3.0 | 2.5 |
| | PEG-45/Dodecyl Glycol Copolymer | | | | | 1.0 | | | | | |
| | Polyglyceryl 3-Polyricinoleate | | | | | | | | | 3.0 | 3.5 |
| | Cetyl PEG/PPG-10/1-Dimethicone | | | | | 1.5 | | | | | |
| | Lauryl PEG/PPG-18/18 Methicone | | | | | | 3.0 | | | | |
| | Cetearyl Alcohol, Peg-40 Castor Oil, Sodium Cetearyl Sulfate | | | | | | | 3.75 | | | |
| | PEG-30 Dipolyhydroxystearate | | | 3.5 | 3.5 | | 3.5 | 1.0 | | | |
| | Polyglyceryl-3 Methylglucose Distearate | | | | | 2.0 | | | 2.0 | | |
| | Sorbitan Stearate | | | | | | | | 1.0 | | |
| Oil Soluble UV Filters | | | | | | | | | | | |
| Neo Heliopan ® AV (Symrise) | Ethylhexyl Methoxy-cinnamate | 10.0 | 2.0 | | 2.0 | 3.0 | | | | | 5.0 |
| Neo Heliopan ® 303 (Symrise) | Octocrylene | 5.0 | 2.0 | 3.0 | 3.0 | 3.0 | 8.0 | | 5.0 | 10.0 | 3.0 |
| Neo Heliopan ® 357 (Symrise) | Butyl Methoxydibenzoyl-methane | 5.0 | 1.0 | | 2.0 | 2.0 | 3.0 | 0.5 | 2.0 | 3.0 | 3.0 |
| Neo Heliopan ® E 1000 (Symrise) | Isoamyl p-Methoxy-cinnamate | | 1.0 | | 1.0 | 3.0 | | | | | 10.0 |
| Neo Heliopan ® HMS (Symrise) | Homosalate | | 1.0 | | 1.0 | 3.0 | 2.0 | | | 10.0 | 3.0 |
| Neo Heliopan ® OS (Symrise) | Ethylhexyl Salicylate | | 1.0 | | 1.0 | 3.0 | 3.0 | | | 5.0 | 5.0 |
| Neo Heliopan ® MBC (Symrise) | 4-Methylbenzylidene-camphor | | 2.0 | | 0.5 | | | | | | 1.0 |
| Neo Heliopan ® MA (Symrise) | Menthyl Anthranilate | | 1.0 | | 0.5 | | | | | | |
| Mexoryl ® XL | Drometrizole Trisiloxane | | 2.0 | | 3.0 | | 3.0 | | | | |
| Uvinul ® T-150 | Ethylhexyl Triazone | | 0.5 | 2.0 | 0.5 | 3.0 | 1.0 | | | 1.0 | 1.0 |
| Tinosorb ® S | Bis-Ethylhexyloxyphenol Methoxyphenyl Triazine | 1.0 | 0.5 | 2.5 | 0.5 | 3.0 | | | | 1.5 | 1.5 |
| Uvinul ® A Plus | Diethylamino Hydroxy-benzoyl Hexylbenzoate | 1.0 | 0.5 | 2.0 | 0.5 | 0.5 | | | | 1.0 | 1.0 |
| Parsol ® SLX | Polysiloxane-15 | | 1.0 | | 1.0 | | | | | | 3.0 |
| Uvasorb ® HEB | Diethylhexyl Butamido Triazone | 0.5 | 0.5 | | 5.0 | | | | | | |
| Water Soluble UV Filters | | | | | | | | | | | |
| Neo Heliopan ® AP (Symrise) | Disodium Phenyl-dibenzimidazoletetra-sulphonate | 1.0 | 0.5 | 1.0 | 0.5 | 0.5 | 0.75 | 0.5 | 0.5 | 4.0 | 1.0 |
| Neo Heliopan ® Hydro (Symrise) | Phenylbenzimidazole-sulphonic Acid | 0.75 | 4.0 | 2.0 | 1.0 | 1.25 | 1.5 | 2.0 | 2.0 | 1.0 | 1.0 |
| Mexoryl ® SX | Terephthalylidene Dicamphor Sulfonic Acid | | 0.5 | | 0.5 | | 1.0 | | | | |
| Sulisobenzone | Benzophenone-4 | 1.0 | | | | 3.0 | | | | | |
| Neutralization base | | qs | qs | qs | qs | qs | qs | qs | qs | qs | qs |
| Microfine UV attenuating Pigments | | | | | | | | | | | |
| Titanium Dioxide according to the invention | Titanium Dioxide, Aluminum Hydroxide, Cetearyl Nonanoate, Stearic Acid | 3.0 | 3.0 | 3.0 | 3.0 | 3.0 | 5.0 | 6.0 | 1.0 | 3.0 | 3.0 |
| | Zinc Oxide | | | | | | | 10.0 | | | |
| Other oil soluble components | | | | | | | | | | | |
| PCL Liquid 100 (Symrise) | Cetearyl Octanoate | | | | | | | | | | |
| Corapan TQ ® (Symrise) | Diethylhexyl 1,6-Naphthalate | | | | | | | 3.0 | | | |

-continued

| | | W/O Emulsions, SPF >20 | | | | | | | | | |
|---|---|---|---|---|---|---|---|---|---|---|
| Raw material | INCI | 17.1 | 17.2 | 17.3 | 17.4 | 17.5 | 17.6 | 17.7 | 17.8 | 17.9 | 17.10 |
| Dragoxat 89 (Symrise) | Ethylhexyl Isononoate | | | | 1.0 | | | | | | |
| Isoadipate (Symrise) | Diisopropyl Adipate | | | 3.0 | 5.0 | 5.0 | | | | | |
| Isopropyl myristate (Symrise) | Isopropyl Myristate | 3.0 | | | | | | 2.0 | | 4.0 | |
| Neutral oil (Symrise) | Caprylic/Capric Triglyceride | | 5.0 | | 3.0 | | | 5.0 | | 4.0 | 4.0 |
| Isodragol ® (Symrise) | Triisononanoin | | | | | | | | 6.0 | | |
| | Isohexadecane | | | | | | 6.0 | | | | |
| | Dicaprylyl Carbonate | | | 5.0 | | | 8.0 | | | | |
| Cetiol ® OE | Dicaprylyl Ether | | 5.0 | | 5.0 | | | 1.0 | 3.0 | | |
| Paraffin oil | Mineral Oil | | | | | | | | | | |
| Tegosoft TN ® (Goldschmidt) | C12-15 Alkyl Benzoate | 10.0 | 10.0 | 10.0 | 4.0 | 9.0 | | | 1.0 | 5.0 | 5.0 |
| Abil 100 ® (Goldschmidt) | Dimethicone | | 1.0 | | 1.0 | | | | 2.0 | | |
| Dow Corning ® 193 Fluid (Dow corning) | PEG-12 Dimethicone | | | | | | | 1.0 | | | |
| | Cetyl Dimethicone | | | | 2.0 | | | | | 2.0 | 2.0 |
| | Cyclomethicone | | | | | 15 | | | | | |
| | Cyclohexasiloxane | | | | | | | 5.0 | | | |
| | Cyclopentasiloxane | | | | | | | 5.0 | | | |
| | Simethicone | | | | | | | | | 2.0 | 2.0 |
| | Hydrogenated Coco-Glycerides | | | | 1.0 | | | | 0.5 | | |
| | Butylene Glycol Dicaprylate/Dicaprate | 7.5 | 3.0 | | 3.0 | 8.0 | | 7.5 | | | |
| | Trimethoxycaprylylsilane | | | | | 0.2 | | | | | |
| Lanette ® 16 | Cetyl Alcohol | | | | | | | 1.0 | | 0.5 | 0.5 |
| Lanette ® 18 | Stearyl Alcohol | | | | | | | | 3.0 | | |
| alpha-Bisabolol (Symrise) | Bisabolol | | 0.2 | | 0.2 | 0.2 | | | | 0.1 | 0.1 |
| Copherol 1250 ® | Tocopheryl Acetate | 0.5 | 0.5 | 0.5 | 0.5 | 0.5 | 0.5 | 0.5 | | 0.5 | 0.5 |
| D-Panthenol (BASF) | Panthenol | 0.5 | 0.5 | 0.5 | 0.5 | 0.5 | 0.5 | 0.5 | | 0.5 | 0.5 |
| | Retinyl Palmitate | | | | 0.5 | | | | 0.5 | | |
| Fragrance | Fragrance/Parfum | qs | qs | qs | qs | qs | qs | qs | qs | qs | qs |
| | Creatinine | 0.05 | 0.05 | 0.05 | | | | | | | |
| | Taurine | | | 1.0 | | | | | | | |
| EDTA BD ® (BASF) | Disodium-EDTA | 0.2 | 0.2 | 0.15 | 0.15 | 0.15 | 0.2 | 0.15 | 0.15 | 0.15 | 0.15 |
| Viscosity modifiers/stability aids | | | | | | | | | | | |
| Bentone Gel ® M IO V (Elementis Specialties) | Mineral Oil and Disteardimonium Hectorite and Propylene Carbonate | | | | | | | | 0.5 | | |
| | Microcrystalline Wax | | | | | | | | | 2.0 | 2.0 |
| | Beeswax | | | | | 0.3 | | | | | |
| | Tricontanyl PVP | | | | | | | | | 2.0 | 2.0 |
| Keltrol T ® (Calgon) | Xanthan Gum | | | | | | | 0.2 | | | |
| Pemulen ® TR 2 (Novion) | Acrylates/C10-30 Alkyl Acrylate Crosspolymer | | | | 0.3 | | | | 0.1 | | |
| | Sodium Starch Octenylsuccinate | 0.5 | 0.5 | 0.4 | | | | | | | |
| Aerosil ® 200 | Silica | | | | | | | | | | |
| | Magnesium Sulfate | 0.3 | 0.3 | 0.3 | | | | | | | |
| | Sodium Chloride | | | | | 0.5 | 0.5 | | | | |
| Other water soluble components | | | | | | | | | | | |
| Water | Water (Aqua) | qs | qs | qs | qs | qs | qs | qs | qs | qs | qs |
| Neutralisation base for acidic components such as carbomers, and/or stearic acid etc | | qs | qs | qs | qs | | qs | | qs | qs | qs |
| Biotive ® Troxerutin (Symrise) | Troxerutin | 0.2 | 0.1 | 0.3 | 0.2 | 0.5 | 0.2 | 0.3 | 0.1 | 0.7 | 0.3 |
| Preservation agents | | qs | qs | qs | qs | qs | qs | qs | qs | qs | qs |
| 1,3-Butylene glycol | 1,3-Butylene Glycol | 5.0 | 5.0 | 3.0 | 3.0 | | | | | | |
| Ethanol (96%) | Ethyl Alcohol | 2.0 | 2.0 | 2.0 | 3.0 | 3.0 | 10.0 | 3.0 | 2.0 | 4.0 | 4.0 |

W/O Emulsions, SPF >20

| Raw material | INCI | 17.1 | 17.2 | 17.3 | 17.4 | 17.5 | 17.6 | 17.7 | 17.8 | 17.9 | 17.10 |
|---|---|---|---|---|---|---|---|---|---|---|---|
| Glycerin 99% | Glycerin | 5.0 | 5.0 | 2.0 | 2.0 | 4.0 | 5.0 | 3.0 | 5.0 | 3.0 | 3.0 |
| Hydrolite ®-5 (Symrise) | Pentylene Glycol | 1.0 | 1.0 | 3.0 | 3.0 | 2.0 | 2.0 | 4.0 | 3.0 | | |
| Symdiol ® 68 (Symrise) | 1,2-hexylenediol and 1,2-Caprylyldiol | | | 0.5 | 0.5 | 0.5 | | | | | |
| 1,2-Propylene glycol | Propylene Glycol | | | | | | 3.0 | | | 5.0 | 5.0 |
| SymSave ® H (Symrise) | Hydroxyacetophenone | 0.5 | 0.5 | 0.5 | 0.5 | 0.5 | 0.5 | 0.5 | 0.5 | 0.7 | 0.7 |
| Soja extract | Glycine soja (soybean) germ extract | | | 0.5 | 0.5 | | | | | | |
| | Sodium Ascorbyl Phosphate | | | 0.5 | 0.2 | 0.2 | | | | | |
| Water soluble dyestuff | | qs | qs | qs | qs | qs | qs | qs | qs | qs | qs |
| Plant Extract(s) | | qs | qs | qs | qs | qs | qs | qs | qs | 5.0 | 5.0 |

Example 18

Spray/Mousse Emulsions, SPF >20

| Raw material | INCI | 18.1 | 18.2 | 18.3 | 18.4 | 18.5 | 18.6 | 18.7 | 18.8 | 18.9 | 18.10 |
|---|---|---|---|---|---|---|---|---|---|---|---|
| Emulsifier | | | | | | | | | | | |
| | Polyglycery 2-Dipolyhydroxystearate | 3.0 | | | | | | | | | |
| | Disodium PEG-5 Lauryl Citrate Sulfosuccinate | 2.5 | | | | | | | | | |
| | Capryl/Capramidopropyl Betaine | 0.7 | | | | | | | | | |
| | Sodium Laureth Sulfate | 0.3 | | | | | | | | | |
| Emulgin ® B2 | Ceteareth-20 | | 1.5 | 1.5 | | | | | | 2.0 | |
| | Polyester-5 | | | | 2.5 | | | | | | |
| | Sorbitan Laurate | | | | | | 2.5 | | | | |
| | Polyglycery I-10 Laurate | | | | | | 2.0 | | | | |
| | PPG-15 Stearyl Ether | | | | | | | | 4.0 | | |
| | Polyacrylate-3 | | | | | 1.0 | | | | | |
| | Stearyl Phosphate | | | | | | | | | 2.5 | |
| | Sorbitan Stearate | | | | | | | | | | 0.5 |
| | Stearic Acid | | | | | | | 1.0 | | | 1.0 |
| | PEG 40 Stearate | | | | | | | | | | 1.0 |
| Oil Soluble UV Filters | | | | | | | | | | | |
| Neo Heliopan ® AV (Symrise) | Ethylhexyl Methoxycinnamate | | 6.0 | | | | | | 5.0 | | 6.0 |
| Neo Heliopan ® 303 (Symrise) | Octocrylene | 5.0 | | 8.0 | 10.0 | 10.0 | 5.0 | 4.0 | | 4.0 | |
| Neo Heliopan ® 357 (Symrise) | Butyl Methoxydibenzoyl-methane | 3.0 | 4.0 | 4.0 | 2.0 | 2.5 | 3.0 | 5.0 | | 2.0 | 3.0 |
| Neo Heliopan ® E 1000 (Symrise) | Isoamyl p-Methoxycinnamate | | | | | | | | 5.0 | | |
| Neo Heliopan ® HMS (Symrise) | Homosalate | | | 3.0 | 3.0 | 5.0 | 5.0 | | | 3.0 | |
| Neo Heliopan ® OS (Symrise) | Ethylhexyl Salicylate | | | 3.0 | 5.0 | 5.0 | 5.0 | 4.0 | | 3.0 | |
| Neo Heliopan ® MBC (Symrise) | 4-Methylbenzylidene-camphor | | | | | | | | | 0.5 | |
| Neo Heliopan ® MA (Symrise) | Menthyl Anthranilate | | | | 2.0 | | | | | | |
| Mexoryl ® XL | Drometrizole Trisiloxane | | | | 4.0 | 3.0 | | | | 2.0 | |
| Uvinul ® T-150 | Ethylhexyl Triazone | 1.0 | 3.0 | 1.0 | 1.0 | 0.5 | 2.0 | | 1.0 | 1.0 | |
| Tinosorb ® S | Bis-Ethylhexyloxyphenol Methoxyphenyl Triazine | | 2.5 | 2.5 | 1.0 | 0.5 | | | 2.5 | 1.0 | 1.5 |
| Uvinul ® A Plus | Diethylamino Hydroxybenzoyl Hexyl Benzoate | | 1.0 | 1.0 | | 0.5 | 1.0 | 0.5 | | 1.0 | |
| Parsol ® SLX | Polysiloxane-15 | 3.0 | | 2.0 | | 2.0 | | | | 1.0 | |
| Uvasorb ® HEB | Diethylhexyl Butamido Triazone | | | 1.0 | | 0.5 | | 1.0 | | 0.5 | 1.0 |
| Water Soluble | | | | | | | | | | | |

-continued

| | | Spray/Mousse Emulsions, SPF >20 | | | | | | | | | |
|---|---|---|---|---|---|---|---|---|---|---|---|
| Raw material | INCI | 18.1 | 18.2 | 18.3 | 18.4 | 18.5 | 18.6 | 18.7 | 18.8 | 18.9 | 18.10 |
| UV Filters | | | | | | | | | | | |
| Neo Heliopan ® AP (Symrise) | Disodium Phenyl-dibenzimidazoletetra-sulphonate | 0.5 | 1.5 | 1.5 | 0.75 | 0.5 | 1.0 | 2.2 | 2.0 | 1.0 | 0.75 |
| Neo Heliopan ® Hydro (Symrise) | Phenylbenzimidazole-sulphonic Acid | 2.0 | 2.75 | 2.50 | 2.25 | 2.0 | 2.0 | 1.5 | 1.0 | 0.5 | 2.0 |
| Mexoryl ® SX | Terephthalylidene Dicamphor Sulfonic Acid | | | | 1.0 | 0.5 | | | | 0.5 | |
| Sulisobenzone | Benzophenone-4 | 0.75 | 0.75 | 0.75 | 0.75 | 0.75 | 0.75 | 0.75 | 0.75 | 0.75 | 0.75 |
| Neutralisation base | | qs | qs | qs | qs | qs | qs | qs | qs | qs | qs |
| Microfine UV attenuating Pigments | | | | | | | | | | | |
| Titanium Dioxide according to the invention | Titanium Dioxide, Aluminum Hydroxide, Cetearyl Nonanoate, Stearic Acid | 1.0 | 1.0 | 1.5 | 3.0 | 3.5 | 2.5 | 4.0 | 2.0 | 1.5 | 1.0 |
| | Zinc Oxide | | | | | | 3.0 | | | 1.5 | |
| Other oil soluble components | | | | | | | | | | | |
| PCL Liquid 100 (Symrise) | Cetearyl Octanoate | | | | | | 10.0 | | | | |
| Corapan TQ ® (Symrise) | Diethylhexyl 1,6-Naphthalate | | | | | | | | 3.0 | | |
| | C18-36 Acid Triglyceride | | 1.0 | 2.0 | | | | | | 2.0 | |
| Neutral oil (Symrise) | Caprylic/Capric Triglyceride | 10 | | | | | | | 5.0 | | |
| Isodragol ® (Symrise) | Triisononanoin | | | | | | 2.0 | | | | |
| Cetiol ® OE | Dicaprylyl Ether | | | | | | 3.0 | 1.0 | | | |
| | Dicaprylyl Carbonate | | | 5.0 | 2.0 | | 2.0 | | 5.0 | 10.0 | |
| | Isohexadecane | | | | | | | 3.0 | | | |
| | Ethylhexylglycerin | | | | | | | | | | 0.5 |
| | Cetyl Ricinoleate | | | | | | | | | | 0.1 |
| Tegosoft ® TN (Goldschmidt) | C12-15 Alkyl Benzoate | 5.0 | | | 10.0 | 8.0 | 5.0 | | 7.0 | | |
| Abil ® 100 (Goldschmidt) | Dimethicone | | | | | | | | | | 4.0 |
| Dow Corning ® 193 Fluid (Dow corning) | PEG-12 Dimethiconel | | | | | | 1.0 | | | | |
| | Cyclohexasiloxane | | | | | 10.0 | | | | | |
| | Cyclopentasiloxane | | | | | | | | 2.0 | | |
| | Phenyl Trimethicone | | | | | 3.0 | | | 2.0 | | |
| | Cyclomethicone | | | | | | | | 1.0 | 0.5 | |
| | Butylene Glycol Dicaprylate/Dicaprate | | 8.0 | 8.0 | | | | | 7.5 | 8.0 | 10.0 |
| Lanette ® 16 | Cetyl Alcohol | | | | | | | | 1.0 | | 0.5 |
| alpha-Bisabolol (Symrise) | Bisabolol | | 0.3 | 0.3 | | 0.2 | 0.1 | | | 0.3 | |
| Copherol ® 1250 | Tocopheryl Acetate | | 0.5 | 0.5 | 0.5 | 0.5 | 0.5 | | 0.5 | 0.5 | |
| D-Panthenol (BASF) | Panthenol | | 0.5 | 0.5 | 0.5 | | 0.5 | | 0.5 | 0.5 | |
| | Retinyl-Palmitate | | | | | | | 0.5 | | | |
| Frescolat ® ML | Menthyl Lactate | | | | | | 0.5 | | | | |
| Fragrance | Fragrance/Parfum | qs | qs | qs | qs | Qs | Qs | Qs | Qs | qs | Qs |
| | Taurine | | 1.0 | 1.0 | | | | | | 1.0 | 0.5 |
| | Creatinine | | 0.05 | 0.05 | | | | | | 0.05 | 0.05 |
| EDTA BD ® (BASF) | Disodium-EDTA | 0.2 | 0.2 | 0.2 | 0.15 | 0.15 | 0.15 | 0.2 | 0.15 | 0.2 | 0.15 |
| Viscosity modifiers/stability aids | | | | | | | | | | | |
| | Sodium Chloride | 0.5 | | | | | | | | | |
| Avicel ® PC 611 (FMC Corporation) | Microcystalline Cellulose and Cellulose Gum | | | | | 0.80 | | | | | |
| Keltrol ® T (Calgon) | Xanthan Gum | | | | | | | 0.3 | | 0.2 | |
| Pemulen ® TR 2 (Novion) | Acrylates/C10-30 Alkyl Acrylate Crosspolymer | | 0.2 | 0.2 | | 0.25 | | | 0.2 | 0.2 | |
| Film Forming Polymers | | | | | | | | | | | |
| Antaron ® V-216/516 | VP/Hexadecene Copolymer | | 0.5 | 0.5 | | | 2.0 | | | 0.5 | |
| Dermacryl ® 79 | Acrylates/Octylacrylamide Coplymer | | | | | | | | 1.0 | | |

-continued

| | | Spray/Mousse Emulsions, SPF >20 | | | | | | | | | |
|---|---|---|---|---|---|---|---|---|---|---|---|
| Raw material | INCI | 18.1 | 18.2 | 18.3 | 18.4 | 18.5 | 18.6 | 18.7 | 18.8 | 18.9 | 18.10 |
| | Trimethylpentanediol adipic acid glycerine copolymer | | | | | | | 1.0 | | | |
| Avalure ® UR 450/525 | PPG-17/IPDI/DMPA copolymer | | | 0.5 | | | | | | 0.5 | |
| Other water soluble components | | | | | | | | | | | |
| Water | Water (Aqua) | qs | qs | qs | qs | qs | Qs | Qs | Qs | Qs | Qs |
| Neutralisation base for acidic components such as carbomers, and/or stearic acid etc | | qs | qs | qs | qs | qs | Qs | Qs | | Qs | Qs |
| Biotive ® Troxerutin | Troxerutin | 0.3 | 0.4 | 0.6 | 0.2 | 0.2 | 0.3 | 0.4 | 0.2 | 0.4 | 0.1 |
| Preservation agents | | qs | qs | qs | qs | qs | Qs | Qs | Qs | Qs | Qs |
| 1,3-Butylene glycol | 1,3-Butylene Glycol | | | | | 3.0 | | | | | |
| Ethanol (96%) | Ethyl Alcohol | 5.0 | 3.0 | 3.0 | 4.0 | 12.0 | | 10.0 | | 5.0 | 5.0 |
| Glycerin 99% | Glycerin | 3.0 | 5.0 | 5.0 | 4.5 | | 5.0 | | 5.0 | 3.0 | 3.0 |
| Hydrolite ®-5 (Symrise) | Pentylene Glycol | | 5.0 | 5.0 | 3.0 | | | | | 3.0 | |
| Symdiol ® 68 (Symrise) | 1,2-hexylenediol and 1,2-Capryvlyldiol | | | | | | | | | 0.5 | |
| SymSave ® H (Symrise) | Hydroxyacetophenone | 0.7 | 0.5 | 0.5 | 0.5 | 0.7 | 0.7 | 0.7 | 0.7 | 0.5 | 0.7 |
| 1,2-Propylene glycol | Propylene Glycol | | | | | 5.0 | | 1.0 | 1.0 | 2.0 | |
| Soja extract | Glycine soja (soybean) germ extract | | | | | 1.0 | 0.5 | | | | |
| | Sodium Ascorbyl Phosphate | | | | | | 0.2 | | | | |
| DHA | Dihydroxyacetone | | | | | | | | | | |
| Water soluble dyestuff | | qs | qs | qs | qs | qs | Qs | Qs | Qs | Qs | Qs |
| Plant Extract(s) | | qs | qs | qs | qs | qs | Qs | Qs | Qs | Qs | Qs |
| Propellant | | | | | | | | | | | Qs |

Example 19

| | | Daily Protection Preparations | | | | | | | | |
|---|---|---|---|---|---|---|---|---|---|---|
| Raw material | INCI | 19.1 | 19.2 | 19.3 | 19.4 | 19.5 | 19.6 | 19.7 | 19.8 | 19.9 |
| | | Emulsifier | | | | | | | | |
| Emulsiphos ® (Symrise) | Potassium Cetyl Phosphate, Hydrogenated Palm Glycerides | 1.5 | 1.5 | 1.5 | | | | | | |
| Dracorin ® CE (Symrise) | Glyceryl Stearate Citrate | | | | | 2.5 | | | | |
| | PPG-1 Trideceth-6 | | | | | 0.5 | | | | |
| | Sorbitan Oleate | | | | | 0.5 | | | | |
| | Sucrose stearate | | | | | | | 0.8 | | |
| Hostacerin ® AMPS | Ammonium Polyacrylamido tauramide | | | | | | | | | 2.0 |
| | Polyglyceryl-3 Methyl-glucose Distearate | | | | | | 3.5 | | | |
| | Sorbitan Stearate | | | | | | | | 2.0 | |
| | Glyceryl Stearate | | | | | | | | | |
| | Isostearic Acid | 1.0 | 1.0 | 1.0 | | | | | | |
| | Stearic Acid | | | | | 2.0 | | 1.0 | 4.0 | |
| | PEG 40 Stearate | | | | | | | | 1.0 | |
| | PEG 100 Stearate | | | | 0.2 | 2.0 | | | | |
| | PEG-4 Laurate | | | | | | | 0.3 | | |
| Lanette ® E | Sodium Cetearyl Sulphate | | | | | | | | 0.5 | |
| | Steareth-2 | | | | 0.2 | | | | | |
| | Steareth-21 | | | | 1.0 | | | | | |
| | Laureth-7 | | | | 0.75 | | | | | |

-continued

| Daily Protection Preparations | | | | | | | | | | |
|---|---|---|---|---|---|---|---|---|---|---|
| Raw material | INCI | 19.1 | 19.2 | 19.3 | 19.4 | 19.5 | 19.6 | 19.7 | 19.8 | 19.9 |
| Oil Soluble UV Filters | | | | | | | | | | |
| Neo Heliopan ® AV (Symrise) | Ethylhexyl Methoxy-cinnamate | 8.0 | | | | | 4.0 | 3.0 | 5.5 | 5.0 |
| Neo Heliopan ® 303 (Symrise) | Octocrylene | | 3.0 | 3.0 | 1.0 | 2.0 | | | | |
| Neo Heliopan ® 357 (Symrise) | Butyl Methoxydibenzoyl-methane | 2.0 | 2.0 | 2.0 | 2.0 | 2.0 | 2.0 | 1.5 | 2.0 | 1.0 |
| Neo Heliopan ® HMS (Symrise) | Homosalate | | 3.0 | 3.0 | | 5.0 | | | | |
| Neo Heliopan ® OS (Symrise) | Ethylhexyl Salicylate | | 3.0 | 3.0 | 4.0 | 5.0 | | | 3.0 | |
| Mexoryl ® XL | Drometrizole Trisiloxane | | | | 4.0 | 3.0 | | | | 2.0 |
| Uvinul ® T-150 | Ethylhexyl Triazone | 1.0 | 3.0 | 1.0 | 1.0 | 0.5 | 2.0 | | 1.0 | 1.0 |
| Tinosorb ® S | Bis-Ethylhexyloxyphenol Methoxyphenyl Triazine | | 2.5 | 2.5 | 1.0 | 0.5 | | | 2.5 | 1.0 |
| Uvinul ® A Plus | Diethylamino Hydroxy-benzoyl Hexyl Benzoate | | 1.0 | 1.0 | | 0.5 | 1.0 | 0.5 | | 1.0 |
| Parsol ® SLX | Polysiloxane-15 | 3.0 | | 2.0 | | 2.0 | | | | 1.0 |
| Water Soluble UV Filters | | | | | | | | | | |
| Neo Heliopan ® AP (Symrise) | Disodium Phenyl-dibenzimidazoletetra-sulphonate | 0.25 | 0.5 | 0.5 | 1.0 | 1.25 | 1.0 | 1.5 | 2.0 | 0.5 |
| Neo Heliopan ® Hydro (Symrise) | Phenylbenzimidazole-sulphonic Acid | 2.8 | 2.8 | 2.8 | 1.8 | 2.64 | 1.8 | 1.3 | 2.9 | 1.3 |
| Mexoryl ® SX | Terephthalylidene Dicamphor Sulfonic Acid | | | | 0.5 | 0.5 | | | | 0.5 |
| Sulisobenzone | Benzophenone-4 | 0.5 | 0.5 | 0.5 | 0.5 | 0.5 | 0.5 | 0.5 | 0.5 | 0.5 |
| Neutralizing base | | qs | qs | qs | qs | qs | Qs | qs | qs | qs |
| Microfine UV attenuating Pigments | | | | | | | | | | |
| Titanium Dioxide according to the invention | Titanium Dioxide, Aluminum Hydroxide, Cetearyl Nonanoate, Stearic Acid | 0.5 | 1.5 | 2.0 | 1.0 | 1.0 | 0.5 | 3.0 | 1.0 | 0.25 |
| Other oil soluble components | | | | | | | | | | |
| Shea Butter | Butyrospemum Parkii | | | | | | | | | 2.0 |
| Corapan TQ ® (Symrise) | Diethylhexyl 1,6-Naphthalate | | | | | | | | | |
| Dragoxat ® 89 (Symrise) | Ethylhexyl Isononoate | 3.0 | 3.0 | 3.0 | | 3.0 | | | | |
| Isoadipate (Symrise) | Diisopropyl Adipate | | | | | 3.0 | | | | |
| Isopropyl myristate (Symrise) | Isopropyl Myristate | | | | 5.0 | 5.0 | | | | |
| | Tridecyl Trimellitate | | | | | | 2.0 | | | |
| | Myristyl Myristate | | | | | | | 5.0 | | |
| Neutral oil (Symrise) | Caprylic/Capric Triglyceride | | | | | | 3.0 | | 4.0 | |
| Cetiol ® OE | Dicaprylyl Ether | | | | | | 2.0 | | | |
| | Dicaprylyl Carbonate | 2.0 | 2.0 | 2.0 | | | | 3.0 | | |
| | Isohexadecane | | | | | | | | 8.0 | |
| | Ethylhexylglycerin | | | | | | 0.5 | | | |
| Paraffin oil | Mineral Oil | | | | 2.0 | | 0.5 | | | |
| Tegosoft ® TN (Goldschmidt) | C12-15 Alkyl Benzoate | | | | | | | | 3.0 | |
| Abil ® 100 (Goldschmidt) | Dimethicone | | | | 1.0 | | | | 2.0 | 1.0 |
| Dow Corning ® 193 Fluid (Dow corning) | PEG-12 Dimethicone | | | | 1.0 | 1.0 | | | | |
| | Hydrogenated Coco-Glycerides | | | | | | 1.0 | 0.5 | | |
| | Butylene Glycol Dicaprylate/Dicaprate | | | | | | | 7.5 | | |
| | Dibutyl Adipate | | | | 2.0 | | | | | |
| Lanette ® O | Cetearyl Alcohol | | | | 1.5 | | | | | |
| Lanette ® 16 | Cetyl Alcohol | 0.5 | 0.5 | 0.5 | 0.5 | 0.5 | 0.5 | 2.0 | 0.2 | |
| Lanette ® 18 | Stearyl Alcohol | | | | 0.5 | 0.5 | | | 4.5 | |
| | Myristyl Alcohol | | | | | | | | 1.0 | |
| Ceramide(s) | | | | | | | | | 0.5 | |

Daily Protection Preparations

| Raw material | INCI | 19.1 | 19.2 | 19.3 | 19.4 | 19.5 | 19.6 | 19.7 | 19.8 | 19.9 |
|---|---|---|---|---|---|---|---|---|---|---|
| alpha-Bisabolol (Symrise) | Bisabolol | | | | 0.2 | 0.1 | 0.2 | 0.1 | | |
| Copherol ® 1250 | Tocopheryl Acetate | 0.5 | 0.5 | 0.5 | 0.5 | 0.5 | 0.5 | 0.5 | 0.5 | 0.5 |
| D-Panthenol (BASF) | Panthenol | 1.0 | 1.0 | 1.0 | 0.5 | 0.5 | 0.5 | | 0.5 | 0.5 |
| | Retinyl Palmitate | 0.5 | 0.5 | 0.5 | | | | | 0.5 | |
| | Ubiquinone | 0.1 | | | | | | | | |
| Frescolat ® ML | Menthyl Lactate | 0.5 | | | | | | | | |
| Fragrance | Fragrance/Parfum | Qs | Qs | Qs | Qs | Qs | Qs | Qs | Qs | Qs |
| | Niacinamide | | 0.1 | | 0.5 | 0.5 | | | | |
| | Arbutin | | | 0.2 | | | | | | |
| 4-(1-Phenylethyl)1,3-benzenediol | | 0.2 | | | | 0.5 | | | | |
| | Kojic Acid | | | | 0.5 | | | | | |
| Liquorice extract | | | | | | | 0.5 | | | |
| | Glucosyl rutin + quercitrin | 0.1 | 0.1 | | | | 0.2 | | | |
| | Isoquercitrin | | | | | | 0.1 | | | |
| | Creatinine | 0.05 | | | | | | | | |
| EDTA BD ® (BASF) | Disodium-EDTA | 0.2 | 0.2 | 0.2 | 0.15 | 0.15 | 0.2 | 0.15 | 0.15 | 0.15 |
| Viscosity modifiers/stability aids | | | | | | | | | | |
| Carbopol ® Ultrez-10 (Noveon) | Carbomer | 0.15 | 0.15 | 0.15 | | 0.15 | 0.1 | | | 0.2 |
| Keltrol ® T (Calgon) | Xanthan Gum | 0.2 | 0.2 | 0.2 | | | | 0.2 | | |
| Pemulen ® TR 2 (Novion) | Acrylates/C10-30 Alkyl Acrylate Crosspolymer | | | | | | 0.2 | | | |
| Veegum ® ultra (Vanderbilt) | Magnesium Aluminium Silicate | | | | | | | | | 0.2 |
| Fucogel ® 1000 (Solabia) | Biosaccharide Gum-1 | | | | | 0.2 | | | | |
| Givobio GMg (Seppic) | Magnesium Gluconate | | | | | | 0.2 | | | |
| Sepigel ® 305 (Seppic) | Polyacrylamide and C13-14 Isoparaffin and Laureth-7 | | | | | | | | 3.0 | |
| Aerosil ® 200 | Silica | | | | | | | | | 0.3 |
| Other water soluble components | | | | | | | | | | |
| Water | Water (Aqua) | Qs | Qs | Qs | Qs | Qs | Qs | Qs | Qs | Qs |
| Neutralisation base for acidic components such as carbomers, and/or stearic acid etc | | Qs | Qs | Qs | Qs | Qs | Qs | Qs | Qs | Qs |
| Biotive ® Troxerutin (Symrise) | Troxerutin | 0.3 | 0.1 | 0.2 | 0.3 | 0.4 | 0.3 | 0.5 | 0.6 | 0.5 |
| Preservation agents | | Qs | Qs | Qs | Qs | Qs | Qs | Qs | Qs | Qs |
| 1,3-Butylene glycol | 1,3-Butylene Glycol | | | | | | 1.0 | 2.0 | 1.0 | 3.0 |
| Ethanol (96%) | Ethyl Alcohol | | | | | | | | | 3.0 |
| Glycerin 99% | Glycerin | | | | 5.0 | 5.00 | | 6.0 | 8.0 | |
| Hydrolite ®-5 (Symrise) | Pentylene Glycol | 5.0 | 5.0 | 5.0 | | 1.0 | | | | |
| Symdiol ® 68 (Symrise) | 1,2-hexylenediol and 1,2-Caprylyldiol | 0.5 | 0.5 | 0.5 | 0.5 | | | | | |
| SymSave ® H (Symrise) | Hydroxyacetophenone | 0.5 | 0.5 | 0.5 | 0.5 | 0.7 | 0.7 | 0.7 | 0.7 | 0.7 |
| 1,2-Propylene glycol | Propylene Glycol | | | | | | 1.0 | | | |
| Soja extract | Glycine soja (soybean) germ extract | 1.0 | | | | | | | 1.0 | |
| Peptides | | 0.3 | 0.3 | | 0.3 | 0.3 | | | | |
| | Sodium PCA | | | | | | | | 0.5 | |
| | Saccharomyces Ferment | | | | | | | | 0.3 | |
| | Ascorbyl Glucoside | | | | | | | | | 0.5 |
| Sodium or Magnesium Ascorbyl Phosphate | | 0.5 | 0.5 | 0.5 | | | | | | |
| DHA | Dihydroxyacetone | | | 5.0 | | | | 5.0 | | |
| Water soluble dyestuff | | Qs | Qs | Qs | Qs | Qs | Qs | Qs | Qs | Qs |
| Plant Extract(s) | | Qs | Qs | Qs | Qs | Qs | Qs | Qs | Qs | 5.0 |

What is claimed is:

1. Coated titanium dioxide particles, wherein at least one coating layer comprises an ester made from a mixture of $C_{12}$ to $C_{30}$ fatty alcohols and $C_6$ to $C_{12}$ aliphatic acids as coating material.

2. The particles of claim 1, wherein the coating material is at least a $C_{16}$-$C_{18}$ nonanoate derivative or mixture thereof.

3. The particles of claim 1, wherein the coating material comprises cetearyl nonoate and/or cetearyl isononoate.

4. The particles of claim 1, wherein the titanium dioxide particles comprise one or more additional coating layer, whereby the coating material is selected from the group consisting of silica (SiO2), aluminium hydroxide ($Al_2(OH)_3$), aluminium oxide ($Al_2O_3$), sodium hexametaphosphate ($Na(PO_3)_6$), sodium metaphosphate ($Na(PO_3)n$, aluminium stearate, stearic acid, lauric acid, dimethicone, or mixtures thereof.

5. The particles of claim 1, wherein the loading capacity of the coating material comprising a mixture of fatty acid esters, on the particles is in the range from 5 to 25%, referring to the total weight of a particle.

6. The particles of claim 4, wherein the loading capacity of the coating material is in the range of 5 to 15 wt.%, referring to the total weight of a particle.

7. The particles of claim 1, wherein at least one dimension of individual crystals making up agglomerates of the particles is <100 nm.

8. A cosmetic and/or pharmaceutical preparation comprising the coated titanium dioxide particles of claim 1.

9. The preparation of claim 8, wherein the amount of the titanium dioxide particles is in the range of 0.5 to 25%, referring to the total preparation.

10. The preparation of claim 8, further comprising at least one UV filter in an amount from 0.1 to 65.0%, referring to the total amount of all UV filters, referring to the total amount of the preparation.

11. The preparation of claim 10, wherein the UV filters are selected from the group consisting of:
Avobenzone,
Homosalate,
Octisalate,
Octocrylene,
2-Ethylhexyl p-methoxycinnamate,
Isoamyl p-methoxycinnamate,
3-(4'-methylbenzylidene)-d,l-camphor,
2,4,6-trianilino(p-carbo-2'-ethylhexyl-1'-oxy)-1,3,5-triazine,
Tris-Biphenyl Triazine,
Diethylhexyl Butamido Triazone,
Benzylidenemalonate-polysiloxane,
2-Ethylhexyl 4-dimethylaminobenzoate,
Drometrizole Trisiloxane,
Bis-Ethylhexyloxyphenol Methoxyphenyl Triazine,
2,2'-Methylenebis(6-(2H-benztriazol-2-yl)-4-1,1,3,3-tetramethylbutyl)-phenol),
Diethylamino Hydroxybenzoyl Hexyl Benzoate,
Disodium Phenyl-dibenzimidazole Tetrasulphonate and its salts,
Phenyibenzimidazole- sulphonic Acid and its salts,
Terephthalyiidene Dicamphor Sulfonic Acid and its salts,
Benzophenone-4 and its salts,
Benzophenone-3,
Menthyl anthranilate,
Padimate O,
Zinc oxide,
and their mixtures.

12. The preparation of claim 8, further comprising auxiliaries and additives selected from surfactants, oil bodies, co-emulsifiers, superfatting agents, pearlising waxes, consistency factors, polymers, silicone compounds, stabilizers, antidandruff agents, film formers, swelling agents, hydrotropes, preservatives, solubilizers, complexing agents, reducing agents, alkalising agents, perfume oils, dyes, fats, moisturizers, antioxidants, antiperspirants, insect repellants, self-tanning agents, tyrosine inhibitors (depigmenting agents), bodying agents, antimicrobial agents, antifoams, aqueous and non-aqueous plant extracts and the like as additional auxiliaries and additives.

13. The preparation of claim 8, having a sun protection factor of at least 2.

14. The preparation of claim 8, having a UVA protection factor of at least 2, measured by the Colipa Method for in vitro determination of UVA protection, 2011.

15. The preparation of claim 8, which is a dermatological preparation selected from the group consisting of creams, hydrogels, hydrodispersion gels, oil gels, lotions, balsams.

* * * * *